(12) United States Patent
Hammer

(10) Patent No.: US 7,700,842 B2
(45) Date of Patent: Apr. 20, 2010

(54) IDENTIFICATION OF A NEW CLASS OF EPSP SYNTHASES

(75) Inventor: Philip E. Hammer, Cary, NC (US)

(73) Assignee: Athenix Corporation, Research Triangle Park, NC (US)

( * ) Notice: Subject to any disclaimer, the term of this patent is extended or adjusted under 35 U.S.C. 154(b) by 648 days.

(21) Appl. No.: 11/400,598

(22) Filed: Apr. 7, 2006

(65) Prior Publication Data

US 2006/0253921 A1 Nov. 9, 2006

Related U.S. Application Data

(60) Provisional application No. 60/669,686, filed on Apr. 8, 2005, provisional application No. 60/678,348, filed on May 6, 2005, provisional application No. 60/695,193, filed on Jun. 29, 2005, provisional application No. 60/725,182, filed on Oct. 11, 2005.

(51) Int. Cl.
*C12N 15/52* (2006.01)
*C12N 15/82* (2006.01)

(52) U.S. Cl. ............... 800/300; 536/23.2; 800/288; 800/298; 800/300.1

(58) Field of Classification Search ............... None
See application file for complete search history.

(56) References Cited

U.S. PATENT DOCUMENTS 5,633,435 A * 5/1997 Barry et al. ............ 800/288
5,804,425 A 9/1998 Barry et al.
7,238,508 B2 * 7/2007 Lin et al. ............ 435/193
2003/0233675 A1 12/2003 Cao
2005/0223436 A1 10/2005 Lin

FOREIGN PATENT DOCUMENTS

WO WO 2005/014820 A1 2/2005

OTHER PUBLICATIONS

Buell et al, Sep. 2003, Proceedings of the National Academy of Science USA 100(18): 10181-10186.*
Wood et al 2001 Science 294: 2317-2323.*
NCBI Database Report for Accession No. AAL41658, Direct Submission on Sep. 27, 2001.
NCBI Database Report for Accession No. AAO54572, Direct Submission on Mar. 3, 2003.
NCBI Database Report for Accession No. AAY35946, Direct Submission on May 1, 2005.
NCBI Database Report for Accession No. AAZ35419, Direct Submission on Mar. 31, 2005.
He., M., et al., "A New Type of Class I Bacterial 5-enopyruvylshikimate-3-phosphate Synthase Mutants with Enhanced Tolerance to Glyphosate," *Biochimica et Biophysica Acta*, Nov. 7, 2001, pp. 1-6, vol. 1568, No. 1.

* cited by examiner

*Primary Examiner*—David H Kruse
(74) *Attorney, Agent, or Firm*—Alston & Bird LLP

(57) ABSTRACT

Compositions and methods for conferring tolerance to glyphosate in bacteria, plants, plant cells, tissues and seeds are provided. Compositions include a novel class of EPSPS enzymes, designated Class III, and polynucleotides encoding such enzymes, vectors comprising those polynucleotides, and host cells comprising the vectors. The novel proteins comprise at least one sequence domain selected from the Class III domains provided herein. These sequence domains can be used to identify EPSP synthases with glyphosate resistance activity.

15 Claims, 3 Drawing Sheets

IDENTIFICATION OF A NEW CLASS OF EPSP SYNTHASES

CROSS REFERENCE TO RELATED APPLICATION

This application claims the benefit of U.S. Provisional Application Ser. Nos. 60/669,686, filed Apr. 8, 2005; 60/678,348 filed May 6, 2005; 60/695,193 filed Jun. 29, 2005; and 60/725,182 filed Oct. 11, 2005, the contents of which are hereby incorporated in their entirety by reference herein.

FIELD OF THE INVENTION

This invention relates to plant molecular biology, particularly to a novel class of EPSP synthases that confer resistance to the herbicide glyphosate.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid (S3P) to 5-enolpyruvyl-3-phosphoshikimic acid. Inhibition of this enzyme (5-enolpyruvylshikimate-3-phosphate synthase; referred to herein as "EPSP synthase", or "EPSPS") kills plant cells by shutting down the shikimate pathway, thereby inhibiting aromatic amino acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases have a high tolerance to glyphosate.

Plant cells resistant to glyphosate toxicity can be produced by transforming plant cells to express glyphosate-resistant bacterial EPSP synthases. Notably, the bacterial gene from *Agrobacterium tumefaciens* strain CP4 has been used to confer herbicide resistance on plant cells following expression in plants. A mutated EPSP synthase from *Salmonella typhimurium* strain CT7 confers glyphosate resistance in bacterial cells, and confers glyphosate resistance on plant cells (U.S. Pat. Nos. 4,535,060; 4,769,061; and 5,094,945).

EPSP synthase (Mr 46,000) folds into two similar domains, each comprising three copies of a βαβαββ-folding unit (Stallings et al. (1991) *Proc. Natl. Acad. Sci. U.S.A.* 885046-5050). Lys-22, Arg-124, Asp-313, Arg-344, Arg-386, and Lys-411 are conserved residues of the EPSP synthase from *E. coli* (Schönbrunn et al. (2001) *Proc. Natl. Acad. Sci. U.S.A.* 98:1376-1380). Conserved residues important for EPSPS activity also include Arg-100, Asp-242, and Asp-384 (Selvapandiyan et al. (1995) *FEBS Letters* 374:253-256). Arg-27 binds to S3P (Shuttleworth et al. (1999) *Biochemistry* 38:296-302). Variants of the wild-type EPSPS enzyme have been isolated which are glyphosate-tolerant as a result of alterations in the EPSPS amino acid coding sequence (Kishore and Shah (1988) *Annu. Rev. Biochem.* 57:627-63; Wang et al. (2003) *J. Plant Res.* 116:455-60; Eschenburg et al. (2002) *Planta* 216:129-35). He et al. (2001, *Biochim et Biophysica Acta* 1568:1-6) have developed EPSP synthases with increased glyphosate tolerance by mutagenesis and recombination between the *E. coli* and *Salmonella typhimurium* EPSPS genes, and suggest that mutations at position 42 (T42M) and position 230 (Q230K) are likely responsible for the observed resistance. Subsequent work (He et al (2003) *Biosci. Biotech. Biochem.* 67:1405-1409) shows that the T42M mutation (threonine to methionine) is sufficient to improve tolerance of both the *E.coli* and *Salmonella typhimurium* enzymes.

Due to the many advantages herbicide resistance plants provide, methods for identifying herbicide resistance genes with glyphosate resistance activity are desirable.

SUMMARY OF INVENTION

Compositions and methods for conferring tolerance to glyphosate in bacteria, plants, plant cells, tissues and seeds are provided. Compositions include a novel class of EPSPS enzymes, designated Class III, and polynucleotides encoding such enzymes, vectors comprising those polynucleotides, and host cells comprising the vectors. The novel proteins comprise at least one sequence domain selected from the following domains (Class III domains):

Domain I:

L-A-K-G-$X_1$-S-$X_2$-L-$X_3$-G-A-L-K-S-D-D-T (SEQ ID NO: 13), where $X_1$ denotes lysine or threonine, where $X_2$ denotes arginine or histidine, where $X_3$ denotes serine or threonine;

Domain Ia:

L-A-K-G-$X_1$, (SEQ ID No:14), where $X_1$ denotes lysine or threonine;

Domain Ib:

S-$X_1$-L-$X_2$ (SEQ ID NO: 15), where $X_1$ denotes arginine or histidine, where $X_2$ denotes serine or threonine;

Domain Ic:

```
     G-A-L-K-S-D-D-T;        (SEQ ID NO: 16)
```

Domain II:

E-P-D-$X_1$-$X_2$-T-F-$X_3$-V-$X_4$-$X_5$-$X_6$-G (SEQ ID NO:17), where $X_1$ denotes aspartic acid or alanine, where $X_2$ denotes serine or threonine, where $X_3$ denotes valine or isoleucine, where $X_4$ denotes threonine or glutamic acid or lysine, where $X_5$ denotes serine or glycine, where $X_6$ denotes glutamine or serine or glutamic acid or threonine;

Domain IIa:

E-P-D-$X_1$-$X_2$-T-F-$X_3$-V (SEQ ID NO: 18), where $X_1$ denotes aspartic acid or alanine, where $X_2$ denotes serine or threonine, where $X_3$ denotes valine or isoleucine;

Domain IIb:

$X_1$-$X_2$-$X_3$-G (SEQ ID NO:19), where $X_1$ denotes threonine or glutamic acid or lysine, where $X_2$ denotes serine or glycine, where $X_3$ denotes glutamine or serine or glutamic acid or threonine;

Domain III:

```
     RFLTAA;                 (SEQ ID NO: 20)
```

Domain IV:

```
     KRPI(G/M)P              (SEQ ID NO: 21)
```

K-R-P-I-$X_1$-P, where $X_1$ denotes glycine or methionine or leucine;

Domain V:

$X_1$-G-C-P-P-V (SEQ ID NO:22), where $X_1$ denotes threonine or serine;

Domain VI:

I-G-A-$X_1$-G-Y-$X_2$-D-L-T (SEQ ID NO:23), where $X_1$ denotes arginine or lysine or leucine, and where $X_2$ denotes isoleucine or valine;

Domain VII:

W-$X_1$-V-$X_2$-$X_3$-T-G (SEQ ID NO:24), where $X_1$ denotes arginine or lysine, where $X_2$ denotes alanine or histidine or glutamic acid or serine, where $X_3$ denotes proline or alanine;

Domain VIII:

E-P-D-A-S-A-A-T-Y-L-W-$X_1$-A-$X_2$-$X_3$-L (SEQ ID NO:25), where $X_1$ denotes alanine or glycine, where $X_2$ denotes glutamic acid or glutamine, where $X_3$ denotes valine or leucine or alanine;

Domain VIIIa:

```
E-P-D-A-S-A-A-T-Y-L-W;      (SEQ ID NO: 26)
```

Domain IX:

I-D-$X_1$-G (SEQ ID NO:27), where $X_1$ denotes isoleucine or leucine;

Domain X:

F-$X_1$-Q-P-D-A-K-A (SEQ ID NO:28), where $X_1$ denotes threonine or serine;

Domain XI:

$X_1$-F-P-$X_2$-$X_3$-$X_4$-A-$X_5$-$X_6$-$X_7$-G-S-Q-M-Q-D-A-I-P-T-$X_8$-A-V-$X_9$-A-A-F-N (SEQ ID NO:29), where $X_1$ denotes glutamine or lysine or serine, where $X_2$ denotes asparagine or histidine, where $X_3$ denotes methionine or leucine, where $X_4$ denotes proline or glutamine, where $X_5$ denotes threonine or glutamic acid or valine, where $X_6$ denotes valine or isoleucine, where $X_7$ denotes aspartic acid or valine, where $X_8$ denotes leucine or isoleucine, where $X_9$ denotes leucine or isoleucine;

Domain XIa:

$X_1$-F-P-$X_2$-$X_3$-$X_4$-A (SEQ ID NO:30), where $X_1$ denotes glutamine or lysine or serine, where $X_2$ denotes asparagine or histidine, where $X_3$ denotes methionine or leucine, where $X_4$ denotes proline or glutamine;

Domain XIb:

$X_1$-$X_2$-$X_3$-G-S-Q-M-Q-D-A-I-P-T-$X_4$-A-V-$X_5$-A-A-F-N (SEQ ID NO:31), where $X_1$ denotes threonine or glutamic acid or valine, where $X_2$ denotes valine or isoleucine, where $X_3$ denotes aspartic acid or valine, where $X_4$ denotes leucine or isoleucine, where $X_5$ denotes leucine or isoleucine;

Domain XIc:

```
G-S-Q-M-Q-D-A-I-P-T;       (SEQ ID NO: 32)
```

Domain XII:

P-V-R-F-$X_1$-$X_2$-$X_3$-$X_4$-N-L-R-V-K-E-C-D-R-$X_5$ (SEQ ID NO:33), where $X_1$ denotes valine or threonine, where $X_2$ denotes glutamic acid or glycine, where $X_3$ denotes leucine or isoleucine, where $X_4$ denotes alanine or glutamic acid, where $X_5$ denotes isoleucine or valine;

Domain XIIa:

```
P-V-R-F;             (SEQ ID NO: 34)
```

Domain XIIb:

$X_1$-$X_2$-$X_3$-$X_4$-N-L-R-V-K-E-C-D-R-$X_5$ (SEQ ID NO:35), where $X_1$ denotes valine or threonine, where $X_2$ denotes glutamic acid or glycine, where $X_3$ denotes leucine or isoleucine, where $X_4$ denotes alanine or glutamic acid, where $X_5$ denotes isoleucine or valine;

Domain XIIc:

```
N-L-R-V-K-E-C-D-R;        (SEQ ID NO: 36)
```

Domain XIII:

E-G-D-D-L-$X_1$-$X_2$ (SEQ ID NO:37), where $X_1$ denotes leucine or isoleucine, where $X_2$ denotes valine or isoleucine;

Domain XIV:

$X_1$-P-$X_2$-L-A-G (SEQ ID NO:38), where $X_1$ denotes aspartic acid or asparagine, where $X_2$ denotes alanine or serine or threonine;

Domain XV:

A-$X_1$-I-D-$X_2$-$X_3$-$X_4$-D-H-R (SEQ ID NO:39), where $X_1$ denotes leucine or serine or glutamic acid, where $X_2$ denotes threonine or serine, where $X_3$ denotes histidine or phenylalanine, where $X_4$ denotes alanine or serine;

Domain XVI:

F-A-L-A-$X_1$-L-K-$X_2$-$X_3$-G-I (SEQ ID NO:40), where $X_1$ denotes glycine or alanine, where $X_2$ denotes isoleucine or valine, where $X_3$ denotes serine or glycine or alanine or lysine;

Domain XVIa:

F-A-L-A-$X_1$-L-K (SEQ ID NO:41), where $X_1$ denotes glycine or alanine;

Domain XVIb:

L-K-$X_1$-$X_2$-G-I (SEQ ID NO:42), where $X_1$ denotes isoleucine or valine, where $X_2$ denotes serine or glycine or alanine or lysine; and Domain XVII:

-$X_1$-P-$X_2$-C-V-$X_3$-K (SEQ ID NO:43), where $X_1$ denotes asparagine or aspartic acid, where $X_2$ denotes alanine or aspartic acid, where $X_3$ denotes alanine or glycine.

Domain XVIII:

$X_1$-S-L-G-V (SEQ ID NO:44), where $X_1$ denotes alanine or serine or proline.

The above domains set forth in SEQ ID NOS:13-44 were identified by aligning Class III sequences that share at least 50% sequence identity. The presence of at least one of these sequence domains is predictive of glyphosate resistance activity.

Isolated nucleic acid molecules corresponding to herbicide resistance-conferring nucleic acid sequences are provided. Additionally, amino acid sequences corresponding to the polynucleotides are encompassed. In particular, the present invention provides for isolated nucleic acid molecules comprising a Class III domain, including the nucleotide sequence set forth in SEQ ID NOS:9, 11, 55, 57 and 58, a nucleotide sequence encoding the amino acid sequence shown in SEQ ID NO:10, 12, 56, and 59, the herbicide resistance nucleotide sequence deposited in a bacterial host as Accession Nos. B-30833 and B-30838, as well as variants and fragments thereof. Nucleotide sequences that are complementary to a nucleotide sequence of the invention, or that hybridize to a sequence of the invention are also encompassed. The sequences find use in the construction of expression vectors for subsequent transformation into plants of interest, as probes for the isolation of other glyphosate resistance genes, as selectable markers, and the like.

Plasmids containing the herbicide resistance nucleotide sequences of the invention were deposited in the permanent collection of the Agricultural Research Service Culture Collection, Northern Regional Research Laboratory (NRRL) on Apr. 4, 2005, and assigned Accession No. B-30833. This deposit will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposit with the ATCC. This deposit was made merely as a convenience for those of skill in the art and is not an admission that a deposit is required under 35 U.S.C. §112.

Compositions also include antibodies to the polypeptides as well as synthetic polynucleotides encoding herbicide resistance polypeptides. The coding sequences can be used in DNA constructs or expression cassettes for transformation and expression in organisms, including microorganisms and plants. Compositions also comprise transformed bacteria, plants, plant cells, tissues, and seeds that are glyphosate tolerant by the introduction of the compositions of the invention into the genome of the organism. Where the organism is a plant, the introduction of the sequence allows for glyphosate containing herbicides to be applied to the crop to selectively kill the glyphosate sensitive weeds, but not the transformed organism.

Methods for identifying an EPSP synthase with glyphosate resistance activity are additionally provided. The methods comprise obtaining an amino acid sequence for an EPSP synthase, and identifying whether the amino acid sequence comprises at least one sequence domain of the invention.

The EPSP synthases described herein represent a new class of EPSPS enzymes, referred to hereinafter as Class III EPSPS enzymes.

DESCRIPTION OF FIGURES

FIG. 1A-C shows an alignment of EPSP synthase amino acid sequences. The conserved residues that have been identified as important for substrate binding and for EPSPS activity are boxed. The boxes delineate the amino acid locations of the Class III domains. Roman numerals above the boxes correspond to the Class III domains.

DETAILED DESCRIPTION OF THE INVENTION

The present invention is drawn to compositions and methods for conferring herbicide tolerance, particularly glyphosate tolerance, in organisms is provided. The methods involve transforming organisms with nucleotide sequences encoding a Class III glyphosate tolerance gene of the invention. In particular, the present invention recognizes a class of enzymes that confers glyphosate tolerance and nucleotide sequences encoding such enzymes. The sequences find use in preparing plants that show increased tolerance to the herbicide glyphosate. Thus, transformed bacteria, plants, plant cells, plant tissues and seeds are provided.

The Class III enzymes are characterized by having at least one domain selected from the domains listed below, herein referred to as Class III domains:

Domain I:

L-A-K-G-$X_1$-S-$X_2$-L-$X_3$-G-A-L-K-S-D-D-T (SEQ ID NO:13), where $X_1$ denotes lysine or threonine, where $X_2$ denotes arginine or histidine, where $X_3$ denotes serine or threonine;

Domain Ia:

L-A-K-G-$X_1$, (SEQ ID NO:14), where $X_1$ denotes lysine or threonine;

Domain Ib:

S-$X_1$-L-$X_2$ (SEQ ID NO:15), where $X_1$ denotes arginine or histidine, where $X_2$ denotes serine or threonine;

Domain Ic:

```
    G-A-L-K-S-D-D-T;      (SEQ ID NO: 16)
```

Domain II:

E-P-D-$X_1$-$X_2$-T-F-$X_3$-V-$X_4$-$X_5$-$X_6$-G (SEQ ID NO:17), where $X_1$ denotes aspartic acid or alanine, where $X_2$ denotes serine or threonine, where $X_3$ denotes valine or isoleucine, where $X_4$ denotes threonine or glutamic acid or lysine, where $X_5$ denotes serine or glycine, where $X_6$ denotes glutamine or serine or glutamic acid or threonine;

Domain IIa:

E-P-D-$X_1$-$X_2$-T-F-$X_3$-V (SEQ ID NO:18), where $X_1$ denotes aspartic acid or alanine, where $X_2$ denotes serine or threonine, where $X_3$ denotes valine or isoleucine;

Domain IIb:

$X_1$-$X_2$-$X_3$-G (SEQ ID NO:19), where $X_1$ denotes threonine or glutamic acid or lysine, where $X_2$ denotes serine or glycine, where $X_3$ denotes glutamine or serine or glutamic acid or threonine;

Domain III:

```
    RFLTAA;          (SEQ ID NO: 20)
```

Domain IV:

KRPI(G/M)P (SEQ ID NO:21)

K-R-P-I-$X_1$-P, where $X_1$ denotes glycine or methionine or leucine;

Domain V:

$X_1$-G-C-P-P-V (SEQ ID NO:22), where $X_1$ denotes threonine or serine;

Domain VI:

I-G-A-$X_1$-G-Y-$X_2$-D-L-T (SEQ ID NO:23), where $X_1$ denotes arginine or lysine or leucine, and where $X_2$ denotes isoleucine or valine;

Domain VII:

W-$X_1$-V-$X_2$-$X_3$-T-G (SEQ ID NO:24), where $X_1$ denotes arginine or lysine, where $X_2$ denotes alanine or histidine or glutamic acid or serine, where $X_3$ denotes proline or alanine;

Domain VIII:

E-P-D-A-S-A-A-T-Y-L-W-$X_1$-A-$X_2$-$X_3$-L (SEQ ID NO:25), where $X_1$ denotes alanine or glycine, where $X_2$ denotes glutamic acid or glutamine, where $X_3$ denotes valine or leucine or alanine;

Domain VIIIa:

```
E-P-D-A-S-A-A-T-Y-L-W;        (SEQ ID NO: 26)
```

Domain IX:

I-D-$X_1$-G (SEQ ID NO:27), where $X_1$ denotes isoleucine or leucine;

Domain X:

F-$X_1$-Q-P-D-A-K-A (SEQ ID NO:28), where $X_1$ denotes threonine or serine;

Domain XI:

$X_1$-F-P-$X_2$-$X_3$-$X_4$-A-$X_5$-$X_6$-$X_7$-G-S-Q-M-Q-D-A-I-P-T-$X_8$-A-V-$X_9$-A-A-F-N (SEQ ID NO:29), where $X_1$ denotes glutamine or lysine or serine, where $X_2$ denotes asparagine or histidine, where $X_3$ denotes methionine or leucine, where $X_4$ denotes proline or glutamine, where $X_5$ denotes threonine or glutamic acid or valine, where $X_6$ denotes valine or isoleucine, where $X_7$ denotes aspartic acid or valine, where $X_8$ denotes leucine or isoleucine, where $X_9$ denotes leucine or isoleucine;

Domain XIa:

$X_1$-F-P-$X_2$-$X_3$-$X_4$-A (SEQ ID NO:30), where $X_1$ denotes glutamine or lysine or serine, where $X_2$ denotes asparagine or histidine, where $X_3$ denotes methionine or leucine, where $X_4$ denotes proline or glutamine;

Domain XIb:

$X_1$-$X_2$-$X_3$-G-S-Q-M-Q-D-A-I-P-T-$X_4$-A-V-$X_5$-A-A-F-N (SEQ ID NO:31), where $X_1$ denotes threonine or glutamic acid or valine, where $X_2$ denotes valine or isoleucine, where $X_3$ denotes aspartic acid or valine, where $X_4$ denotes leucine or isoleucine, where $X_5$ denotes leucine or isoleucine;

Domain XIc:

```
G-S-Q-M-Q-D-A-I-P-T;        (SEQ ID NO: 32)
```

Domain XII:

P-V-R-F-$X_1$-$X_2$-$X_3$-$X_4$-N-L-R-V-K-E-C-D-R-$X_5$ (SEQ ID NO:33), where $X_1$ denotes valine or threonine, where $X_2$ denotes glutamic acid or glycine, where $X_3$ denotes leucine or isoleucine, where $X_4$ denotes alanine or glutamic acid, where $X_5$ denotes isoleucine or valine;

Domain XIIa:

```
P-V-R-F;        (SEQ ID NO: 34)
```

Domain XIIb:

$X_1$-$X_2$-$X_3$-$X_4$-N-L-R-V-K-E-C-D-R-$X_5$ (SEQ ID NO:35), where $X_1$ denotes valine or threonine, where $X_2$ denotes glutamic acid or glycine, where $X_3$ denotes leucine or isoleucine, where $X_4$ denotes alanine or glutamic acid, where $X_5$ denotes isoleucine or valine;

Domain XIIc:

```
N-L-R-V-K-E-C-D-R;        (SEQ ID NO: 36)
```

Domain XIII:

E-G-D-D-L-$X_1$-$X_2$ (SEQ ID NO:37), where $X_1$ denotes leucine or isoleucine, where $X_2$ denotes valine or isoleucine;

Domain XIV:

$X_1$-P-$X_2$-L-A-G (SEQ ID NO:38), where $X_1$ denotes aspartic acid or asparagine, where $X_2$ denotes alanine or serine or threonine;

Domain XV:

A-$X_1$-I-D-$X_2$-$X_3$-$X_4$-D-H-R (SEQ ID NO:39), where $X_1$ denotes leucine or serine or glutamic acid, where $X_2$ denotes threonine or serine, where $X_3$ denotes histidine or phenylalanine, where $X_4$ denotes alanine or serine;

Domain XVI:

F-A-L-A-$X_1$-L-K-$X_2$-$X_3$-G-I (SEQ ID NO:40), where $X_1$ denotes glycine or alanine, where $X_2$ denotes isoleucine or valine, where $X_3$ denotes serine or glycine or alanine or lysine;

Domain XVIa:

F-A-L-A-$X_1$-L-K (SEQ ID NO:41), where $X_1$ denotes glycine or alanine;

Domain XVIb:

L-K-$X_1$-$X_2$-G-I (SEQ ID NO:42), where $X_1$ denotes isoleucine or valine, where $X_2$ denotes serine or glycine or alanine or lysine; and Domain XVII:

-$X_1$-P-$X_2$-C-V-$X_3$-K (SEQ ID NO:43), where $X_1$ denotes asparagine or aspartic acid, where $X_2$ denotes alanine or aspartic acid, where $X_3$ denotes alanine or glycine.

Domain XVIII:

$X_1$-S-L-G-V (SEQ ID NO:44), where $X_1$ denotes alanine or serine or proline.

The above domains set forth in SEQ ID NOS:13-44 were identified by aligning Class III sequences that share at least 50% sequence identity. In some embodiments at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 of these sequence domains are present.

Using the methods of the invention and the identified domains, additional proteins (for example, SEQ ID NOS:2, 4, 46 and 48) which confer glyphosate tolerance can be identified. These proteins include known proteins as well as newly identified proteins (for example, SEQ ID NOS:10, 12, 56, and 59).

By "glyphosate" is intended any herbicidal form of N-phosphonomethylglycine (including any salt thereof) and other forms that result in the production of the glyphosate anion in planta. An "herbicide resistance protein," "herbicide tolerant protein," or a protein resulting from expression of an "herbicide resistance-" or "herbicide tolerance-" encoding polynucleotide includes proteins that confer upon a cell the ability to tolerate a higher concentration of an herbicide than cells that do not express the protein, or to tolerate a certain concentration of an herbicide for a longer period of time than cells that do not express the protein. A "glyphosate resistance protein" or a "glyphosate tolerant protein" includes a protein that confers upon a cell the ability to tolerate a higher concentration of glyphosate than cells that do not express the protein, or to tolerate a certain concentration of glyphosate for a longer time than cells that do not express the protein. By "tolerate" or "tolerance" is intended either to survive, or to carry out essential cellular functions such as protein synthesis and respiration in a manner that is not readily discernable from untreated cells.

Isolated Polynucleotides, and Variants and Fragments Thereof

One aspect of the invention pertains to isolated polynucleotides other than the polynucleotide sequences listed in SEQ ID NOS:1, 3, 7, 45, 47, and 53 encoding EPSP synthase enzymes having at least one Class III sequence domain of the invention. By "other than" is intended that the invention does not include the polynucleotide sequences set forth in the recited SEQ ID NOS.

The isolated polynucleotides of the present invention comprise nucleotide sequences encoding herbicide resistance proteins and polypeptides or biologically active portions thereof, as well as polynucleotides sufficient for use as hybridization probes to identify herbicide resistance-encoding polynucleotides. As used herein, the term "polynucleotide" is intended to include DNA molecules (e.g., cDNA or genomic DNA) and RNA molecules (e.g., mRNA) and analogs of the DNA or RNA generated using nucleotide analogs. The polynucleotide can be single-stranded or double-stranded DNA.

Nucleotide sequences of the invention include those characterized by the domains included above. The information used in identifying these domains include sequence alignments of glyphosate-sensitive EPSPS molecules. The sequence alignments were used to identify regions of homology between the sequences and to identify the Class III domains that are characteristic of Class III EPSPS enzymes.

Variants of the domains are also encompassed within the scope of the invention (for example SEQ ID NO:55). Such variants include sequences sharing at least 90%, at least 95%, 96%, 97%, 98% or 99% sequence identity and are contained in a DNA molecule that imparts glyphosate tolerance.

An "isolated" or "purified" polynucleotide or protein, or biologically active portion thereof, is substantially free of other cellular material, or culture medium when produced by recombinant techniques, or substantially free of chemical precursors or other chemicals when chemically synthesized. Preferably, an "isolated" polynucleotide is free of sequences (for example, protein encoding sequences) that naturally flank the polynucleotide (i.e., sequences located at the 5' and 3' ends of the polynucleotide) in the genomic DNA of the organism from which the polynucleotide is derived. For purposes of the invention, "isolated" when used to refer to polynucleotides excludes isolated chromosomes. For example, in various embodiments, the isolated glyphosate resistance-encoding polynucleotide can contain less than about 5 kb, 4 kb, 3 kb, 2 kb, 1 kb, 0.5 kb, or 0.1 kb of nucleotide sequence that naturally flanks the polynucleotide in genomic DNA of the cell from which the polynucleotide is derived. An herbicide resistance protein that is substantially free of cellular material includes preparations of protein having less than about 30%, 20%, 10%, or 5% (by dry weight) of non-herbicide resistance protein (also referred to herein as a "contaminating protein").

Polynucleotides that are fragments of these herbicide resistance-encoding nucleotide sequences are also encompassed by the present invention (for example, SEQ ID NOS:57, 58, and 60). By "fragment" is intended a portion of the nucleotide sequence encoding an herbicide resistance protein (for example, SEQ ID NO:59). A fragment of a nucleotide sequence may encode a biologically active portion of an herbicide resistance protein, or it may be a fragment that can be used as a hybridization probe or PCR primer using methods disclosed below. Polynucleotides that are fragments of an herbicide resistance nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 contiguous nucleotides, or up to the number of nucleotides present in a full-length herbicide resistance-encoding nucleotide sequence disclosed herein. By "contiguous" nucleotides is intended nucleotide residues that are immediately adjacent to one another.

Fragments of the nucleotide sequences of the present invention generally will comprise at least one of the Class III domains described herein, and will encode protein fragments that retain the biological activity of the full-length glyphosate resistance protein; i.e., herbicide-resistance activity. By "retains herbicide resistance activity" is intended that the fragment will have at least about 30%, at least about 50%, at least about 70%, or at least about 80% of the herbicide resistance activity of the full-length glyphosate resistance protein disclosed herein as SEQ ID NO:6. Methods for measuring herbicide resistance activity are well known in the art. See, for example, U.S. Pat. Nos. 4,535,060, and 5,188,642, each of which are herein incorporated by reference in their entirety.

A fragment of an herbicide resistance-encoding nucleotide sequence that encodes a biologically active portion of a protein of the invention will encode at least about 15, 25, 30, 50, 75, 100, 125, 150, 175, 200, 250, 300, 350, 400 contiguous amino acids, or up to the total number of amino acids present in a full-length herbicide resistance protein of the invention. Importantly, the fragment will comprise at least one of the Class III domains described herein.

Herbicide resistance proteins of the present invention are those characterized as Class III or fragments or variants thereof that retain activity. The term "sufficiently identical" is intended an amino acid or nucleotide sequence that has at least about 60% or 65% sequence identity, at least about 70% or 75% sequence identity, at least about 80% or 85% sequence identity, or at least about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two polynucleotides, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403-410. BLAST nucleotide searches can be performed with the BLASTN program, score=100, wordlength=12, to obtain nucleotide sequences homologous to GDC-like polynucleotides of the invention. BLAST protein searches can be performed with the BLASTX program, score=50, wordlength=3, to obtain amino acid sequences homologous to herbicide resistance protein molecules of the invention. To obtain gapped alignments for comparison purposes, Gapped BLAST can be utilized as described in Altschul et al. (1997) *Nucleic Acids Res.* 25:3389-2402. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., San Diego, Calif.). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant polynucleotides. "Variants" of the herbicide resistance-encoding nucleotide sequences include those sequences that encode the herbicide resistance protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the herbicide resistance proteins disclosed in the present invention as discussed below. Variant proteins encompassed by the present invention are biologically active, that is they retain the desired biological activity of the native protein, that is, herbicide resistance activity. By "retains herbicide resistance activity" is intended that the variant will have at least about 30%, at least about 50%, at least about 70%, or at least about 80% of the herbicide resistance activity of the native protein. Methods for measuring herbicide resistance activity are well known in the art. See, for example, U.S. Pat. Nos. 4,535,060, and 5,188,642, each of which are herein incorporated by reference in their entirety.

The skilled artisan will further appreciate that changes can be introduced by mutation into the nucleotide sequences of the invention thereby leading to changes in the amino acid sequence of the encoded herbicide resistance proteins, without altering the biological activity of the proteins. Thus, variant isolated polynucleotides can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of an herbicide resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for the ability to confer herbicide resistance activity to identify mutants that retain activity. Following mutagenesis, the encoded protein can be expressed recombinantly, and the activity of the protein can be determined using standard assay techniques.

Using methods such as PCR, hybridization, and the like corresponding herbicide resistance sequences can be identified by looking for the conserved domains of the invention. See, for example, Sambrook and Russell (2001) *Molecular Cloning: A Laboratory Manual* (Cold Spring Harbor Laboratory Press, Cold Spring Harbor, N.Y.) and Innis, et al. (1990) *PCR Protocols: A Guide to Methods and Applications* (Academic Press, St Louis, Mo.).

In a hybridization method, all or part of the herbicide resistance nucleotide sequence or a domain can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, or at least about 50, 75, 100, 125, 150, 175, 200, 250, 300, 350, 400, 500, 600, 700, 800, 900, 1000, 1200, 1400, 1600, 1800 consecutive nucleotides of herbicide resistance-encoding nucleotide sequence of the invention or a fragment or variant thereof. Methods for the preparation of probes for hybridization are generally known in the art and are disclosed in Sambrook and Russell, 2001, supra and Sambrook et al. (1989) *Molecular Cloning: A Laboratory Manual* (2d ed., Cold Spring Harbor Laboratory Press, Cold Spring Harbor, N.Y.), both of which are herein incorporated by reference.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, or less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of polynucleotides is found in Tijssen (1993) *Laboratory Techniques in Biochemistry and Molecular Biolog—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Herbicide resistance proteins are also encompassed within the present invention. By "herbicide resistance protein" is intended a Class III protein having at least one of the domains set forth above, including, for example, SEQ ID NOS:10, 12, 56, and 59. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity. Methods for measuring herbicide resistance activity are well known in the art. See, for example, U.S. Pat. Nos. 4,535,060, and 5,188,642, each of which are herein incorporated by reference in their entirety.

By "variants" is intended proteins or polypeptides having an amino acid sequence that is at least about 60%, 65%, about 70%, 75%, about 80%, 85%, or about at least 90%, 91%, 92%, 93%, 94%, 95%, 96%, 97%, 98% or 99% identical to a Class III enzyme. Variants also include polypeptides encoded by a polynucleotide that hybridizes to the polynucleotide encoding a Class III enzyme, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining herbicide resistance activity. Methods for measuring herbicide resistance activity are well known in the art. See, for example, U.S. Pat. Nos. 4,535,060, and 5,188,642, each of which are herein incorporated by reference in their entirety.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as Bacillus sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants that confer herbicide resistance (for example, SEQ ID NO:59 encoded by SEQ ID NO:58). These herbicide resistance proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Transformation of Bacterial or Plant Cells

Transformation of bacterial cells is accomplished by one of several techniques known in the art, not limited to electroporation, or chemical transformation (See, for example, Ausubel (ed.) (1994) *Current Protocols in Molecular Biology*, John Wiley and Sons, Inc., Indianapolis, Ind.). Markers conferring resistance to toxic substances are useful in identifying transformed cells (having taken up and expressed the test DNA) from non-transformed cells (those not containing or not expressing the test DNA). In one aspect of the invention, genes are useful as a marker to assess transformation of bacterial or plant cells.

Transformation of plant cells can be accomplished in similar fashion. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous polynucleotide sequences or DNA fragments into the plant cell. By "stable transformation" is intended that the nucleotide construct introduced into a plant integrates into the genome of the plant and is capable of being inherited by progeny thereof.

The genes of the invention may be modified to obtain or enhance expression in plant cells. The herbicide resistance sequences of the invention may be provided in expression cassettes for expression in the plant of interest. "Plant expression cassette" includes DNA constructs that are capable of resulting in the expression of a protein from an open reading frame in a plant cell. The cassette will include in the 5'-3' direction of transcription, a transcriptional initiation region (i.e., promoter) operably-linked to a DNA sequence of the invention, and a transcriptional and translational termination region (i.e., termination region) functional in plants. In some embodiments, the transcriptional initiation region will cause the production of an RNA sequence that allows for sufficient expression of the encoded EPSPS enzyme to enhance the glyphosate tolerance of a plant cell transformed with the polynucleotide. By "sufficient expression" is intended that the transcription initiation region will provide for the expression of an amount of the glyphosate-resistant polypeptide of the invention (e.g., those containing a Class III domain) that will confer upon a plant or cell the ability to tolerate a higher concentration of glyphosate than plants or cells that do not contain or express the protein, or to tolerate a certain concentration of glyphosate for a longer time than plants or cells that do not contain or express the protein.

The cassette may additionally contain at least one additional gene to be cotransformed into the organism, such as a selectable marker gene. Alternatively, the additional gene(s) can be provided on multiple expression cassettes. Such an expression cassette is provided with a plurality of restriction sites for insertion of the herbicide resistance sequence to be under the transcriptional regulation of the regulatory regions.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the polynucleotide sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, operably linked means that the polynucleotide sequences being linked are contiguous and, where necessary to join two protein coding regions, contiguous and in the same reading frame.

Often, such constructs will also contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. The plant expression cassette can also be engineered to contain an intron, such that mRNA processing of the intron is required for expression.

By "3' untranslated region" is intended a nucleotide sequence located downstream of a coding sequence. Polyadenylation signal sequences (for example, polyadenylated nucleotides) and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence.

Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the herbicide resistance sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the polynucleotides of interest are targeted to the chloroplast for expression. In this manner, where the polynucleotide of interest is not directly inserted into the chloroplast, the expression cassette will additionally contain a polynucleotide encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481. In some embodiments, the polynucleotides of the invention encode a fusion polypeptide comprising an amino-terminal chloroplast transit peptide and the EPSPS enzyme. A "fusion polypeptide" can be generated, for example, by removing the stop codon from the polynucleotide sequence encoding a first polypeptide, then appending the polynucleotide sequence encoding a second polypeptide in frame such that the resulting polynucleotide sequence will then be expressed by a cell as a single polypeptide.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a polynucleotide construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science*, 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. In such processes, glyphosate-resistant polypeptides comprising one or more Class III domains of the present invention may be used as selectable marker.

Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Then molecular and biochemical methods will be used for confirming the presence of the integrated heterologous gene of interest in the genome of transgenic plant.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917, Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of the heterologous gene(s) in the plant genome is confirmed by various methods such as analysis of polynucleotides, proteins and metabolites associated with the integrated gene.

PCR analysis is a rapid method to screen transformed cells, tissue or shoots for the presence of the incorporated gene(s) at the earlier stage before transplanting into the soil (Sambrook and Russell (2001) *Molecular Cloning: A Laboratory Manual*, Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}$p target DNA fragment to confirm the integration of introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the sequence of the invention is then tested by hybridizing the filter to a radioactive probe derived from a GDC, by methods known in the art (Sambrook and Russell, 2001, supra)

Western blot and biochemical assays and the like may be carried out on the transgenic plants to determine the presence of protein encoded by the herbicide resistance gene by standard procedures (Sambrook and Russell, 2001, supra) using antibodies that bind to one or more epitopes present on the herbicide resistance protein.

The present invention is also drawn to methods for identifying an EPSP synthase with glyphosate resistance activity. The methods involve determining whether certain conserved sequence domains are present in the amino acid sequence of an EPSP synthase. The presence of one or more of the domains listed above.

Predicting Protein Function From Sequence

Using the methods of the invention and the identified domains, additional polypeptides (for example, SEQ ID NOS:2, 4, 46 and 48) which confer glyphosate tolerance can be identified. These additional polypeptides can be identified by searching sequence databases containing EPSP synthase sequences, and/or by alignment of polypeptide sequences of EPSP synthase to search for the presence of Class III domains. These polypeptides include known polypeptides as well as newly identified polypeptides. It is understood that some modification of these domains is tolerated in nature without disrupting the glyphosate resistance conferring nature of these domains, and are therefore equivalent to the domains listed herein.

In general, there are four levels of protein structure: the primary structure, which consists of the linear chain of amino acids, or the polypeptide sequence; the secondary structure, which is given by the α-helices, β-strands, and turns that the protein folds into; the tertiary structure, which is made up of simple motifs that have combined to form compact globular domains; and the quaternary structure, which can comprise several amino acid chains or subunits. When predicting function from sequence, it is important to identify the functionally important motifs or patterns. Protein domains with similar folds often share the same molecular function (Hegyi and Gerstein (1999) *J. Mol. Biol.* 288:147-164; Moult and Melamud (2000) *Curr. Opin. Struct. Biol.* 10:384-389; Shakhnovich et al. (2003) *J. Mol. Biol.* 326:1-9). Identification of domains important to protein function can be done by multiple sequence alignment.

Three-dimensional structure can be predicted by homology modeling, i.e., by using a sequence homologue (>25% sequence identity) with an experimentally determined 3D structure. The three-dimensional structure of, for example, *E. coli* EPSP synthase (AroA) is well known (Shönbrunn et al. (2001) *Proc. Natl. Acad. Sci. USA* 98:1375-1380). This structure is based on the crystallization of AroA with glyphosate and shikimate 3-phosphate.

The following examples are offered by way of illustration and not by way of limitation.

EXPERIMENTAL

Example 1

Isolation of EPSPS Genes

Genes coding for class III EPSPS enzymes have been isolated from seven different bacteria (*Klebsiella pneumoniae, Agrobacterium radiobacter, Rhizobium* sp., *Brevundomonas vesicularis, Agrobacterium tumefaciens, Pseudomonas syringae*, and *Brucella/Ochrobactrum*).

The DNA coding sequence and the amino acid sequence of the grg8 open reading frame are provided in U.S. Patent Application No. 60/640,195, filed Dec. 29, 2004, and provided in SEQ ID NO:7 and SEQ ID NO:8 of this application, respectively.

The DNA coding sequence and amino acid sequence of the grg12 open reading frame are provided in SEQ ID NOS:57 and 10 and SEQ ID NOS:58 and 59 of this application, respectively.

The DNA coding sequence and amino acid sequence of the grg15 open reading frame are provided in SEQ ID NO:11 and SEQ ID NO:12 of this application, respectively.

The DNA coding sequence and amino acid sequence of the grg6 open reading frame are provided in GenBank Accession Number AE016853, bases 1,140,091 through 1,141,347, and provided in SEQ ID NO:1 and SEQ ID NO:2 of this application, respectively.

The DNA coding sequence and amino acid sequence of the grg9 open reading frame are provided in GenBank Accession Number NC_003304 bases 628,398 through 629,675, and provided in SEQ ID NO:3 and SEQ ID NO:4 of this application, respectively.

The DNA coding sequence and amino acid sequence of the grg7 open reading frame are provided in SEQ ID NO:45, and SEQ ID NO:46 of this application, respectively.

The DNA coding sequence and amino acid sequence of the grg5 open reading frame are provided in GenBank Accession Number NC_005773, bases 1 through 1257, and provided in SEQ ID NO:47 and SEQ ID NO:48 of this application, respectively.

The DNA coding sequence and amino acid sequence of the maize EPSPS open reading frame are provided in GenBank Accession Number X63374 (gi:1524383), bases 1 through 1335, and the protein sequence is provided in SEQ ID NO:50 of this application.

The DNA coding sequence and amino acid sequence of a bacterial EPSPS disclosed in International Patent Application WO2005014820 are provided in SEQ ID NO:53 and SEQ ID NO:54 of this application, respectively.

The DNA coding sequence and amino acid sequence of the grg7m1 open reading frame are provided in SEQ ID NO:55 and SEQ ID NO:56 of this application, respectively.

Example 2

Cloning the EPSP Synthase Gene From *Pseudomonas syringae* pv Tomato Strain DC3000

The EPSP synthase coding sequence was PCR-amplified from genomic DNA of *Pseudomonas syringae* pv. tomato strain DC3000 (ATCC BAA-871) using the following primers: CAGAGATCTGGCATGCGACCTCAAGCCACTCTC (upper, SEQ ID NO:61) and CAGGGCGCGCCT- CAGCGCTGAACACTCACCC (lower, SEQ ID NO:62). The resultant 1.3 kb PCR product was digested with Bgl II and Asc I, ligated into modified pUC18 which had been digested with BamH I and Asc I, then electroporated into DH5α cells. Plasmid DNA was prepared from ampicillin resistant colonies and analyzed by restriction digest. One clone was chosen for further analysis. The DNA sequence of the insert was determined using techniques well known in the art and found to be 100% identical to the published sequence for strain DC3000 (Genbank accession number AE016853 bases 1,140,091 through 1,141,347). This plasmid was named pAX703, and the EPSPS ORF was named grg6.

Plasmid pAX703 was transformed into ΔaroA E. coli cells and found to complement the deletion. This demonstrated that grg6 encodes a functional EPSP synthase.

Example 3

Cloning the EPSP Synthase Gene From Agrobacterium radiobacter Strain C58

The EPSP synthase coding sequence was PCR-amplified from genomic DNA of Agrobacterium tumefaciens strain C58 (ATCC 33970) using the following primers: CAGGGATCCGGCATGATCGAACTGACCATCACCC (upper, SEQ ID NO:63) and CAGGGCGCGCCTCAGTGCTGCGGCTCGGCAGCG (lower, SEQ ID NO:64). The resultant 1.3 kb PCR product was digested with BamH I and Asc I, ligated into modified pUC18 which had been digested with BamH I and Asc I, then electroporated into DH5α cells. Plasmid DNA was prepared from ampicillin resistant colonies and analyzed by restriction digest. One clone was chosen for further analysis. The DNA sequence of the insert was determined using techniques well known in the art and found to be 100% identical to the published sequence for strain C58 (Genbank accession number NC_003304 bases 628398 through 629675). This plasmid was named pAX702, and the C58 EPSPS ORF was named grg9.

Plasmid pAX702 was transformed into ΔaroA E. coli cells and found to complement the deletion. This demonstrated that grg9 encodes a functional EPSP synthase.

Example 4

Testing grg6 and grg9 for Resistance to Glyphosate

Plasmids pAX703 and pAX702, containing grg6 and grg9, respectively, were transformed into E. coli cells and streaked onto M63 agar medium containing various concentrations of glyphosate. The vector plasmid pUC18 was used as a glyphosate-sensitive control. The results are presented in Table 1 below and demonstrate that expression of grg6 or grg9, confers resistance to high levels of glyphosate.

TABLE 1

Growth of E. coli expressing grg6 or grg9 in the presence of glyphosate.

| | | Glyphosate Concentration | | |
|---|---|---|---|---|
| Plasmid | Gene | 0 mM | 50 mM | 100 mM |
| pUC18 | (none) | ++ | − | − |
| pAX703 | grg6 | ++ | ++ | ++ |
| pAX702 | grg9 | ++ | ++ | ++ |

Example 5

Cloning the EPSP Synthase Gene from Pseudomonas syringae pv syrinaae Strain B728a The EPSP synthase coding sequence was PCR-amplified from a single well isolated colony of Pseudomonas syringae pv syringae strain B728a using the following primers: CAGGGATCCGGCATGCGACCTCAAGCCACCCTC (upper, SEQ ID NO:65) and CAGGGCGCGCCTCAGCGCTGAACACTCACAC (lower, SEQ ID NO:66). The resultant 1.26 kb PCR product was digested with appropriate restriction enzymes and ligated into the vector pRSF1b, then electroporated into E. coli cells. Plasmid DNA was prepared from ampicillin resistant colonies and analyzed by restriction digest. One clone was chosen for further analysis and designated as pAX1923. The DNA sequence of the open reading frame in pAX1923 was determined and found to be identical to the published sequence of the EPSPS from Pseudomonas syringae pv. syringae strain B728a. Thus, we designated this open reading frame as grg7.

Similarly, a separate 1.26 kb PCR product was digested with BamH I and Asc I, ligated into modified pUC18 which had been digested with BamH I and Asc I, then electroporated into DH5α cells. Plasmid DNA was prepared from ampicillin resistant colonies and analyzed by restriction digest. One clone was chosen for further analysis. The DNA sequence of the insert of pAX712 was determined using techniques well known in the art and found to contain 3 nucleotide changes when compared to the published DNA sequence of Pseudomonas syringae pv syringae strain B728a (Genbank Accession Number NZ_AABP02000003, bases 39,901 through 41,400). These three DNA nucleotide changes result in a protein with one amino acid change relative to the hypothetical protein encoded by the published sequence. The open reading frame from strain B728a encoding an EPSPS as identified in plasmid pAX712 was designated grg7m1 (SEQ ID NO:55; grg7m1 protein sequence set forth in SEQ ID NO:56).

Example 6

Cloning the EPSP Synthase Gene from Pseudomonas syringae pv phaseolicola strain 1448a Sequence data for the EPSPS of Pseudomonas syringae pv phaseolicola strain 1448a was obtained from The Institute for Genomic Research website at www.tigr.org. The EPSP synthase coding sequence of Pseudomonas syringae pv phaseolicola strain 1448a was PCR-amplified from genomic DNA of Pseudomonas syringae pv phaseolicola strain 1448a (ATCC BAA-978) using the following primers: CAGGGATCCGGCATGCGACCTCAAGCCACCCTC (upper, SEQ ID NO:67) and AGAGGCGCGCCTCAGCGCTGAACACGCACC (lower, SEQ ID NO:68), designed based on the DNA sequence available from The Institute for Genomic Research ("TIGR", personal communication). The resultant 1.26 kb PCR product was digested with BamH I and Asc I, ligated into modified pUC 18 which had been digested with BamH I and Asc I, then electroporated into DH5α cells. Plasmid DNA was prepared from ampicillin resistant colonies and analyzed by restriction digest. One clone was chosen for further analysis, and designated pAX713. The DNA sequence of the insert of pAX713 was determined using techniques well known in the art and found to be 100% identical to the published DNA sequence of Pseudomnonas syringae pv. phaseolicola strain 1448a (performed by The Institute for Genomic Research (TIGR), and available online in electronic form at www.tigr.org). This plasmid was named pAX713, and the open reading frame from strain 1448a encoding an EPSPS as identified in plasmid pAX713 was designated grg5.

Example 7

Testing of grg5 and grg7 for Resistance to Glyphosate

Plasmids pAX713, pAX1923, and pAX712, containing grg5, grg7, and grg7m1, respectively, were transformed into E. coli cells and streaked onto M63 agar medium containing various concentrations of glyphosate. The vector plasmid pUC18 was used as a glyphosate-sensitive control. The results are presented in Table 2 below and demonstrate that expression of grg5, grg7, or grg7m1 confers resistance to high levels of glyphosate.

TABLE 2

Growth of E. coli expressing grg5, grg7, or grg7m1 in the presence of glyphosate.

| Plasmid | Gene | Glyphosate Concentration | | |
|---------|------|---------|---------|---------|
|         |      | 0 mM    | 50 mM   | 100 mM  |
| pUC18   | (none) | ++    | −       | −       |
| pAX713  | grg5 | ++      | ++      | ++      |
| pAX1923 | grg7 | ++      | ++      | ++      |
| pAX712  | grg7m1 | ++    | ++      | ++      |

Example 8

Isolation of ATX20019

ATX20019 was isolated by plating samples of soil on HEPES Mineral Salts Medium (HMSM) containing glyphosate as the sole source of phosphorus. Since HMSM contains no aromatic amino acids, a strain must be resistant to glyphosate in order to grow on this media.

Two grams of soil were suspended in approximately 10 ml of water, vortexed for 15 seconds and permitted to settle for 15 minutes. A 10 µl loopful of this suspension was added to 3 ml of HMSM supplemented with 10 mM glyphosate (pH 7.0). HMSM contains (per liter): 10 g glucose, 2 g $NH_4SO_4$, 9.53 g HEPES, 1.0 ml 0.8 M $MgSO_4$, 1.0 ml 0.1 M $CaCl_2$, 1.0 ml Trace Elements Solution (In 100 ml of 1000× solution: 0.1 g $FeSO_4 \cdot 7H_2O$, 0.5 mg $CuSO_4 \cdot 5H_2O$, 1.0 mg $H_3BO_3$, 1.0 mg $MnSO_4 \cdot 5H_2O$, 7.0 mg $ZnSO_4 \cdot 7H_2O$, 1.0 mg $MoO_3$, 4.0 g KCl). The culture was grown in a shaker incubator for four days at 28° C. and then 20 µl was used to inoculate 2.5 ml of fresh HMSM containing 10 mM glyphosate as the only phosphorus source. After two days, 20 µl was used to inoculate another fresh 2.5 ml culture. After 5 days, 20 µl was used to inoculate a fresh 2.5 ml culture. After sufficient growth, the culture was plated onto solid media by streaking a 1 µl loop onto the surface of agar plate containing HMSM agar containing 10 mM glyphosate as the sole phosphorus source and stored at 28° C. The culture was then replated for isolation. One particular strain, designated ATX20019, was selected due to its ability to grow in the presence of high glyphosate concentrations. ATX 20019 was determined to be a member of Ochrobactrum sp./Brucella sp. by sequencing of the 16S rDNA and comparison against a database.

Example 9

Preparation and Screening of Cosmid Libraries

Total DNA was extracted from a culture of ATX20019 using methods commonly known in the art. The DNA was partially digested with restriction enzyme Sau3A1 and ligated with SuperCos (Stratagene) vector fragment according to the manufacturer's directions. Ligation products were packaged into phage particles using GigaPack III XL packaging extract (Stratagene), transfected into E. coli aroA-cells. E. coli aroA- is a strain in which the native aroA gene, encoding EPSP synthase, has been deleted. This strain cannot grow on M63 medium because it requires exogenously supplied aromatic amino acids. The presence of a cosmid which contains an EPSP synthase gene can genetically complement the aroA-phenotype, that is, allow the strain to grow on M63 medium without exogenously supplied aromatic amino acids.

The transfected cells were plated on M63 agar medium containing 50 µg/ml kanamycin M63 agar medium containing 100 mM $KH_2PO_4$, 15 mM $(NH_4)_2SO_4$, 50 µM $CaCl_2$, 1 µM $FeSO_4$, 50 µM $MgCl_2$, 55 mM glucose, 25 mg/liter L-proline, 10 mg/liter thiamine HCl, sufficient NaOH to adjust the pH to 7.0, and 15 g/liter agar. Two colonies which grew on this medium were identified. Cosmid DNA was prepared from each of these colonies and re-transformed into E. coli aroA-cells. In each case, cells retransformed with cosmid DNA grew on M63 medium in the presence of 0 or 10 mM glyphosate while cells containing empty SuperCos vector did not. This confirms that the cosmids are able to complement the aroA-phenotype and able to confer resistance to glyphosate. These cosmids were named pAX1100 and pAX1101. The cosmids appeared to be identical by restriction digest analysis using two different enzymes. One cosmid, pAX1101, was selected for further characterization.

Example 10

Identification of grg12 in Cosmid pAX1101

To identify the gene(s) responsible for the glyphosate-resistance shown by cosmid pAX1101, DNA from this clone was mutagenized with transposable elements. In this method, one identifies clones that have suffered transposon insertions, and have lost the ability to confer glyphosate resistance. The location of the transposon insertions identifies the open reading frame responsible for the glyphosate resistance phenotype.

Cosmid pAX1101 was subjected to in vitro transposon mutagenesis using an EZ::TN Insertion Kit (Epicentre, Madison, Wis.) and the manufacturer's protocol. This process randomly inserts a transposon fragment into the cosmid DNA and thus randomly disrupts the function of genes in the cosmid. The transposons contain a gene encoding resistance to an antibiotic, so transposon insertion clones may be selected by the ability to grow in the presence of that antibiotic. The locations of the transposon insertions may be determined by restriction fragment mapping or by sequencing with primers which anneal in the transposon.

Transposon insertion clones of pAX1101 were transformed into E. coli strain DH5α and plated on M63 medium containing glyphosate. Multiple clones were found which had lost the ability to grow in the presence of glyphosate, indicating that the transposon had disrupted the gene responsible for resistance.

The DNA sequence was determined for the region of pAX1101 containing the transposon insertions using sequencing methods well known in the art and is presented as SEQ ID NO:9. An open reading frame (ORF) was identified at bases 46 through 1380 of SEQ ID NO:9. This nucleotide sequence is provided as SEQ ID NO:57, and the corresponding amino acid sequence is provided as SEQ ID NO:58. Analysis of sequence data from eight transposon insertion picks that had lost resistance to glyphosate revealed that all were within the ORF. This indicates that the ORF encodes the resistance to glyphosate conferred by the cosmid. This gene was named grg12. Cosmid pAX1101 containing the grg12 ORF was deposited at the Agricultural Research Service Culture Collection (NRRL) Apr. 4, 2005, and assigned Accession No. B-30833.

Example 11

Homology of GRG12 With Other Proteins

Figure 1A:
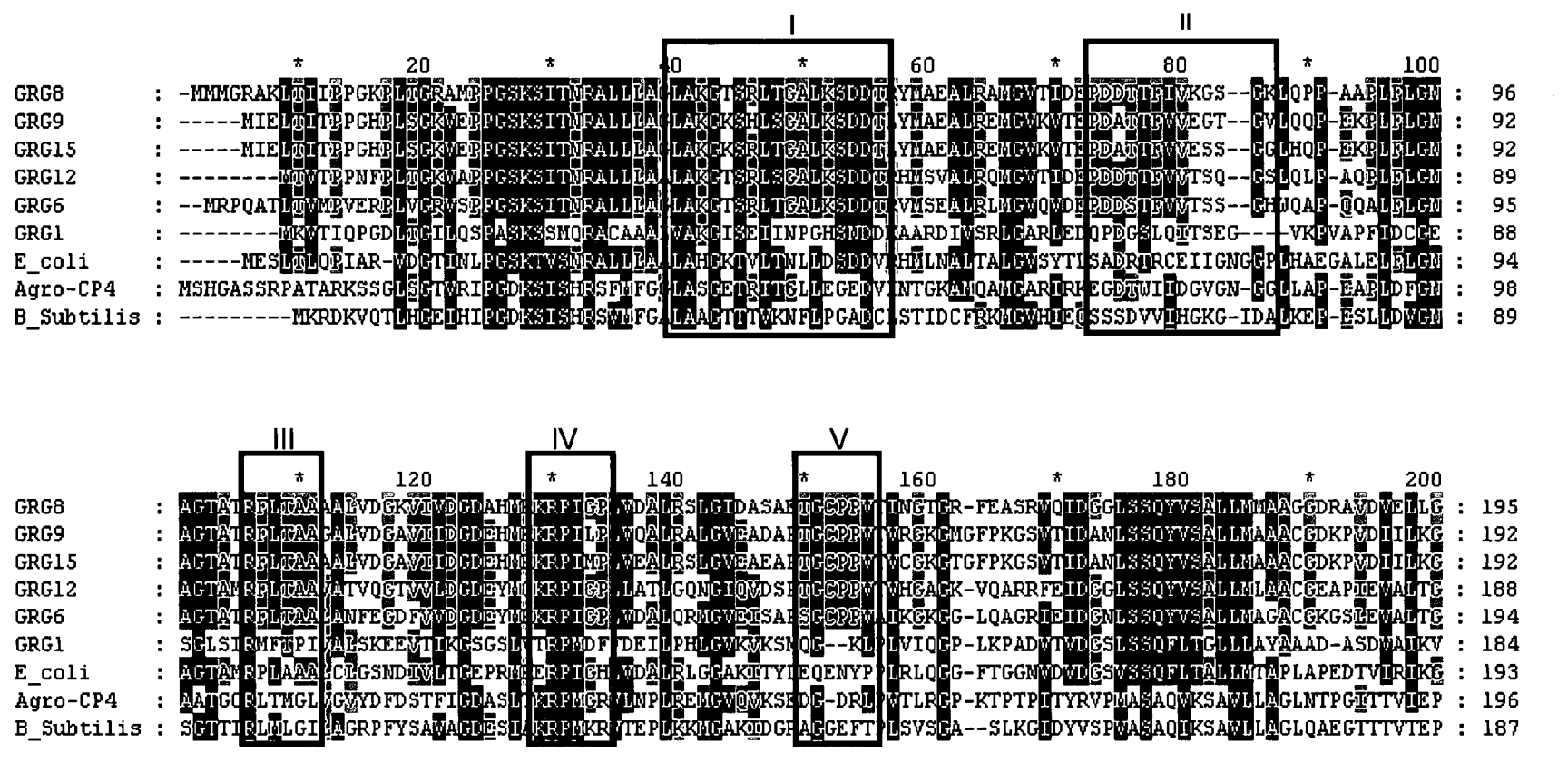
Figure 1B:
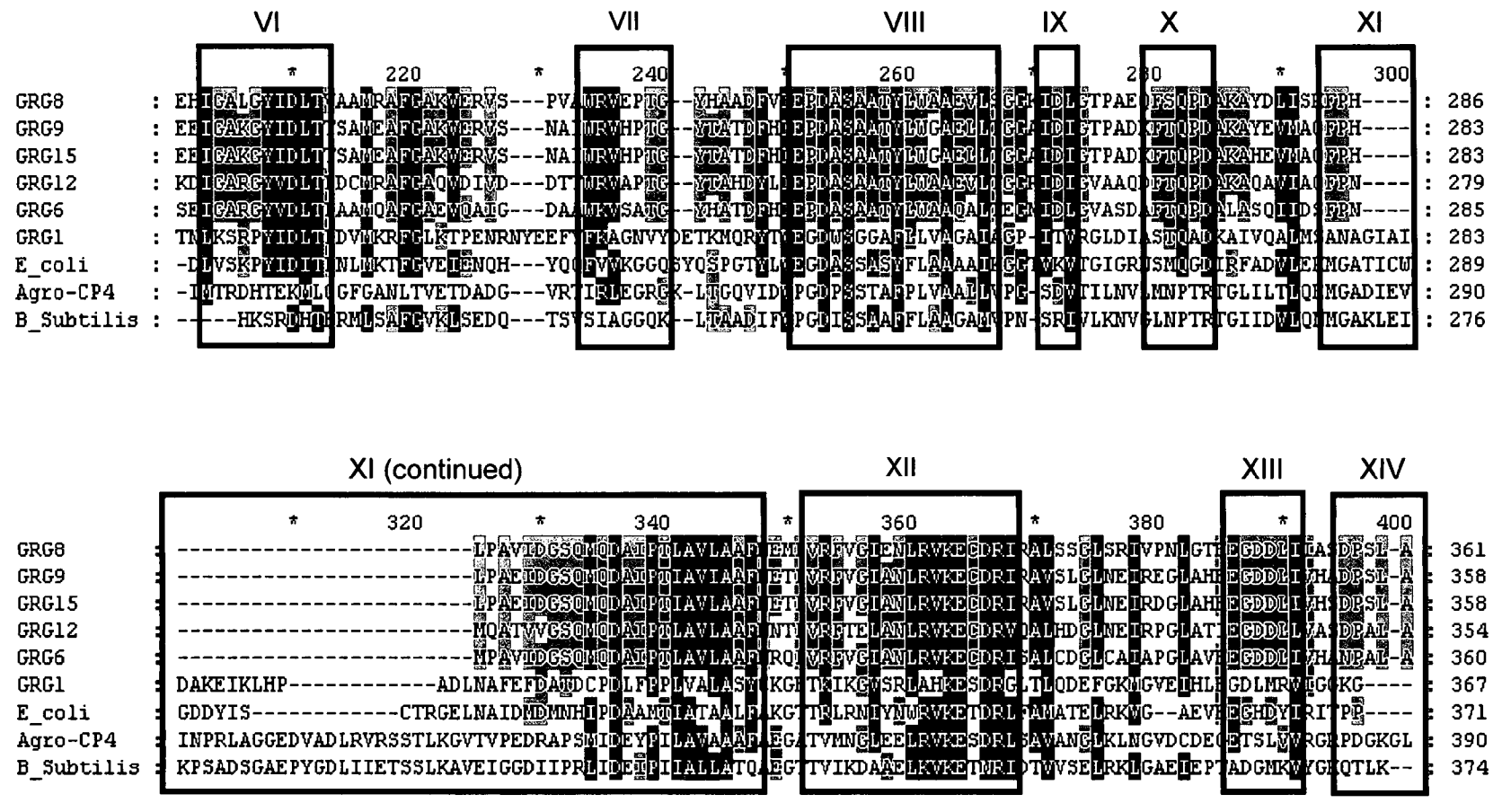
Figure 1C:
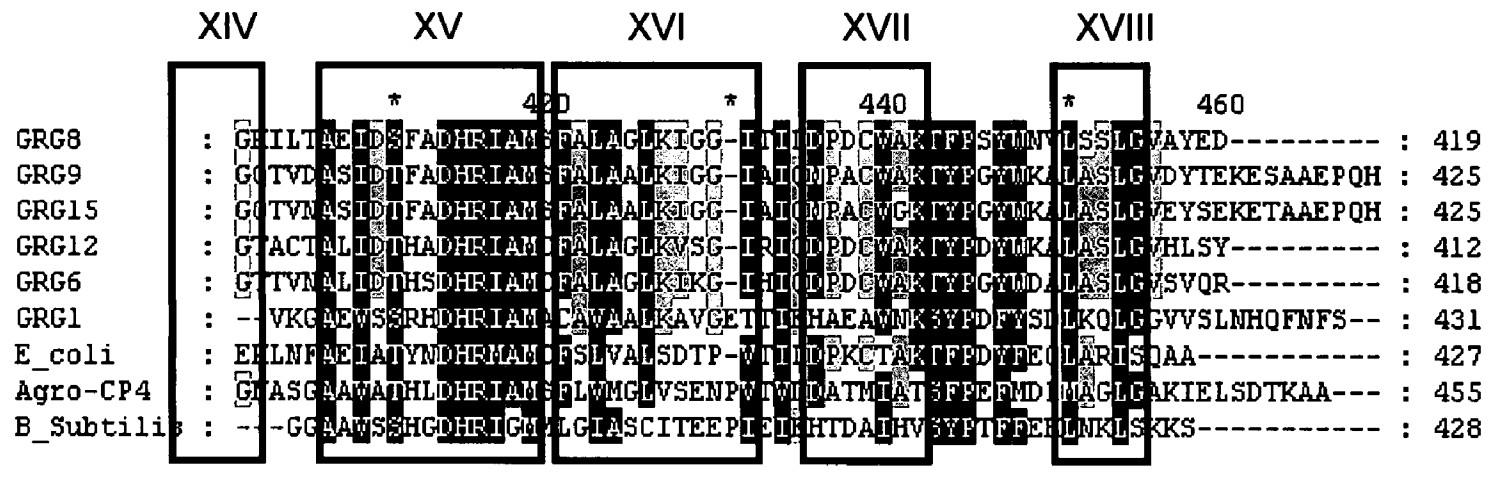

GRG12 has homology to EPSP synthase enzymes. An alignment of the GRG12 amino acid sequence (SEQ ID NO:10) with the amino acid sequences of other EPSP synthases is shown in FIG. 1. Table 3 lists the percent identity of GRG12 to various EPSP synthases. Examination of the amino acid sequence (SEQ ID NO:10) revealed that it does not contain the four domains typical of Class II EPSP synthase enzymes. Thus it is a novel, non-Class II, glyphosate-resistant EPSP synthase.

GRG12 has highest amino acid homology to an EPSPS described in WO2005014820 (SEQ ID NO:54). GRG12 (SEQ ID NO:10) has 92% amino acid identity to the EPSPS described in WO2005014820.

TABLE 3

Amino Acid Identity of GRG12 to Other EPSP Synthases

| Gene | Percent Identity to GRG12 |
| --- | --- |
| GRG8 | 61% |
| GRG7 | 65% |
| GRG6 | 65% |
| GRG9 | 60% |
| D. psychrophila | 32% |
| K. pneumoniae | 31% |
| E. coli | 30% |
| H. influenzae | 30% |
| A. fulgidus | 22% |
| CP4 | 22% |
| A. pernix | 21% |
| C. perfringens | 21% |
| B. subtilis | 17% |
| WO2005014820 | 92% |

Further analysis of the grg12 DNA sequence (SEQ ID NO:9) revealed the presence of a second, shorter open reading frame (SEQ ID NO:58) beginning with a GTG start codon at nucleotide 142 of SEQ ID NO:9. Translation of this open reading frame results in a protein (SEQ ID NO:59) that is identical to residues 33-444 of SEQ ID NO:10, except that the start codon of SEQ ID NO:59 is a methionine instead of the valine present in SEQ ID NO:10. Alignment of SEQ ID NO:59 with known EPSPS proteins indicated that this protein contains all residues known to be critical to function as an EPSPS. Thus, this protein is likely to comprise a functional, glyphosate-resistant EPSPS enzyme, whereas a protein resulting from initiation of translation from a start codon internal to the highly conserved domains would be unlikely to be functional. SEQ ID NO:59 is 97% identical to the EPSPS described in WO2005014820 (SEQ ID NO:54).

The ability of both open reading frames (SEQ ID NOS:57 and 58) to encode functional EPSPS activity may be tested by amplifying each open reading frame by PCR, cloning the resulting PCR fragments into a plasmid vector under the control of a suitable promoter, inducing expression of protein from the open reading frame as known in the art, and comparing the ability of the expressed protein to complement the aroA-phenotype in *E. coli* and to confer resistance to glyphosate.

Example 12

Engineering of grg12 for Expression of GRG12 Protein in *E. coli*

The grg12 open reading frame (ORF) was amplified by PCR, cloned into a slightly modified version of the plasmid vector pUC18 and transformed into *E. coli* strain DH5α. The modifications to pUC18 were as follows: a stop codon was inserted into the lacZ open reading frame and a ribosome binding site (to optimize translational initiation of the inserted grg12 ORF) was inserted upstream of the BamHI restriction site. Plasmid DNA was prepared and the presence and orientation of the grg12 insert was determined by restriction digest. One clone which contained the ORF in the forward orientation with respect to the lac promoter in the vector was named pAX1106 and was tested for the ability to confer resistance to glyphosate. *E. coli* cells harboring pAX1106 or empty vector plasmid were streaked onto M63 agar plates containing 0 to 200 mM glyphosate. The results are presented in Table 4 below. These results demonstrate that grg12 confers resistance to high levels of glyphosate.

TABLE 4

Growth of pAX1106 on M63 Glyphosate Agar

| Glyphosate Concentration (mM) | pAX1106 | Empty Vector |
| --- | --- | --- |
| 0 | + | + |
| 50 | + | − |
| 100 | + | − |
| 200 | + | − |

Example 13

Purification of GRG12 Expressed as a 6×His-Tagged Protein in *E. coli*

The grg12 coding region is amplified by PCR using PFUULTRA™ DNA polymerase (Stratagene). Oligonucleotides used to prime PCR are designed to introduce restriction enzyme recognition sites near the 5' and 3' ends of the resulting PCR product. The resulting PCR product is digested with appropriate restriction enzymes and the digested product is cloned into the 6×His-tag expression vector pRSF1b (Novagen). The resulting clone contains grg12 in the same translational reading frame as, and immediately C-terminal to, the 6×His tag. General strategies for generating such clones, and for expressing proteins containing 6×His-tag are well known in the art. The level of expression of GRG12 protein may be determined on an SDS-PAGE protein gel. GRG12 protein can be isolated by purification of the induced GRG12 protein by chromatography on, for example, Ni-NTA Superflow Resin (Qiagen), as per manufacturer's instructions.

Example 14

Isolation of ATX4150

ATX4150 was isolated by plating samples of soil on Enriched Minimal Media (EMM) containing glyphosate as the sole source of phosphorus. Since EMM contains no aromatic amino acids, a strain must be resistant to glyphosate in order to grow on this media.

Two grams of soil were suspended in approximately 30 ml of water, and sonicated for 30 seconds in an Aquasonic sonicator water bath. The sample was vortexed for 5 seconds and permitted to settle for 60 seconds. This process was repeated 3 times. 100 μl of this suspension was added to 3 ml of EMM supplemented with 4 mM glyphosate (pH 6.0). EMM contains (per 900 mls): 10 g sucrose, 2 g $NaNO_3$, 1.0 ml 0.8 M $MgSO_4$, 1.0 ml 0.1 M $CaCl_2$, 1.0 ml Trace Elements Solution (In 100 ml of 1000× solution: 0.1 g $FeSO_4.7H_2O$, 0.5 mg $CuSO_4.5H_2O$, 1.0 mg $H_3BO_3$, 1.0 mg $MnSO_4.5H_2O$, 7.0 mg $ZnSO_4.7H_2O$, 1.0 mg $MoO_3$, 4.0 g KCl). The culture was shaken on a tissue culture roller drum for sixteen days at 21° C. and then 100 μl was used to inoculate 3 ml of fresh EMM containing 4 mM glyphosate as the only phosphorus source. After five days, 100 μl was used to inoculate another fresh 3 ml culture. After a few days, the culture was plated onto solid media by streaking a 1 μl loop onto the surface of agar plate containing EMM agar containing 5 mM glyphosate as the sole phosphorus source. After a few days, colonies were replated for isolation onto EMM containing 5 mM glyphosate as the sole phosphorus source. One particular strain, designated ATX4150, was selected due to its ability to grow in the presence of high glyphosate concentrations.

Example 15

Preparation and Screening of Cosmid Libraries

Total DNA was extracted from a culture of ATX4150 using methods commonly known in the art. The DNA was partially digested with restriction enzyme Sau3A1 and ligated with SuperCos (Stratagene) vector fragment according to the manufacturer's directions. Ligation products were packaged into phage particles using GigaPack III XL packaging extract (Stratagene), transfected into E. coli aroA-cells E. coli aroA-, is a strain in which the native aroA gene, encoding EPSP synthase, has been deleted. This strain cannot grow on M63 medium because it requires exogenously supplied aromatic amino acids. The presence of a cosmid which contains an EPSP synthase gene can genetically complement the aroA-phenotype, that is, it allow the strain to grow on M63 medium without exogenously supplied aromatic amino acids.

The transfected cells were plated on M63 agar medium containing 50 μg/ml kanamycin M63 agar medium contains 100 mM $KH_2PO_4$, 15 mM $(NH_4)_2SO_4$, 50 μM $CaCl_2$, 1 μM $FeSO_4$, 50 μM $MgCl_2$, 55 mM glucose, 25 mg/liter L-proline, 10 mg/liter thiamine HCl, sufficient NaOH to adjust the pH to 7.0, and 15 g/liter agar. Five colonies which grew on this medium were identified. Cosmid DNA was prepared from each of these colonies and re-transformed into E. coli aroA-cells. In each case cells retransformed with cosmid DNA grew on M63 medium in the presence of 0 or 10 mM glyphosate while cells containing empty SuperCos vector did not. This confirms that the cosmids are able to complement the aroA-phenotype and able to confer resistance to glyphosate. One cosmid was selected for further characterization and was named pAX305.

Example 16

Identification of grg15 in Cosmid pAX305

To identify the gene(s) responsible for the glyphosate-resistance shown by cosmid pAX305, DNA from this clone was mutagenized with transposable elements. Cosmid pAX305 was subjected to in vitro transposon mutagenesis using an EZ::TN Insertion Kit (Epicentre, Madison, Wis.) and the manufacturer's protocol. Transposon insertion clones of pAX305 were transformed into E. coli and plated on M63 medium containing glyphosate. Multiple clones were found which had lost the ability to grow in the presence of glyphosate, indicating that the transposon had disrupted the gene responsible for resistance.

The DNA sequence was determined for the region of pAX305 containing the transposon insertions using sequencing methods well known in the art and is presented in SEQ ID NO:61. An open reading frame (ORF, nucleotide bases 77 through 1354 of SEQ ID NO:61) was identified. Analysis of sequence data from eight transposon insertion picks that had lost resistance to glyphosate revealed that all were within the ORF. This indicates that the ORF encodes the resistance to glyphosate conferred by the cosmid. This gene was named grg15. Cosmid pAX305 containing the grg15 ORF (SEQ ID NO:11) was deposited at the Agricultural Research Service Culture Collection (NRRL) on Apr. 20, 2005 and assigned Accession No. NRRL B-30838.

Example 17

Homology of GRG15 With Other Proteins

GRG15 has homology to EPSP synthase enzymes. An alignment of the GRG15 amino acid sequence (SEQ ID NO:12) with the amino acid sequences of other EPSP synthases is shown in FIG. 1. Table 5 lists the percent identity of GRG15 to various EPSP synthases. Examination of the amino acid sequence (SEQ ID NO:12) revealed that it does not contain the four domains typical of Class II EPSP synthase enzymes. Thus it is a novel, non-Class II, glyphosate-resistant EPSP synthase.

TABLE 5

Amino Acid Identity of GRG15 to Other EPSP Synthases

| Gene | Percent Identity to GRG15 |
|---|---|
| GRG9 | 94% |
| GRG8 | 70% |
| GRG7 | 66% |
| GRG6 | 66% |
| GRG12 | 60% |
| K. pneumoniae | 32% |
| E. coli | 32% |
| H. influenzae | 32% |
| D. psychrophila | 31% |
| A. fulgidus | 26% |
| A. pernix | 26% |
| C. perfringens | 24% |
| B. subtilis | 24% |
| GRG1 | 23% |
| Agrobacterium Sp. CP4 | 22% |

Example 18

Homology Blocks Among Glyphosate Resistant Non-Class II Enzymes (Class III)

Comparison of the amino acid sequences of the GRG proteins (non-class II glyphosate resistant proteins) show that the GRG proteins have significant homology to one another, and are distinct from previously identified glyphosate resistant EPSP synthases (see FIG. 1).

Example 19

Identification of Conserved Domains

The amino acid sequences of seven known EPSP synthases were analyzed for conserved domains that were not present in either class I or class II EPSP synthases. The following domains are found in these EPSP synthases: Bold type denotes conserved residues only among this class, and italics denote residues conserved in all EPSPS enzymes.

Domain I:

L-A-K-G-$X_1$-S-$X_2$-L-$X_3$-G-A-L-K-S-D-D-T (SEQ ID NO:13), where $X_1$ denotes lysine or threonine, where $X_2$ denotes arginine or histidine, where $X_3$ denotes serine or threonine.

Domain Ia:

L-A-K-G-$X_1$, (SEQ ID NO:14), where $X_1$ denotes lysine or threonine.

Domain Ib:

S-$X_1$-L-$X_2$ (SEQ ID NO:15), where $X_1$ denotes arginine or histidine, where $X_2$ denotes serine or threonine.

Domain Ic:

```
G-A-L-K-S-D-D-T        (SEQ ID NO: 16)
```

Domain II:

E-P-D-$X_1$-$X_2$-T-F-$X_3$-V-$X_4$-$X_5$-$X_6$-G (SEQ ID NO: 17), where $X_1$ denotes aspartic acid or alanine, where $X_2$ denotes serine or threonine, where $X_3$ denotes valine or isoleucine, where $X_4$ denotes threonine or glutamic acid or lysine, where $X_5$ denotes serine or glycine, where $X_6$ denotes glutamine or serine or glutamic acid or threonine.

Domain IIa:

E-P-D-$X_1$-$X_2$-T-F-$X_3$-V (SEQ ID NO:18), where $X_1$ denotes aspartic acid or alanine, where $X_2$ denotes serine or threonine, where $X_3$ denotes valine or isoleucine.

Domain IIb:

$X_1$-$X_2$-$X_3$-G (SEQ ID NO:19), where $X_1$ denotes threonine or glutamic acid or lysine, where $X_2$ denotes serine or glycine, where $X_3$ denotes glutamine or serine or glutamic acid or threonine.

Domain III:

```
RFLTAA          (SEQ ID NO: 20)
```

Domain IV:

KRPI(G/M)P (SEQ ID NO:21)

K-R-P-I-$X_1$-P, where $X_1$ denotes glycine or methionine or leucine.

Domain V:

$X_1$-G-C-P-P-V (SEQ ID NO:22), where $X_1$ denotes threonine or serine.

Domain VI:

I-G-A-$X_1$-G-Y-$X_2$-D-L-T (SEQ ID NO:23), where $X_1$ denotes arginine or lysine or leucine, and where $X_2$ denotes isoleucine or valine.

Domain VII:

W-$X_1$-V-$X_2$-$X_3$-T-G (SEQ ID NO:24), where $X_1$ denotes arginine or lysine, where $X_2$ denotes alanine or histidine or glutamic acid or serine, where $X_3$ denotes proline or alanine.

Domain VIII:

E-P-D-A-S-A-A-T-Y-L-W-$X_1$-A-$X_2$-$X_3$-L (SEQ ID NO:25), where $X_1$ denotes alanine or glycine, where $X_2$ denotes glutamic acid or glutamine, where $X_3$ denotes valine or leucine or alanine.

Domain VIIIa:

```
E-P-D-A-S-A-A-T-Y-L-W    (SEQ ID NO: 26)
```

Domain IX:

I-D-$X_1$-G (SEQ ID NO:27), where $X_1$ denotes isoleucine or leucine.

Domain X:

F-$X_1$-Q-P-D-A-K-A (SEQ ID NO:28), where $X_1$ denotes threonine or serine,

Domain XI:

$X_1$-F-P-$X_2$-$X_3$-$X_4$-A-$X_5$-$X_6$-$X_7$-G-S-Q-M-Q-D-A-I-P-T-$X_8$-A-V-$X_9$A-A-F-N (SEQ ID NO:29), where $X_1$ denotes glutamine or lysine or serine, where $X_2$ denotes asparagine or histidine, where $X_3$ denotes methionine or leucine, where $X_4$ denotes proline or glutamine, where $X_5$ denotes threonine or glutamic acid or valine, where $X_6$ denotes valine or isoleucine, where $X_7$ denotes aspartic acid or valine, where $X_8$ denotes leucine or isoleucine, where $X_9$ denotes leucine or isoleucine.

Domain XIa:

$X_1$-F-P-$X_2$-$X_3$-$X_4$-A (SEQ ID NO:30), where $X_1$ denotes glutamine or lysine or serine, where $X_2$ denotes asparagine or histidine, where $X_3$ denotes methionine or leucine, where $X_4$ denotes proline or glutamine.

Domain XIb:

$X_1$-$X_2$-$X_3$-G-S-Q-M-Q-D-A-I-P-T-$X_4$-A-V-$X_5$A-A-F-N (SEQ ID NO:31), where $X_1$ denotes threonine or glutamic acid or valine, where $X_2$ denotes valine or isoleucine, where $X_3$ denotes aspartic acid or valine, where $X_4$ denotes leucine or isoleucine, where $X_5$ denotes leucine or isoleucine.

Domain XIc:

```
G-S-Q-M-Q-D-A-I-P-T      (SEQ ID NO: 32)
```

Domain XII:

P-V-R-F-$X_1$-$X_2$-$X_3$-$Y_4$-N-L-R-V-K-E-C-D-R-$X_5$ (SEQ ID NO:33), where $X_1$ denotes valine or threonine, where $X_2$ denotes glutamic acid or glycine, where $X_3$ denotes leucine or isoleucine, where $X_4$ denotes alanine or glutamic acid, where $X_5$ denotes isoleucine or valine.

Domain XIIa:

```
          P-V-R-F           (SEQ ID NO: 34)
```

Domain XIIb:

$X_1$-$X_2$-$X_3$-$X_4$-N-L-R-V-K-E-C-D-R-$X_5$ (SEQ ID NO:35), where $X_1$ denotes valine or threonine, where $X_2$ denotes glutamic acid or glycine, where $X_3$ denotes leucine or isoleucine, where $X_4$ denotes alanine or glutamic acid, where $X_5$ denotes isoleucine or valine.

Domain XIIc:

```
       N-L-R-V-K-E-C-D-R       (SEQ ID NO: 36)
```

Domain XIII:

E-G-D-D-L-$X_1$-$X_2$ (SEQ ID NO:37), where $X_1$ denotes leucine or isoleucine, where $X_2$ denotes valine or isoleucine.

Domain XIV:

$X_1$-P-$X_2$-L-A-G (SEQ ID NO:38), where $X_1$ denotes aspartic acid or asparagine, where $X_2$ denotes alanine or serine or threonine.

Domain XV:

A-$X_1$-I-D-$X_2$-$X_3$-$X_4$-D-H-R- (SEQ ID NO:39), where $X_1$ denotes leucine or serine or glutamic acid, where $X_2$ denotes threonine or serine, where $X_3$ denotes histidine or phenylalanine, where $X_4$ denotes alanine or serine.

Domain XVI:

F-A-L-A-$X_1$-L-K-$X_2$-$X_3$-G-I (SEQ ID NO:40), where $X_1$ denotes glycine or alanine, where $X_2$ denotes isoleucine or valine, where $X_3$ denotes serine or glycine or alanine or lysine.

Domain XVIa:

F-A-L-A-$X_1$-L-K (SEQ ID NO:41), where $X_1$ denotes glycine or alanine.

Domain XVIb:

L-K-$X_1$-$X_2$-G-I (SEQ ID NO:42), where $X_1$ denotes isoleucine or valine, where $X_2$ denotes serine or glycine or alanine or lysine.

Domain XVII:

-$X_1$-P-$X_2$-C-V-$X_3$-K (SEQ ID NO:43), where $X_1$ denotes asparagine or aspartic acid, where $X_2$ denotes alanine or aspartic acid, where $X_3$ denotes alanine or glycine.

Domain XVIII:

$X_1$-S-L-G-V (SEQ ID NO:44), where $X_1$ denotes alanine or serine or proline.

Example 20

Engineering grg12 for Plant Transformation

The grg12 open reading frame (ORF) is amplified by PCR from a full-length cDNA template. Hind III restriction sites are added to each end of the ORF during PCR. Additionally, the nucleotide sequence ACC is added immediately 5' to the start codon of the gene to increase translational efficiency (Kozak (1987) *Nucleic Acids Research* 15:8125-8148; Joshi (1987) *Nucleic Acids Research* 15:6643-6653). The PCR product is cloned and sequenced, using techniques well known in the art, to ensure that no mutations are introduced during PCR.

The plasmid containing the grg12 PCR product is digested with, for example, Hind III and the fragment containing the intact ORF is isolated. In this example, the fragment is cloned into the Hind III site of a plasmid, such as pAX200, which is a plant expression vector containing the rice actin promoter (McElroy et al. (1991) *Molec. Gen. Genet.* 231:150-160), and the PinII terminator (An et al. (1989) *The Plant Cell* 1:115-122). The promoter—gene—terminator fragment from this intermediate plasmid is then subcloned into a plasmid such as pSB11 (Japan Tobacco, Inc.) to form a final plasmid, referred to herein as pSB11GRG12. pSB11GRG12 is organized such that the DNA fragment containing the promoter—grg12—terminator construct may be excised by appropriate restriction enzymes and also used for transformation into plants, for example, by aerosol beam injection. The structure of pSB11GRG12 is verified by restriction digests and gel electrophoresis and by sequencing across the various cloning junctions.

The plasmid is mobilized into *Agrobacterium tumefaciens* strain LBA4404 which also harbors the plasmid pSB1 (Japan Tobacco, Inc.), using triparental mating procedures well known in the art, and plating on media containing antibiotic. Plasmid pSB11GRG12 carries spectinomycin resistance but is a narrow host range plasmid and cannot replicate in *Agrobacterium*. Antibiotic resistant colonies arise when pSB11GRG12 integrates into the broad host range plasmid pSB1 through homologous recombination. The resulting cointegrate product is verified by Southern hybridization. The *Agrobacterium* strain harboring the cointegrate can be used to transform maize, for example, by the PureIntro method (Japan Tobacco).

Example 21

Transformation of grg12 Into Plant Cells

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express GRG12 in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

TABLE 6

| Components | Per Liter | Source |
|---|---|---|
| DN62A5S Media | | |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 22

Transformation of grg12 Into Maize Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an Agrobacterium strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated polynucleotide encoding a glyphosate tolerant EPSPS enzyme having at least 95% sequence identity to SEQ ID NO:10, 12, or 59.

2. The polynucleotide of claim 1, wherein said polynucleotide is selected from the group consisting of:
   a) the nucleotide sequence of SEQ ID NO:9, 11, 56, 57, 58, or 60;
   b) the herbicide resistance nucleotide sequence of the DNA insert of the plasmid deposited as Accession Nos. B-30833 or B-30838, or a complement thereof and
   c) a nucleotide sequence that encodes a polypeptide comprising the amino acid sequence of SEQ ID NO:10, 12, 56, or 59.

3. The polynucleotide of claim 1, wherein said polynucleotide is linked to a promoter which functions in plant cells to cause the production of an RNA sequence that allows for sufficient expression of the encoded EPSPS enzyme to enhance the glyphosate tolerance of a plant cell transformed with the polynucleotide.

4. The polynucleotide of claim 3 which further comprises a 3' non-translated region which functions in plant cells to cause the addition of a stretch of polyadenylated nucleotides to the 3' end of the RNA sequence.

5. The polynucleotide of claim 3, wherein said promoter is heterologous with respect to the polynucleotide.

6. A polynucleotide of claim 1 in which the polynucleotide encodes a fission polypeptide comprising an amino-terminal chloroplast transit peptide and the EPSPS enzyme.

7. A method of producing genetically transformed plants which are tolerant toward glyphosate herbicide, comprising the steps of:
   a) inserting into the genome of a plant cell a polynucleotide comprising:
      i) a promoter which functions in plant cells to cause the production of an RNA sequence,
      ii) a polynucleotide encoding a glyphosate tolerant EPSPS enzyme having at least 95% sequence identity to SEQ ID NO:10, 12, or 59;
      iii) a 3' non-translated polynucleotide which functions in plant cells to cause the addition of a stretch of polyadenylated nucleotides to the 3' end of the RNA sequence;
   b) obtaining a transformed plant cell; and
   c) regenerating from the transformed plant cell a genetically transformed plant which has increased tolerance to glyphosate herbicide.

8. The method of claim 7, wherein obtaining the transformed plant comprises screening for an enhanced tolerance to glyphosate herbicide.

9. A method of claim 7 in which the polynucleotide encodes a fusion polypeptide comprising an amino-terminal chloroplast transit peptide and the EPSPS enzyme.

10. A glyphosate-tolerant plant cell comprising the polynucleotide of claim 5.

11. A glyphosate-tolerant plant cell of claim 10 selected from the group consisting of corn, wheat, rice, barley, soybean, cotton, sugarbeet, oilseed rape, canola, flax, sunflower, potato, tobacco, tomato, alfalfa, poplar, pine, eucalyptus, apple, lettuce, peas, lentils, grape and turf grasses.

12. A glyphosate-tolerant plant comprising plant cells of claim 10.

13. A transgenic seed comprising the polynucleotide of claim 1.

14. The glyphosate-tolerant plant of claim 12 selected from the group consisting of corn, wheat, rice, barley, soybean, cotton, sugarbeet, oilseed rape, canola, flax, sunflower, potato, tobacco, tomato, alfalfa, poplar, pine, eucalyptus, apple, lettuce, peas, lentils, grape and turf grasses.

15. A method of producing a genetically transformed plant which is tolerant toward glyphosate herbicide, comprising the steps of:
   a) inserting into the genome of a plant cell a polynucleotide encoding a glyphosate tolerant EPSPS enzyme having at least 95% sequence identity to SEQ ID NO:10, 12, or 59;
   b) obtaining transformed plant cells; and
   c) regenerating from the transformed plant cell a genetically transformed plant which has increased tolerance toward glyphosate herbicide.

* * * * *

UNITED STATES PATENT AND TRADEMARK OFFICE
CERTIFICATE OF CORRECTION

PATENT NO. : 7,700,842 B2  Page 1 of 1
APPLICATION NO. : 11/400598
DATED : April 20, 2010
INVENTOR(S) : Nadine Carozzi et al.

It is certified that error appears in the above-identified patent and that said Letters Patent is hereby corrected as shown below:

Column 131, claim 2, line 16 should read:
a) The nucleotide sequence of SEQ ID NO:9, 11, 57, 58, Column 131, claim 2, line 24 should read:
or 59.

Signed and Sealed this
Twenty-eighth Day of August, 2012

David J. Kappos
*Director of the United States Patent and Trademark Office*

SEQUENCE LISTING

```
<160> NUMBER OF SEQ ID NOS: 68

<210> SEQ ID NO 1
<211> LENGTH: 1257
<212> TYPE: DNA
<213> ORGANISM: Pseudomonas syringae
<220> FEATURE:
<221> NAME/KEY: CDS
<222> LOCATION: (1)...(1257)
<220> FEATURE:
<221> NAME/KEY: misc_feature
<222> LOCATION: (0)...(0)
<223> OTHER INFORMATION: Strain DC3000 EPSPS Gene

<400> SEQUENCE: 1 atg cga cct caa gcc act ctc act gtt atg cct gtc gag cgc ccg ctg      48
Met Arg Pro Gln Ala Thr Leu Thr Val Met Pro Val Glu Arg Pro Leu
 1               5                  10                  15 gtc ggg cgc gtc agc ccg ccg ggc tcc aag tcg atc acc aac cgc gca      96
Val Gly Arg Val Ser Pro Pro Gly Ser Lys Ser Ile Thr Asn Arg Ala
```

-continued

|    |    |    | 20 |    |    |    |    | 25 |    |    |    |    | 30 |    |    |      |
|----|----|----|----|----|----|----|----|----|----|----|----|----|----|----|----|------|
| ctg | ctg | ctg | gcg | ggg | ctt | gcc | aaa | ggc | acc | agc | cgc | ctg | acc | ggc | gcg | 144 |
| Leu | Leu | Leu | Ala | Gly | Leu | Ala | Lys | Gly | Thr | Ser | Arg | Leu | Thr | Gly | Ala |     |
|    |    | 35 |    |    |    |    | 40 |    |    |    |    | 45 |    |    |    |      |

| ctg | aag | agt | gac | gat | acc | cgt | gtg | atg | tcc | gaa | gca | ctg | cga | ctg | atg | 192 |
| Leu | Lys | Ser | Asp | Asp | Thr | Arg | Val | Met | Ser | Glu | Ala | Leu | Arg | Leu | Met |     |
| 50 |    |    |    |    | 55 |    |    |    |    | 60 |    |    |    |    |    |      |

| ggc | gtg | cag | gtc | gac | gag | ccg | gat | gac | agc | acc | ttt | gtg | gtc | acc | agc | 240 |
| Gly | Val | Gln | Val | Asp | Glu | Pro | Asp | Asp | Ser | Thr | Phe | Val | Val | Thr | Ser |     |
| 65 |    |    |    | 70 |    |    |    |    | 75 |    |    |    |    | 80 |    |      |

| agc | ggc | cac | tgg | caa | gcg | ccg | cag | caa | gcg | ctg | ttt | ctc | ggc | aac | gcc | 288 |
| Ser | Gly | His | Trp | Gln | Ala | Pro | Gln | Gln | Ala | Leu | Phe | Leu | Gly | Asn | Ala |     |
|    |    |    | 85 |    |    |    |    | 90 |    |    |    |    | 95 |    |    |      |

| ggg | acc | gcg | acg | cgc | ttt | ctg | acc | gct | gcg | ctg | gcc | aac | ttt | gaa | ggc | 336 |
| Gly | Thr | Ala | Thr | Arg | Phe | Leu | Thr | Ala | Ala | Leu | Ala | Asn | Phe | Glu | Gly |     |
|    |    |    | 100 |    |    |    | 105 |    |    |    |    | 110 |    |    |    |      |

| gac | ttc | gtg | gtg | gat | ggc | gac | gag | tac | atg | cgt | aaa | cgc | ccg | atc | ggc | 384 |
| Asp | Phe | Val | Val | Asp | Gly | Asp | Glu | Tyr | Met | Arg | Lys | Arg | Pro | Ile | Gly |     |
|    |    |    | 115 |    |    |    |    | 120 |    |    |    |    | 125 |    |    |      |

| ccg | ctg | gtc | gat | gcc | ttg | cag | cgc | atg | ggc | gtg | gaa | atc | agc | gcg | ccc | 432 |
| Pro | Leu | Val | Asp | Ala | Leu | Gln | Arg | Met | Gly | Val | Glu | Ile | Ser | Ala | Pro |     |
|    | 130 |    |    |    |    | 135 |    |    |    |    | 140 |    |    |    |    |      |

| agc | ggt | tgc | ccg | ccc | gtg | gcg | atc | aag | ggc | aag | ggc | ggt | ctg | caa | gcc | 480 |
| Ser | Gly | Cys | Pro | Pro | Val | Ala | Ile | Lys | Gly | Lys | Gly | Gly | Leu | Gln | Ala |     |
| 145 |    |    |    | 150 |    |    |    |    | 155 |    |    |    |    | 160 |    |      |

| ggg | cgt | att | gaa | atc | gac | ggc | aac | ctg | tcc | agc | cag | tac | gta | tcg | gcg | 528 |
| Gly | Arg | Ile | Glu | Ile | Asp | Gly | Asn | Leu | Ser | Ser | Gln | Tyr | Val | Ser | Ala |     |
|    |    |    | 165 |    |    |    | 170 |    |    |    |    | 175 |    |    |    |      |

| ctg | ctg | atg | gcc | gga | gcg | tgt | ggc | aaa | ggc | tcg | ctt | gaa | gtt | gct | ctg | 576 |
| Leu | Leu | Met | Ala | Gly | Ala | Cys | Gly | Lys | Gly | Ser | Leu | Glu | Val | Ala | Leu |     |
|    |    |    | 180 |    |    |    | 185 |    |    |    |    | 190 |    |    |    |      |

| acc | ggt | agc | gag | atc | ggc | gca | cgc | ggc | tat | gtc | gac | ctg | acc | ctg | gcg | 624 |
| Thr | Gly | Ser | Glu | Ile | Gly | Ala | Arg | Gly | Tyr | Val | Asp | Leu | Thr | Leu | Ala |     |
|    |    | 195 |    |    |    |    | 200 |    |    |    |    | 205 |    |    |    |      |

| gcg | atg | cag | gcc | ttc | ggc | gct | gaa | gtt | cag | gcc | atc | ggc | gac | gct | gcc | 672 |
| Ala | Met | Gln | Ala | Phe | Gly | Ala | Glu | Val | Gln | Ala | Ile | Gly | Asp | Ala | Ala |     |
|    | 210 |    |    |    |    | 215 |    |    |    |    | 220 |    |    |    |    |      |

| tgg | aaa | gtc | tcg | gcc | acc | ggc | tac | cac | gct | acg | gat | ttc | cac | atc | gag | 720 |
| Trp | Lys | Val | Ser | Ala | Thr | Gly | Tyr | His | Ala | Thr | Asp | Phe | His | Ile | Glu |     |
| 225 |    |    |    | 230 |    |    |    |    | 235 |    |    |    |    | 240 |    |      |

| ccg | gat | gca | tcg | gca | gcc | acc | tac | ctc | tgg | gcc | gca | caa | gcc | ctg | acc | 768 |
| Pro | Asp | Ala | Ser | Ala | Ala | Thr | Tyr | Leu | Trp | Ala | Ala | Gln | Ala | Leu | Thr |     |
|    |    |    | 245 |    |    |    |    | 250 |    |    |    |    | 255 |    |    |      |

| gaa | ggc | aac | atc | gac | ctg | ggc | gtg | gcc | agt | gat | gca | ttc | act | cag | cct | 816 |
| Glu | Gly | Asn | Ile | Asp | Leu | Gly | Val | Ala | Ser | Asp | Ala | Phe | Thr | Gln | Pro |     |
|    |    |    | 260 |    |    |    | 265 |    |    |    |    | 270 |    |    |    |      |

| gac | gcg | ctg | gcc | agc | cag | atc | atc | gac | agc | ttc | ccg | aac | atg | ccg | gcg | 864 |
| Asp | Ala | Leu | Ala | Ser | Gln | Ile | Ile | Asp | Ser | Phe | Pro | Asn | Met | Pro | Ala |     |
|    |    | 275 |    |    |    |    | 280 |    |    |    |    | 285 |    |    |    |      |

| gtg | atc | gac | ggt | tcg | caa | atg | cag | gac | gcc | att | ccg | acc | ctc | gca | gtg | 912 |
| Val | Ile | Asp | Gly | Ser | Gln | Met | Gln | Asp | Ala | Ile | Pro | Thr | Leu | Ala | Val |     |
|    | 290 |    |    |    |    | 295 |    |    |    |    | 300 |    |    |    |    |      |

| ctc | gcg | gcc | ttc | aat | cgt | cag | ccg | gta | cgc | ttc | gtc | ggc | atc | gcc | aac | 960 |
| Leu | Ala | Ala | Phe | Asn | Arg | Gln | Pro | Val | Arg | Phe | Val | Gly | Ile | Ala | Asn |     |
| 305 |    |    |    | 310 |    |    |    |    | 315 |    |    |    |    | 320 |    |      |

| ctg | cgg | gtc | aag | gaa | tgt | gat | cgt | att | tca | gcg | ctg | tgt | gac | ggc | ctg | 1008 |
| Leu | Arg | Val | Lys | Glu | Cys | Asp | Arg | Ile | Ser | Ala | Leu | Cys | Asp | Gly | Leu |     |
|    |    |    | 325 |    |    |    | 330 |    |    |    |    | 335 |    |    |    |      |

| tgc | gcc | atc | gca | ccg | ggc | ctt | gcg | gtt | gaa | gag | ggc | gac | gac | ctg | atc | 1056 |

```
Cys Ala Ile Ala Pro Gly Leu Ala Val Glu Glu Gly Asp Asp Leu Ile
            340                 345                 350 gtg cac gcc aac ccg gcg ctg gca ggg acc aca gtc aac gca ctg atc      1104
Val His Ala Asn Pro Ala Leu Ala Gly Thr Thr Val Asn Ala Leu Ile
        355                 360                 365 gac acc cat tcc gac cat cgc atc gcc atg tgc ttt gcc ctg gct ggt      1152
Asp Thr His Ser Asp His Arg Ile Ala Met Cys Phe Ala Leu Ala Gly
370                 375                 380 ttg aag atc aaa ggc atc cat att cag gat ccc gat tgc gtc gcc aag      1200
Leu Lys Ile Lys Gly Ile His Ile Gln Asp Pro Asp Cys Val Ala Lys
385                 390                 395                 400 acc tat ccg ggt tac tgg gat gcg ctg gct tcg ctg ggg gtg agt gtt      1248
Thr Tyr Pro Gly Tyr Trp Asp Ala Leu Ala Ser Leu Gly Val Ser Val
                405                 410                 415 cag cgc tga                                                          1257
Gln Arg  *
```

<210> SEQ ID NO 2
<211> LENGTH: 418
<212> TYPE: PRT
<213> ORGANISM: Pseudomonas syringae

<400> SEQUENCE: 2

```
Met Arg Pro Gln Ala Thr Leu Thr Val Met Pro Val Glu Arg Pro Leu
1               5                   10                  15

Val Gly Arg Val Ser Pro Pro Gly Ser Lys Ser Ile Thr Asn Arg Ala
            20                  25                  30

Leu Leu Leu Ala Gly Leu Ala Lys Gly Thr Ser Arg Leu Thr Gly Ala
        35                  40                  45

Leu Lys Ser Asp Asp Thr Arg Val Met Ser Glu Ala Leu Arg Leu Met
    50                  55                  60

Gly Val Gln Val Asp Glu Pro Asp Asp Ser Thr Phe Val Val Thr Ser
65                  70                  75                  80

Ser Gly His Trp Gln Ala Pro Gln Gln Ala Leu Phe Leu Gly Asn Ala
                85                  90                  95

Gly Thr Ala Thr Arg Phe Leu Thr Ala Ala Leu Ala Asn Phe Glu Gly
            100                 105                 110

Asp Phe Val Val Asp Gly Asp Glu Tyr Met Arg Lys Arg Pro Ile Gly
        115                 120                 125

Pro Leu Val Asp Ala Leu Gln Arg Met Gly Val Glu Ile Ser Ala Pro
    130                 135                 140

Ser Gly Cys Pro Pro Val Ala Ile Lys Gly Lys Gly Leu Gln Ala
145                 150                 155                 160

Gly Arg Ile Glu Ile Asp Gly Asn Leu Ser Ser Gln Tyr Val Ser Ala
                165                 170                 175

Leu Leu Met Ala Gly Ala Cys Gly Lys Gly Ser Leu Glu Val Ala Leu
            180                 185                 190

Thr Gly Ser Glu Ile Gly Ala Arg Gly Tyr Val Asp Leu Thr Leu Ala
        195                 200                 205

Ala Met Gln Ala Phe Gly Ala Glu Val Gln Ala Ile Gly Asp Ala Ala
    210                 215                 220

Trp Lys Val Ser Ala Thr Gly Tyr His Ala Thr Asp Phe His Ile Glu
225                 230                 235                 240

Pro Asp Ala Ser Ala Ala Thr Tyr Leu Trp Ala Ala Gln Ala Leu Thr
                245                 250                 255

Glu Gly Asn Ile Asp Leu Gly Val Ala Ser Asp Ala Phe Thr Gln Pro
```

```
                    260              265              270
Asp Ala Leu Ala Ser Gln Ile Ile Asp Ser Phe Pro Asn Met Pro Ala
            275              280              285

Val Ile Asp Gly Ser Gln Met Gln Asp Ala Ile Pro Thr Leu Ala Val
        290              295              300

Leu Ala Ala Phe Asn Arg Gln Pro Val Arg Phe Val Gly Ile Ala Asn
305              310              315              320

Leu Arg Val Lys Glu Cys Asp Arg Ile Ser Ala Leu Cys Asp Gly Leu
                325              330              335

Cys Ala Ile Ala Pro Gly Leu Ala Val Glu Glu Gly Asp Asp Leu Ile
            340              345              350

Val His Ala Asn Pro Ala Leu Ala Gly Thr Thr Val Asn Ala Leu Ile
            355              360              365

Asp Thr His Ser Asp His Arg Ile Ala Met Cys Phe Ala Leu Ala Gly
        370              375              380

Leu Lys Ile Lys Gly Ile His Ile Gln Asp Pro Asp Cys Val Ala Lys
385              390              395              400

Thr Tyr Pro Gly Tyr Trp Asp Ala Leu Ala Ser Leu Gly Val Ser Val
                405              410              415

Gln Arg

<210> SEQ ID NO 3
<211> LENGTH: 1278
<212> TYPE: DNA
<213> ORGANISM: Agrobacterium tumifaciens
<220> FEATURE:
<221> NAME/KEY: CDS
<222> LOCATION: (1)...(1278)
<220> FEATURE:
<221> NAME/KEY: misc_feature
<222> LOCATION: (0)...(0)
<223> OTHER INFORMATION: Strain C58 EPSPS

<400> SEQUENCE: 3 atg atc gaa ctg acc atc acc ccg ccc ggc cac ccg ctt tcc ggc aag      48
Met Ile Glu Leu Thr Ile Thr Pro Pro Gly His Pro Leu Ser Gly Lys
 1               5                  10                  15 gtg gag ccg ccc ggc tcc aaa tcc atc acc aac cgc gcg ctt ctc ttg      96
Val Glu Pro Pro Gly Ser Lys Ser Ile Thr Asn Arg Ala Leu Leu Leu
            20                  25                  30 gcc ggc ctc gcc aag ggc aaa agc cac ttg tca ggc gcc ctg aaa agc     144
Ala Gly Leu Ala Lys Gly Lys Ser His Leu Ser Gly Ala Leu Lys Ser
        35                  40                  45 gac gat acg ctt tat atg gcc gaa gct ctg cgg gag atg ggc gtg aag     192
Asp Asp Thr Leu Tyr Met Ala Glu Ala Leu Arg Glu Met Gly Val Lys
    50                  55                  60 gtc acc gag cct gac gcc acc acc ttc gtg gtg gag gga acg ggc gtg     240
Val Thr Glu Pro Asp Ala Thr Thr Phe Val Val Glu Gly Thr Gly Val
65                  70                  75                  80 ctg cag cag ccg gaa aag ccg ctg ttc ctc ggc aat gcc ggc acc gcc     288
Leu Gln Gln Pro Glu Lys Pro Leu Phe Leu Gly Asn Ala Gly Thr Ala
                85                  90                  95 acg cgg ttc ctg act gcc gcc ggg gca ctt gtc gat ggc gcc gtc atc     336
Thr Arg Phe Leu Thr Ala Ala Gly Ala Leu Val Asp Gly Ala Val Ile
            100                 105                 110 atc gat ggg gac gaa cat atg cgc aaa cgc ccg ata ctg ccg ctg gtg     384
Ile Asp Gly Asp Glu His Met Arg Lys Arg Pro Ile Leu Pro Leu Val
        115                 120                 125 cag gcg ctg cgg gct ctc ggc gtg gaa gcg gat gcg cca acc ggc tgc     432
```

```
                Gln Ala Leu Arg Ala Leu Gly Val Glu Ala Asp Ala Pro Thr Gly Cys
                    130                 135                 140 ccg cct gtc acc gtc cgt ggc aag ggt atg ggt ttt cca aag ggc agc       480
Pro Pro Val Thr Val Arg Gly Lys Gly Met Gly Phe Pro Lys Gly Ser
145                 150                 155                 160 gtc acc atc gac gcc aat ctc tcc agc cag tat gtg tcg gca ctg ttg       528
Val Thr Ile Asp Ala Asn Leu Ser Ser Gln Tyr Val Ser Ala Leu Leu
                165                 170                 175 atg gcc gcc gcc tgc ggt gac aag ccc gtg gat atc atc ctg aag ggt       576
Met Ala Ala Ala Cys Gly Asp Lys Pro Val Asp Ile Ile Leu Lys Gly
            180                 185                 190 gag gaa atc ggc gcg aag ggc tat atc gac ctc acc aca tcc gcc atg       624
Glu Glu Ile Gly Ala Lys Gly Tyr Ile Asp Leu Thr Thr Ser Ala Met
        195                 200                 205 gaa gcc ttc gga gcg aag gtg gag cgg gtc agc aac gcc atc tgg cgc       672
Glu Ala Phe Gly Ala Lys Val Glu Arg Val Ser Asn Ala Ile Trp Arg
    210                 215                 220 gtg cat ccg acc ggt tac acg gca acc gat ttc cac atc gag ccg gat       720
Val His Pro Thr Gly Tyr Thr Ala Thr Asp Phe His Ile Glu Pro Asp
225                 230                 235                 240 gcc tcc gcc gcc acc tat ctc tgg ggc gcg gag ctt ctg acc ggc ggt       768
Ala Ser Ala Ala Thr Tyr Leu Trp Gly Ala Glu Leu Leu Thr Gly Gly
                245                 250                 255 gct atc gat atc ggc acg ccc gct gac aaa ttc act cag ccg gat gcc       816
Ala Ile Asp Ile Gly Thr Pro Ala Asp Lys Phe Thr Gln Pro Asp Ala
                260                 265                 270 aag gct tat gag gtc atg gcg cag ttt ccg cat ctg ccc gcc gaa atc       864
Lys Ala Tyr Glu Val Met Ala Gln Phe Pro His Leu Pro Ala Glu Ile
            275                 280                 285 gac ggt tcg cag atg cag gac gcc att cca acc atc gcg gtt atc gcc       912
Asp Gly Ser Gln Met Gln Asp Ala Ile Pro Thr Ile Ala Val Ile Ala
        290                 295                 300 gcc ttc aac gag acg ccg gtg cgt ttc gtc ggc atc gcc aat ctg cgc       960
Ala Phe Asn Glu Thr Pro Val Arg Phe Val Gly Ile Ala Asn Leu Arg
305                 310                 315                 320 gtc aag gaa tgc gac cgc atc cgc gcc gtc tcg ctc ggc ctc aac gaa      1008
Val Lys Glu Cys Asp Arg Ile Arg Ala Val Ser Leu Gly Leu Asn Glu
                325                 330                 335 atc cgc gag ggt ctg gcg cat gaa gag ggt gac gac ctg atc gta cat      1056
Ile Arg Glu Gly Leu Ala His Glu Glu Gly Asp Asp Leu Ile Val His
                340                 345                 350 gcc gat ccg tcg ctc gcc ggg cag acg gtc gat gcc tcc atc gat acc      1104
Ala Asp Pro Ser Leu Ala Gly Gln Thr Val Asp Ala Ser Ile Asp Thr
            355                 360                 365 ttt gcc gat cac cgc atc gcc atg agt ttt gca ctg gcg gcg ctc aag      1152
Phe Ala Asp His Arg Ile Ala Met Ser Phe Ala Leu Ala Ala Leu Lys
        370                 375                 380 atc gga ggc atc gcc atc cag aat ccc gcc tgc gtg gcc aag acc tat      1200
Ile Gly Gly Ile Ala Ile Gln Asn Pro Ala Cys Val Ala Lys Thr Tyr
385                 390                 395                 400 ccg ggc tac tgg aaa gcg ctt gcc tcg ctc ggc gtc gac tat acc gaa      1248
Pro Gly Tyr Trp Lys Ala Leu Ala Ser Leu Gly Val Asp Tyr Thr Glu
                405                 410                 415 aag gaa agc gct gcc gag ccg cag cac tga                              1278
Lys Glu Ser Ala Ala Glu Pro Gln His *
            420                 425

<210> SEQ ID NO 4
<211> LENGTH: 425
<212> TYPE: PRT
```

<213> ORGANISM: Agrobacterium tumifaciens

<400> SEQUENCE: 4

```
Met Ile Glu Leu Thr Ile Thr Pro Gly His Pro Leu Ser Gly Lys
 1               5                  10                  15

Val Glu Pro Pro Gly Ser Lys Ser Ile Thr Asn Arg Ala Leu Leu
            20                  25                  30

Ala Gly Leu Ala Lys Gly Lys Ser His Leu Ser Gly Ala Leu Lys Ser
        35                  40                  45

Asp Asp Thr Leu Tyr Met Ala Glu Ala Leu Arg Glu Met Gly Val Lys
 50                  55                  60

Val Thr Glu Pro Asp Ala Thr Thr Phe Val Val Glu Gly Thr Gly Val
 65                  70                  75                  80

Leu Gln Gln Pro Glu Lys Pro Leu Phe Leu Gly Asn Ala Gly Thr Ala
                85                  90                  95

Thr Arg Phe Leu Thr Ala Ala Gly Ala Leu Val Asp Gly Ala Val Ile
            100                 105                 110

Ile Asp Gly Asp Glu His Met Arg Lys Arg Pro Ile Leu Pro Leu Val
        115                 120                 125

Gln Ala Leu Arg Ala Leu Gly Val Glu Ala Asp Ala Pro Thr Gly Cys
130                 135                 140

Pro Pro Val Thr Val Arg Gly Lys Gly Met Gly Phe Pro Lys Gly Ser
145                 150                 155                 160

Val Thr Ile Asp Ala Asn Leu Ser Ser Gln Tyr Val Ser Ala Leu Leu
                165                 170                 175

Met Ala Ala Ala Cys Gly Asp Lys Pro Val Asp Ile Ile Leu Lys Gly
            180                 185                 190

Glu Glu Ile Gly Ala Lys Gly Tyr Ile Asp Leu Thr Thr Ser Ala Met
        195                 200                 205

Glu Ala Phe Gly Ala Lys Val Glu Arg Val Ser Asn Ala Ile Trp Arg
210                 215                 220

Val His Pro Thr Gly Tyr Thr Ala Thr Asp Phe His Ile Glu Pro Asp
225                 230                 235                 240

Ala Ser Ala Ala Thr Tyr Leu Trp Gly Ala Glu Leu Leu Thr Gly Gly
                245                 250                 255

Ala Ile Asp Ile Gly Thr Pro Ala Asp Lys Phe Thr Gln Pro Asp Ala
            260                 265                 270

Lys Ala Tyr Glu Val Met Ala Gln Phe Pro His Leu Pro Ala Glu Ile
        275                 280                 285

Asp Gly Ser Gln Met Gln Asp Ala Ile Pro Thr Ile Ala Val Ile Ala
290                 295                 300

Ala Phe Asn Glu Thr Pro Val Arg Phe Val Gly Ile Ala Asn Leu Arg
305                 310                 315                 320

Val Lys Glu Cys Asp Arg Ile Arg Ala Val Ser Leu Gly Leu Asn Glu
                325                 330                 335

Ile Arg Glu Gly Leu Ala His Glu Gly Asp Asp Leu Ile Val His
            340                 345                 350

Ala Asp Pro Ser Leu Ala Gly Gln Thr Val Asp Ala Ser Ile Asp Thr
        355                 360                 365

Phe Ala Asp His Arg Ile Ala Met Ser Phe Ala Leu Ala Ala Leu Lys
370                 375                 380

Ile Gly Gly Ile Ala Ile Gln Asn Pro Ala Cys Val Ala Lys Thr Tyr
385                 390                 395                 400
```

-continued

```
Pro Gly Tyr Trp Lys Ala Leu Ala Ser Leu Gly Val Asp Tyr Thr Glu
            405                 410                 415
Lys Glu Ser Ala Ala Glu Pro Gln His
        420                 425

<210> SEQ ID NO 5
<211> LENGTH: 1398
<212> TYPE: DNA
<213> ORGANISM: Enterobacteriaceae
<220> FEATURE:
<221> NAME/KEY: CDS
<222> LOCATION: (103)...(1398)

<400> SEQUENCE: 5
aaaaaaggaa atgaactatg tgttgctgga aaaagtaggg aagggagtgg tgaagagtat      60
tccactggtt caattagaaa aaatcattca aggattacca aa gtg aaa gta aca        114
                                              Val Lys Val Thr
                                                1 ata cag ccc gga gat ctg act gga att atc cag tca ccc gct tca aaa       162
Ile Gln Pro Gly Asp Leu Thr Gly Ile Ile Gln Ser Pro Ala Ser Lys
  5              10                  15                  20 agt tcg atg cag cga gct tgt gct gct gca ctg gtt gca aaa gga ata       210
Ser Ser Met Gln Arg Ala Cys Ala Ala Ala Leu Val Ala Lys Gly Ile
             25                  30                  35 agt gag atc att aat ccc ggt cat agc aat gat gat aaa gct gcc agg       258
Ser Glu Ile Ile Asn Pro Gly His Ser Asn Asp Asp Lys Ala Ala Arg
         40                  45                  50 gat att gta agc cgg ctt ggt gcc agg ctt gaa gat cag cct gat ggt       306
Asp Ile Val Ser Arg Leu Gly Ala Arg Leu Glu Asp Gln Pro Asp Gly
     55                  60                  65 tct ttg cag ata aca agt gaa ggc gta aaa cct gtc gct cct ttt att       354
Ser Leu Gln Ile Thr Ser Glu Gly Val Lys Pro Val Ala Pro Phe Ile
 70                  75                  80 gac tgc ggt gaa tct ggt tta agt atc cgg atg ttt act ccg att gtt       402
Asp Cys Gly Glu Ser Gly Leu Ser Ile Arg Met Phe Thr Pro Ile Val
 85                  90                  95                 100 gcg ttg agt aaa gaa gag gtg acg atc aaa gga tct gga agc ctt gtt       450
Ala Leu Ser Lys Glu Glu Val Thr Ile Lys Gly Ser Gly Ser Leu Val
                 105                 110                 115 aca aga cca atg gat ttc ttt gat gaa att ctt ccg cat ctc ggt gta       498
Thr Arg Pro Met Asp Phe Phe Asp Glu Ile Leu Pro His Leu Gly Val
             120                 125                 130 aaa gtt aaa tct aac cag ggt aaa ttg cct ctc gtt ata cag ggg cca       546
Lys Val Lys Ser Asn Gln Gly Lys Leu Pro Leu Val Ile Gln Gly Pro
         135                 140                 145 ttg aaa cca gca gac gtt acg gtt gat ggg tcc tta agc tct cag ttc       594
Leu Lys Pro Ala Asp Val Thr Val Asp Gly Ser Leu Ser Ser Gln Phe
    150                 155                 160 ctt aca ggt ttg ttg ctt gca tat gcg gcc gca gat gca agc gat gtt       642
Leu Thr Gly Leu Leu Leu Ala Tyr Ala Ala Ala Asp Ala Ser Asp Val
165                 170                 175                 180 gcg ata aaa gta acg aat ctc aaa agc cgt ccg tat atc gat ctt aca       690
Ala Ile Lys Val Thr Asn Leu Lys Ser Arg Pro Tyr Ile Asp Leu Thr
                185                 190                 195 ctg gat gtg atg aag cgg ttt ggt ttg aag act ccc gag aat cga aac       738
Leu Asp Val Met Lys Arg Phe Gly Leu Lys Thr Pro Glu Asn Arg Asn
            200                 205                 210 tat gaa gag ttt tat ttc aaa gcc ggg aat gta tat gat gaa acg aaa       786
Tyr Glu Glu Phe Tyr Phe Lys Ala Gly Asn Val Tyr Asp Glu Thr Lys
        215                 220                 225
```

| | | |
|---|---|---|
| atg caa cga tac acc gta gaa ggc gac tgg agc ggt ggt gct ttt tta<br>Met Gln Arg Tyr Thr Val Glu Gly Asp Trp Ser Gly Gly Ala Phe Leu<br>230                        235                          240 | | 834 |
| ctg gta gcg ggg gct att gcc ggg ccg atc acg gta aga ggt ttg gat<br>Leu Val Ala Gly Ala Ile Ala Gly Pro Ile Thr Val Arg Gly Leu Asp<br>245                        250                        255                260 | | 882 |
| ata gct tcg acg cag gct gat aaa gcg atc gtt cag gct ttg atg agt<br>Ile Ala Ser Thr Gln Ala Asp Lys Ala Ile Val Gln Ala Leu Met Ser<br>                        265                        270                        275 | | 930 |
| gcg aac gca ggt att gcg att gat gca aaa gag atc aaa ctt cat cct<br>Ala Asn Ala Gly Ile Ala Ile Asp Ala Lys Glu Ile Lys Leu His Pro<br>                  280                        285                        290 | | 978 |
| gct gat ctc aat gca ttt gaa ttt gat gct act gat tgc ccg gat ctt<br>Ala Asp Leu Asn Ala Phe Glu Phe Asp Ala Thr Asp Cys Pro Asp Leu<br>                  295                        300                        305 | | 1026 |
| ttt ccg cca ttg gtt gct ttg gcg tct tat tgc aaa gga gaa aca aag<br>Phe Pro Pro Leu Val Ala Leu Ala Ser Tyr Cys Lys Gly Glu Thr Lys<br>310                        315                        320 | | 1074 |
| atc aaa ggc gta agc agg ctg gcg cat aaa gaa agt gac aga gga ttg<br>Ile Lys Gly Val Ser Arg Leu Ala His Lys Glu Ser Asp Arg Gly Leu<br>325                        330                        335                340 | | 1122 |
| acg ctg cag gac gag ttc ggg aaa atg ggt gtt gaa atc cac ctt gag<br>Thr Leu Gln Asp Glu Phe Gly Lys Met Gly Val Glu Ile His Leu Glu<br>                        345                        350                        355 | | 1170 |
| gga gat ctg atg cgc gtg atc gga ggg aaa ggc gta aaa gga gct gaa<br>Gly Asp Leu Met Arg Val Ile Gly Gly Lys Gly Val Lys Gly Ala Glu<br>                  360                        365                        370 | | 1218 |
| gtt agt tca agg cac gat cat cgc att gcg atg gct tgc gcg gtg gct<br>Val Ser Ser Arg His Asp His Arg Ile Ala Met Ala Cys Ala Val Ala<br>                        375                        380                        385 | | 1266 |
| gct tta aaa gct gtg ggt gaa aca acc atc gaa cat gca gaa gcg gtg<br>Ala Leu Lys Ala Val Gly Glu Thr Thr Ile Glu His Ala Glu Ala Val<br>390                        395                        400 | | 1314 |
| aat aaa tcc tac ccg gat ttt tac agc gat ctt aaa caa ctt ggc ggt<br>Asn Lys Ser Tyr Pro Asp Phe Tyr Ser Asp Leu Lys Gln Leu Gly Gly<br>405                        410                        415                420 | | 1362 |
| gtt gta tct tta aac cat caa ttt aat ttc tca tga<br>Val Val Ser Leu Asn His Gln Phe Asn Phe Ser *<br>                  425                        430 | | 1398 |

<210> SEQ ID NO 6
<211> LENGTH: 431
<212> TYPE: PRT
<213> ORGANISM: Enterobacteriaceae

<400> SEQUENCE: 6

Val Lys Val Thr Ile Gln Pro Gly Asp Leu Thr Gly Ile Ile Gln Ser
1                5                      10                    15

Pro Ala Ser Lys Ser Ser Met Gln Arg Ala Cys Ala Ala Ala Leu Val
                20                      25                      30

Ala Lys Gly Ile Ser Glu Ile Ile Asn Pro Gly His Ser Asn Asp Asp
                  35                    40                    45

Lys Ala Ala Arg Asp Ile Val Ser Arg Leu Gly Ala Arg Leu Glu Asp
     50                    55                      60

Gln Pro Asp Gly Ser Leu Gln Ile Thr Ser Glu Gly Val Lys Pro Val
65                70                      75                    80

Ala Pro Phe Ile Asp Cys Gly Glu Ser Gly Leu Ser Ile Arg Met Phe
                  85                    90                    95

Thr Pro Ile Val Ala Leu Ser Lys Glu Glu Val Thr Ile Lys Gly Ser

```
            100                 105                 110
Gly Ser Leu Val Thr Arg Pro Met Asp Phe Phe Asp Glu Ile Leu Pro
        115                 120                 125

His Leu Gly Val Lys Val Lys Ser Asn Gln Gly Lys Leu Pro Leu Val
        130                 135                 140

Ile Gln Gly Pro Leu Lys Pro Ala Asp Val Thr Val Asp Gly Ser Leu
145                 150                 155                 160

Ser Ser Gln Phe Leu Thr Gly Leu Leu Leu Ala Tyr Ala Ala Ala Asp
                165                 170                 175

Ala Ser Asp Val Ala Ile Lys Val Thr Asn Leu Lys Ser Arg Pro Tyr
            180                 185                 190

Ile Asp Leu Thr Leu Asp Val Met Lys Arg Phe Gly Leu Lys Thr Pro
        195                 200                 205

Glu Asn Arg Asn Tyr Glu Glu Phe Tyr Phe Lys Ala Gly Asn Val Tyr
        210                 215                 220

Asp Glu Thr Lys Met Gln Arg Tyr Thr Val Glu Gly Asp Trp Ser Gly
225                 230                 235                 240

Gly Ala Phe Leu Leu Val Ala Gly Ala Ile Ala Gly Pro Ile Thr Val
                245                 250                 255

Arg Gly Leu Asp Ile Ala Ser Thr Gln Ala Asp Lys Ala Ile Val Gln
            260                 265                 270

Ala Leu Met Ser Ala Asn Ala Gly Ile Ala Ile Asp Ala Lys Glu Ile
        275                 280                 285

Lys Leu His Pro Ala Asp Leu Asn Ala Phe Glu Phe Asp Ala Thr Asp
        290                 295                 300

Cys Pro Asp Leu Phe Pro Pro Leu Val Ala Leu Ala Ser Tyr Cys Lys
305                 310                 315                 320

Gly Glu Thr Lys Ile Lys Gly Val Ser Arg Leu Ala His Lys Glu Ser
                325                 330                 335

Asp Arg Gly Leu Thr Leu Gln Asp Glu Phe Gly Lys Met Gly Val Glu
            340                 345                 350

Ile His Leu Glu Gly Asp Leu Met Arg Val Ile Gly Gly Lys Gly Val
        355                 360                 365

Lys Gly Ala Glu Val Ser Ser Arg His Asp His Arg Ile Ala Met Ala
        370                 375                 380

Cys Ala Val Ala Ala Leu Lys Ala Val Gly Glu Thr Thr Ile Glu His
385                 390                 395                 400

Ala Glu Ala Val Asn Lys Ser Tyr Pro Asp Phe Tyr Ser Asp Leu Lys
                405                 410                 415

Gln Leu Gly Gly Val Val Ser Leu Asn His Gln Phe Asn Phe Ser
            420                 425                 430

<210> SEQ ID NO 7
<211> LENGTH: 1257
<212> TYPE: DNA
<213> ORGANISM: Brevundomonas vesicularis
<220> FEATURE:
<221> NAME/KEY: CDS
<222> LOCATION: (1)...(1257)

<400> SEQUENCE: 7 atg atg atg ggt aga gcc aaa ctc acg att atc ccg ccg ggc aag cct      48
Met Met Met Gly Arg Ala Lys Leu Thr Ile Ile Pro Pro Gly Lys Pro
 1               5                   10                  15 ttg acc gga cgc gcc atg ccg ccg gga tcg aag tcg atc acc aac cgc      96
Leu Thr Gly Arg Ala Met Pro Pro Gly Ser Lys Ser Ile Thr Asn Arg
```

-continued

```
                  20                  25                  30
gca ttg ctg ctc gcc ggc ctc gcc aag ggc acg agc cgg cta acc ggt     144
Ala Leu Leu Leu Ala Gly Leu Ala Lys Gly Thr Ser Arg Leu Thr Gly
         35                  40                  45 gcg ctg aag agc gac gat acc cgc tat atg gcc gaa gcg ctg cgt gcg     192
Ala Leu Lys Ser Asp Asp Thr Arg Tyr Met Ala Glu Ala Leu Arg Ala
 50                  55                  60 atg ggt gta acg atc gac gag ccc gac gac acc acg ttc atc gtc aaa     240
Met Gly Val Thr Ile Asp Glu Pro Asp Asp Thr Thr Phe Ile Val Lys
 65                  70                  75                  80 ggc agc ggc aag ctg cag ccg ccg gca gcc ccg ctt ttc ctc ggc aat     288
Gly Ser Gly Lys Leu Gln Pro Pro Ala Ala Pro Leu Phe Leu Gly Asn
                 85                  90                  95 gcc ggc acg gca acg cgc ttc ctg acg gcg gcc gcg gca ctg gtg gac     336
Ala Gly Thr Ala Thr Arg Phe Leu Thr Ala Ala Ala Leu Val Asp
            100                 105                 110 ggc aag gtc atc gtc gac ggc gat gcc cat atg cgc aag cgg ccg atc     384
Gly Lys Val Ile Val Asp Gly Asp Ala His Met Arg Lys Arg Pro Ile
        115                 120                 125 gga ccg cta gtc gac gcg ttg cgc tcg ctc ggc atc gat gcc tcg gct     432
Gly Pro Leu Val Asp Ala Leu Arg Ser Leu Gly Ile Asp Ala Ser Ala
130                 135                 140 gaa acc ggc tgc ccg cca gtc acg atc aac ggc acc ggc cgc ttc gag     480
Glu Thr Gly Cys Pro Pro Val Thr Ile Asn Gly Thr Gly Arg Phe Glu
145                 150                 155                 160 gca agc cgc gtg cag atc gat ggc ggc ctg tcc agc cag tat gtc tcg     528
Ala Ser Arg Val Gln Ile Asp Gly Gly Leu Ser Ser Gln Tyr Val Ser
                165                 170                 175 gcg ctc ctg atg atg gcc gcc ggc ggt gat cgc gct gtc gat gtc gag     576
Ala Leu Leu Met Met Ala Ala Gly Gly Asp Arg Ala Val Asp Val Glu
            180                 185                 190 ctt ctc ggc gaa cat atc ggc gct ctc ggc tat atc gac ctg acc gtt     624
Leu Leu Gly Glu His Ile Gly Ala Leu Gly Tyr Ile Asp Leu Thr Val
        195                 200                 205 gcc gcc atg cgc gct ttc ggc gcg aag gtt gag cgt gtg agc ccg gtc     672
Ala Ala Met Arg Ala Phe Gly Ala Lys Val Glu Arg Val Ser Pro Val
    210                 215                 220 gcc tgg cgc gtc gag ccc acc ggc tat cat gcg gcc gac ttc gtg atc     720
Ala Trp Arg Val Glu Pro Thr Gly Tyr His Ala Ala Asp Phe Val Ile
225                 230                 235                 240 gag ccg gat gcc tct gct gcg acc tat ctc tgg gcc gcc gaa gtt ctg     768
Glu Pro Asp Ala Ser Ala Ala Thr Tyr Leu Trp Ala Ala Glu Val Leu
                245                 250                 255 agc ggc ggc aag atc gat ctc ggc acg ccg gcg gaa cag ttc tcg caa     816
Ser Gly Gly Lys Ile Asp Leu Gly Thr Pro Ala Glu Gln Phe Ser Gln
            260                 265                 270 ccg gat gcg aaa gcc tat gat ctg att tcg aaa ttc ccg cat ctg cct     864
Pro Asp Ala Lys Ala Tyr Asp Leu Ile Ser Lys Phe Pro His Leu Pro
        275                 280                 285 gct gtc atc gac ggc tcg cag atg cag gac gcc atc ccg acg ctc gcc     912
Ala Val Ile Asp Gly Ser Gln Met Gln Asp Ala Ile Pro Thr Leu Ala
    290                 295                 300 gtt ctc gcc gct ttc aac gaa atg cct gtg cgc ttc gtc ggt atc gaa     960
Val Leu Ala Ala Phe Asn Glu Met Pro Val Arg Phe Val Gly Ile Glu
305                 310                 315                 320 aac ctg cgc gtc aag gaa tgc gat cgt atc cgc gcg ctc tcg agc ggc    1008
Asn Leu Arg Val Lys Glu Cys Asp Arg Ile Arg Ala Leu Ser Ser Gly
                325                 330                 335 cta tcc cgc atc gtt ccg aac ctc ggc acg gaa gag ggc gac gat ctc    1056
```

-continued

```
Leu Ser Arg Ile Val Pro Asn Leu Gly Thr Glu Glu Gly Asp Asp Leu
                340                 345                 350 atc atc gcc tcc gat ccg agc ctt gcc ggc aaa atc ctg acc gca gag      1104
Ile Ile Ala Ser Asp Pro Ser Leu Ala Gly Lys Ile Leu Thr Ala Glu
            355                 360                 365 atc gat agc ttt gcc gat cac cgc atc gcc atg agc ttt gcg ctg gcc      1152
Ile Asp Ser Phe Ala Asp His Arg Ile Ala Met Ser Phe Ala Leu Ala
370                 375                 380 ggc ctg aag atc ggc ggc att acc att ctc gac ccc gac tgc gtc gcc      1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc      1248
Lys Thr Phe Pro Ser Tyr Trp Asn Val Leu Ser Ser Leu Gly Val Ala
                405                 410                 415 tac gaa gac                                                          1257
Tyr Glu Asp <210> SEQ ID NO 8
<211> LENGTH: 419
<212> TYPE: PRT
<213> ORGANISM: Brevundomonas vesicularis

<400> SEQUENCE: 8

Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Asp Thr Thr Phe Ile Val Lys
65                  70                  75                  80

Gly Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Asp Leu Thr Val
        195                 200                 205

Ala Ala Met Arg Ala Phe Gly Ala Lys Val Glu Arg Val Ser Pro Val
    210                 215                 220

Ala Trp Arg Val Glu Pro Thr Gly Tyr His Ala Ala Asp Phe Val Ile
225                 230                 235                 240

Glu Pro Asp Ala Ser Ala Ala Thr Tyr Leu Trp Ala Ala Glu Val Leu
                245                 250                 255

Ser Gly Gly Lys Ile Asp Leu Gly Thr Pro Ala Glu Gln Phe Ser Gln
```

-continued

```
            260                 265                 270

Pro Asp Ala Lys Ala Tyr Asp Leu Ile Ser Lys Phe Pro His Leu Pro
        275                 280                 285
Ala Val Ile Asp Gly Ser Gln Met Gln Asp Ala Ile Pro Thr Leu Ala
    290                 295                 300

Val Leu Ala Ala Phe Asn Glu Met Pro Val Arg Phe Val Gly Ile Glu
305                 310                 315                 320
Asn Leu Arg Val Lys Glu Cys Asp Arg Ile Arg Ala Leu Ser Ser Gly
                325                 330                 335
Leu Ser Arg Ile Val Pro Asn Leu Gly Thr Glu Glu Gly Asp Asp Leu
            340                 345                 350
Ile Ile Ala Ser Asp Pro Ser Leu Ala Gly Lys Ile Leu Thr Ala Glu
        355                 360                 365

Ile Asp Ser Phe Ala Asp His Arg Ile Ala Met Ser Phe Ala Leu Ala
    370                 375                 380

Gly Leu Lys Ile Gly Gly Ile Thr Ile Leu Asp Pro Asp Cys Val Ala
385                 390                 395                 400
Lys Thr Phe Pro Ser Tyr Trp Asn Val Leu Ser Ser Leu Gly Val Ala
                405                 410                 415
Tyr Glu Asp

<210> SEQ ID NO 9
<211> LENGTH: 1385
<212> TYPE: DNA
<213> ORGANISM: Ochrobactrum/Brucella
<220> FEATURE:
<221> NAME/KEY: CDS
<222> LOCATION: (142)...(1380)

<400> SEQUENCE: 9
gcgcatgcca ataaataacg cagatcaccc actcactcga caagcatggc gtgtttgcct      60
gatgattcgg gtccgcacgt cggccactcc acgccacctt gccttgacca ggagccttgt     120
accttgagtt cgcagaaaac c gtg acc gtt aca ccg ccc aac ttc ccc ctc      171
                        Val Thr Val Thr Pro Pro Asn Phe Pro Leu
                          1               5                  10 act ggc aag gtc gcg ccc ccc ggc tcc aaa tcc att acc aac cgt gcg      219
Thr Gly Lys Val Ala Pro Pro Gly Ser Lys Ser Ile Thr Asn Arg Ala
                15                  20                  25 ctg ttg ctc gcg gca ctg gcc aag ggc acc agc cgt ttg agc ggt gcg      267
Leu Leu Leu Ala Ala Leu Ala Lys Gly Thr Ser Arg Leu Ser Gly Ala
            30                  35                  40 ctc aaa agc gat gac acg cgc cac atg tcg gtc gcc ctg cgg cag atg      315
Leu Lys Ser Asp Asp Thr Arg His Met Ser Val Ala Leu Arg Gln Met
        45                  50                  55 ggc gtc acc atc gac gag ccg gac gac acc acc ttt gtc gtc acc agc      363
Gly Val Thr Ile Asp Glu Pro Asp Asp Thr Thr Phe Val Val Thr Ser
     60                  65                  70 caa ggc tcg ctg caa ttg ccg gcc cag ccg ttg ttc ctc ggc aac gcc      411
Gln Gly Ser Leu Gln Leu Pro Ala Gln Pro Leu Phe Leu Gly Asn Ala
 75                  80                  85                  90 ggc acc gcc atg cgc ttt ctc acg gct gcc gtc gcc acc gtg caa ggc      459
Gly Thr Ala Met Arg Phe Leu Thr Ala Ala Val Ala Thr Val Gln Gly
                95                 100                 105 acc gtg gta ctg gac ggt gac gag tac atg caa aaa cgc ccg atc ggc      507
Thr Val Val Leu Asp Gly Asp Glu Tyr Met Gln Lys Arg Pro Ile Gly
            110                 115                 120 ccg ctg ctg gcc acc ctg ggc cag aac ggc atc cag gtc gac agc ccc      555

```
Pro Leu Leu Ala Thr Leu Gly Gln Asn Gly Ile Gln Val Asp Ser Pro
        125                 130                 135 acc ggt tgc cca ccg gta acg gtg cat ggc gcg ggc aag gtc cag gcc      603
Thr Gly Cys Pro Pro Val Thr Val His Gly Ala Gly Lys Val Gln Ala
            140                 145                 150 agg cgt ttt gag att gac gga ggc ttg tcc agc cag tac gta tcg gcc      651
Arg Arg Phe Glu Ile Asp Gly Gly Leu Ser Ser Gln Tyr Val Ser Ala
155                 160                 165                 170 ctg ctg atg ctg gcg gcg tgc ggc gaa gca ccg att gaa gtg gcg ctg      699
Leu Leu Met Leu Ala Ala Cys Gly Glu Ala Pro Ile Glu Val Ala Leu
                175                 180                 185 acc ggc aag gac atc ggc gcc cgt ggc tat gtg gac ctg acc ctc gat      747
Thr Gly Lys Asp Ile Gly Ala Arg Gly Tyr Val Asp Leu Thr Leu Asp
            190                 195                 200 tgc atg cgt gcg ttc ggg gcc cag gta gac atc gtg gac gac acc acc      795
Cys Met Arg Ala Phe Gly Ala Gln Val Asp Ile Val Asp Asp Thr Thr
        205                 210                 215 tgg cgc gtg gcc ccc acg ggc tat acc gcc cat gat tac ctg atc gaa      843
Trp Arg Val Ala Pro Thr Gly Tyr Thr Ala His Asp Tyr Leu Ile Glu
    220                 225                 230 ccc gac gct tcc gcc gcc act tac ctg tgg gcc gca gaa gta ctg acc      891
Pro Asp Ala Ser Ala Ala Thr Tyr Leu Trp Ala Ala Glu Val Leu Thr
235                 240                 245                 250 ggt ggc cgt atc gat att ggt gta gcc gcg cag gac ttc acc cag ccc      939
Gly Gly Arg Ile Asp Ile Gly Val Ala Ala Gln Asp Phe Thr Gln Pro
                255                 260                 265 gac gcc aag gca cag gcc gtg atc gcg caa ttc ccg aac atg cag gcc      987
Asp Ala Lys Ala Gln Ala Val Ile Ala Gln Phe Pro Asn Met Gln Ala
            270                 275                 280 acg gtg gtg ggt tca caa atg cag gat gcg atc ccg acc ctg gcg gtg     1035
Thr Val Val Gly Ser Gln Met Gln Asp Ala Ile Pro Thr Leu Ala Val
        285                 290                 295 ctc gcc gca ttc aac aat acc ccg gtg cgc ttc act gaa ctg gcg aac     1083
Leu Ala Ala Phe Asn Asn Thr Pro Val Arg Phe Thr Glu Leu Ala Asn
    300                 305                 310 ctg cgc gtc aag gaa tgt gac cgc gtg cag gcg ctg cac gat ggc ctc     1131
Leu Arg Val Lys Glu Cys Asp Arg Val Gln Ala Leu His Asp Gly Leu
315                 320                 325                 330 aac gaa att cgc ccg ggc ctg gcg acc atc gaa ggt gat gac ctg ctg     1179
Asn Glu Ile Arg Pro Gly Leu Ala Thr Ile Glu Gly Asp Asp Leu Leu
                335                 340                 345 gtt gcc agc gac ccc gct ttg gct ggc acc gcc tgc acc gca ctg atc     1227
Val Ala Ser Asp Pro Ala Leu Ala Gly Thr Ala Cys Thr Ala Leu Ile
            350                 355                 360 gat acc cac gcc gac cat cgc atc gcc atg tgc ttt gcc ctg gcc ggg     1275
Asp Thr His Ala Asp His Arg Ile Ala Met Cys Phe Ala Leu Ala Gly
        365                 370                 375 ctg aaa gtc tcg ggc att cgc atc caa gac cct gat tgc gta gcc aag     1323
Leu Lys Val Ser Gly Ile Arg Ile Gln Asp Pro Asp Cys Val Ala Lys
    380                 385                 390 acc tac cct gac tac tgg aaa gcg ctg gcc agc ctg ggc gtt cac tta     1371
Thr Tyr Pro Asp Tyr Trp Lys Ala Leu Ala Ser Leu Gly Val His Leu
395                 400                 405                 410 agc tac tga cacac                                                   1385
Ser Tyr *

<210> SEQ ID NO 10
<211> LENGTH: 444
<212> TYPE: PRT
<213> ORGANISM: Ochrobactrum/Brucella
```

<400> SEQUENCE: 10

```
Met Ala Cys Leu Pro Asp Asp Ser Gly Pro His Val Gly His Ser Thr
 1               5                  10                  15

Pro Pro Cys Leu Asp Gln Glu Pro Cys Thr Leu Ser Ser Gln Lys Thr
            20                  25                  30

Val Thr Val Thr Pro Pro Asn Phe Pro Leu Thr Gly Lys Val Ala Pro
        35                  40                  45

Pro Gly Ser Lys Ser Ile Thr Asn Arg Ala Leu Leu Ala Ala Leu
    50                  55                  60

Ala Lys Gly Thr Ser Arg Leu Ser Gly Ala Leu Lys Ser Asp Asp Thr
 65                  70                  75                  80

Arg His Met Ser Val Ala Leu Arg Gln Met Gly Val Thr Ile Asp Glu
                 85                  90                  95

Pro Asp Asp Thr Thr Phe Val Val Thr Ser Gln Gly Ser Leu Gln Leu
            100                 105                 110

Pro Ala Gln Pro Leu Phe Leu Gly Asn Ala Gly Thr Ala Met Arg Phe
        115                 120                 125

Leu Thr Ala Ala Val Ala Thr Val Gln Gly Thr Val Val Leu Asp Gly
130                 135                 140

Asp Glu Tyr Met Gln Lys Arg Pro Ile Gly Pro Leu Ala Thr Leu
145                 150                 155                 160

Gly Gln Asn Gly Ile Gln Val Asp Ser Pro Thr Gly Cys Pro Pro Val
                165                 170                 175

Thr Val His Gly Ala Gly Lys Val Gln Ala Arg Arg Phe Glu Ile Asp
            180                 185                 190

Gly Gly Leu Ser Ser Gln Tyr Val Ser Ala Leu Leu Met Leu Ala Ala
        195                 200                 205

Cys Gly Glu Ala Pro Ile Glu Val Ala Leu Thr Gly Lys Asp Ile Gly
    210                 215                 220

Ala Arg Gly Tyr Val Asp Leu Thr Leu Asp Cys Met Arg Ala Phe Gly
225                 230                 235                 240

Ala Gln Val Asp Ile Val Asp Asp Thr Thr Trp Arg Val Ala Pro Thr
                245                 250                 255

Gly Tyr Thr Ala His Asp Tyr Leu Ile Glu Pro Asp Ala Ser Ala Ala
            260                 265                 270

Thr Tyr Leu Trp Ala Ala Glu Val Leu Thr Gly Gly Arg Ile Asp Ile
        275                 280                 285

Gly Val Ala Ala Gln Asp Phe Thr Gln Pro Asp Ala Lys Ala Gln Ala
    290                 295                 300

Val Ile Ala Gln Phe Pro Asn Met Gln Ala Thr Val Val Gly Ser Gln
305                 310                 315                 320

Met Gln Asp Ala Ile Pro Thr Leu Ala Val Leu Ala Ala Phe Asn Asn
                325                 330                 335

Thr Pro Val Arg Phe Thr Glu Leu Ala Asn Leu Arg Val Lys Glu Cys
            340                 345                 350

Asp Arg Val Gln Ala Leu His Asp Gly Leu Asn Glu Ile Arg Pro Gly
        355                 360                 365

Leu Ala Thr Ile Glu Gly Asp Asp Leu Leu Val Ala Ser Asp Pro Ala
    370                 375                 380

Leu Ala Gly Thr Ala Cys Thr Ala Leu Ile Asp Thr His Ala Asp His
385                 390                 395                 400

Arg Ile Ala Met Cys Phe Ala Leu Ala Gly Leu Lys Val Ser Gly Ile
```

-continued

```
                        405                     410                     415
        Arg Ile Gln Asp Pro Asp Cys Val Ala Lys Thr Tyr Pro Asp Tyr Trp
                    420                     425                     430

Lys Ala Leu Ala Ser Leu Gly Val His Leu Ser Tyr
                    435                     440

<210> SEQ ID NO 11
<211> LENGTH: 1278
<212> TYPE: DNA
<213> ORGANISM: Unknown
<220> FEATURE:
<223> OTHER INFORMATION: Isolated from soil sample
<220> FEATURE:
<221> NAME/KEY: CDS
<222> LOCATION: (1)...(1278)

<400> SEQUENCE: 11 atg atc gaa ctg acc atc acc ccg ccc ggc cac ccg ctt tcc ggc aag      48
Met Ile Glu Leu Thr Ile Thr Pro Pro Gly His Pro Leu Ser Gly Lys
  1               5                  10                  15 gtg gag ccg ccc ggt tcc aaa tcc att acc aac cgt gca ctt ctg ctg      96
Val Glu Pro Pro Gly Ser Lys Ser Ile Thr Asn Arg Ala Leu Leu Leu
             20                  25                  30 gcc ggg ctc gcc aag ggc aaa agc cgt ctc acg ggc gcg ctg aaa agc     144
Ala Gly Leu Ala Lys Gly Lys Ser Arg Leu Thr Gly Ala Leu Lys Ser
         35                  40                  45 gac gat acg ctt tac atg gca gaa gcg ctg cgt gag atg ggt gtc aag     192
Asp Asp Thr Leu Tyr Met Ala Glu Ala Leu Arg Glu Met Gly Val Lys
     50                  55                  60 gta acc gag cct gac gcg acc acc ttc gtg gtg gag agt tca ggt ggg     240
Val Thr Glu Pro Asp Ala Thr Thr Phe Val Val Glu Ser Ser Gly Gly
 65                  70                  75                  80 ttg cat cag ccg gaa aag ccg ctt ttc ctc ggc aat gcc ggc aca gct     288
Leu His Gln Pro Glu Lys Pro Leu Phe Leu Gly Asn Ala Gly Thr Ala
                 85                  90                  95 acc cgc ttt ctc acc gcc gct gcc gcc ctt gtg gat ggc gcc gtc atc     336
Thr Arg Phe Leu Thr Ala Ala Ala Ala Leu Val Asp Gly Ala Val Ile
            100                 105                 110 atc gat ggc gac gag cat atg cgc aaa cgc ccg atc atg ccg ctg gtg     384
Ile Asp Gly Asp Glu His Met Arg Lys Arg Pro Ile Met Pro Leu Val
        115                 120                 125 gaa gcc ctg cgc tcc ctc ggc gtt gag gcg gag gcg ccg acc ggc tgc     432
Glu Ala Leu Arg Ser Leu Gly Val Glu Ala Glu Ala Pro Thr Gly Cys
    130                 135                 140 ccg ccc gtc acc gtc tgc ggt aag ggt act ggc ttc ccg aag ggc agc     480
Pro Pro Val Thr Val Cys Gly Lys Gly Thr Gly Phe Pro Lys Gly Ser
145                 150                 155                 160 gtc acg atc gac gcc aac ctt tcc agc cag tat gtg tcc gca ctt ctg     528
Val Thr Ile Asp Ala Asn Leu Ser Ser Gln Tyr Val Ser Ala Leu Leu
                165                 170                 175 atg gcc gcc gcc tgc ggc gac aag cct gtc gat atc atc ctc aaa ggt     576
Met Ala Ala Ala Cys Gly Asp Lys Pro Val Asp Ile Ile Leu Lys Gly
            180                 185                 190 gag gaa atc ggc gcg aag ggc tat atc gat ctc acc aca tcg gcc atg     624
Glu Glu Ile Gly Ala Lys Gly Tyr Ile Asp Leu Thr Thr Ser Ala Met
        195                 200                 205 gaa gcc ttc ggc gca aag gtg gag cgg gtc agc aac gcc atc tgg cgc     672
Glu Ala Phe Gly Ala Lys Val Glu Arg Val Ser Asn Ala Ile Trp Arg
    210                 215                 220 gtg cat ccg acc ggc tac acg gcg acc gat ttc cat atc gag ccg gat     720
Val His Pro Thr Gly Tyr Thr Ala Thr Asp Phe His Ile Glu Pro Asp
```

-continued

```
                 225                 230                 235                 240
gcc tcg gcc gcc acc tat ctc tgg ggc gct gag ctt ttg acc ggc ggc      768
Ala Ser Ala Ala Thr Tyr Leu Trp Gly Ala Glu Leu Leu Thr Gly Gly
                245                 250                 255 gcc atc gat atc ggt acg ccg gcc gac aag ttc acc cag ccg gat gcc      816
Ala Ile Asp Ile Gly Thr Pro Ala Asp Lys Phe Thr Gln Pro Asp Ala
                260                 265                 270 aag gcc cat gag gtc atg gcg caa ttt ccg cat ctg ccc gcc gaa atc      864
Lys Ala His Glu Val Met Ala Gln Phe Pro His Leu Pro Ala Glu Ile
            275                 280                 285 gac ggt tcg cag atg cag gat gcc att ccc acc att gcc gtt ctc gcc      912
Asp Gly Ser Gln Met Gln Asp Ala Ile Pro Thr Ile Ala Val Leu Ala
        290                 295                 300 gcc ttt aac gaa acg ccg gtg cgt ttc gtc ggc atc gcc aat ctg cgc      960
Ala Phe Asn Glu Thr Pro Val Arg Phe Val Gly Ile Ala Asn Leu Arg
305                 310                 315                 320 gtc aag gag tgc gac cga atc cgc gcc gtc tca ctc ggc ctc aac gaa     1008
Val Lys Glu Cys Asp Arg Ile Arg Ala Val Ser Leu Gly Leu Asn Glu
                325                 330                 335 atc cgc gat ggt ctg gcg cat gag gaa ggc gac gac ttg atc gtg cat     1056
Ile Arg Asp Gly Leu Ala His Glu Glu Gly Asp Asp Leu Ile Val His
            340                 345                 350 tcc gat cct tcg ctt gcg ggc cag acg gtg aat gcc tcc atc gac act     1104
Ser Asp Pro Ser Leu Ala Gly Gln Thr Val Asn Ala Ser Ile Asp Thr
        355                 360                 365 ttc gcc gac cac cgt atc gcc atg agc ttt gcg ctg gcg gcg ctg aag     1152
Phe Ala Asp His Arg Ile Ala Met Ser Phe Ala Leu Ala Ala Leu Lys
    370                 375                 380 atc ggc ggc att gcc atc cag aat ccg gcc tgc gtg ggc aag acc tat     1200
Ile Gly Gly Ile Ala Ile Gln Asn Pro Ala Cys Val Gly Lys Thr Tyr
385                 390                 395                 400 ccc ggt tac tgg aag gcg ctc gcc tcg ctg gga gtc gaa tac tcg gaa     1248
Pro Gly Tyr Trp Lys Ala Leu Ala Ser Leu Gly Val Glu Tyr Ser Glu
                405                 410                 415 aag gaa acc gct gcc gag ccg cag cat tag                             1278
Lys Glu Thr Ala Ala Glu Pro Gln His *
            420                 425
```

<210> SEQ ID NO 12
<211> LENGTH: 425
<212> TYPE: PRT
<213> ORGANISM: Unknown
<220> FEATURE:
<223> OTHER INFORMATION: Isolated from soil sample

<400> SEQUENCE: 12

```
Met Ile Glu Leu Thr Ile Thr Pro Pro Gly His Pro Leu Ser Gly Lys
 1               5                  10                  15

Val Glu Pro Pro Gly Ser Lys Ser Ile Thr Asn Arg Ala Leu Leu Leu
            20                  25                  30

Ala Gly Leu Ala Lys Gly Lys Ser Arg Leu Thr Gly Ala Leu Lys Ser
        35                  40                  45

Asp Asp Thr Leu Tyr Met Ala Glu Ala Leu Arg Glu Met Gly Val Lys
    50                  55                  60

Val Thr Glu Pro Asp Ala Thr Thr Phe Val Val Glu Ser Ser Gly Gly
65                  70                  75                  80

Leu His Gln Pro Glu Lys Pro Leu Phe Leu Gly Asn Ala Gly Thr Ala
                85                  90                  95

Thr Arg Phe Leu Thr Ala Ala Ala Ala Leu Val Asp Gly Ala Val Ile
```

```
                    100                 105                 110
Ile Asp Gly Asp Glu His Met Arg Lys Arg Pro Ile Met Pro Leu Val
            115                 120                 125
Glu Ala Leu Arg Ser Leu Gly Val Glu Ala Glu Ala Pro Thr Gly Cys
            130                 135                 140
Pro Pro Val Thr Val Cys Gly Lys Gly Thr Gly Phe Pro Lys Gly Ser
145                 150                 155                 160
Val Thr Ile Asp Ala Asn Leu Ser Ser Gln Tyr Val Ser Ala Leu Leu
                165                 170                 175
Met Ala Ala Ala Cys Gly Asp Lys Pro Val Asp Ile Ile Leu Lys Gly
            180                 185                 190
Glu Glu Ile Gly Ala Lys Gly Tyr Ile Asp Leu Thr Thr Ser Ala Met
            195                 200                 205
Glu Ala Phe Gly Ala Lys Val Glu Arg Val Ser Asn Ala Ile Trp Arg
            210                 215                 220
Val His Pro Thr Gly Tyr Thr Ala Thr Asp Phe His Ile Glu Pro Asp
225                 230                 235                 240
Ala Ser Ala Ala Thr Tyr Leu Trp Gly Ala Glu Leu Leu Thr Gly Gly
                245                 250                 255
Ala Ile Asp Ile Gly Thr Pro Ala Asp Lys Phe Thr Gln Pro Asp Ala
            260                 265                 270
Lys Ala His Glu Val Met Ala Gln Phe Pro His Leu Pro Ala Glu Ile
            275                 280                 285
Asp Gly Ser Gln Met Gln Asp Ala Ile Pro Thr Ile Ala Val Leu Ala
            290                 295                 300
Ala Phe Asn Glu Thr Pro Val Arg Phe Val Gly Ile Ala Asn Leu Arg
305                 310                 315                 320
Val Lys Glu Cys Asp Arg Ile Arg Ala Val Ser Leu Gly Leu Asn Glu
                325                 330                 335
Ile Arg Asp Gly Leu Ala His Glu Gly Asp Asp Leu Ile Val His
            340                 345                 350
Ser Asp Pro Ser Leu Ala Gly Gln Thr Val Asn Ala Ser Ile Asp Thr
            355                 360                 365
Phe Ala Asp His Arg Ile Ala Met Ser Phe Ala Leu Ala Ala Leu Lys
            370                 375                 380
Ile Gly Gly Ile Ala Ile Gln Asn Pro Ala Cys Val Gly Lys Thr Tyr
385                 390                 395                 400
Pro Gly Tyr Trp Lys Ala Leu Ala Ser Leu Gly Val Gly Tyr Ser Glu
                405                 410                 415
Lys Glu Thr Ala Ala Glu Pro Gln His
            420                 425

<210> SEQ ID NO 13
<211> LENGTH: 17
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 5
<223> OTHER INFORMATION: Xaa= Lys or Thr
<220> FEATURE:
<221> NAME/KEY: VARIANT
<222> LOCATION: 7
<223> OTHER INFORMATION: Xaa= Arg or His
<220> FEATURE:
<221> NAME/KEY: VARIANT
```

```
<222> LOCATION: 9
<223> OTHER INFORMATION: Xaa= Ser or Thr

<400> SEQUENCE: 13

Leu Ala Lys Gly Xaa Ser Xaa Leu Xaa Gly Ala Leu Lys Ser Asp Asp
 1               5                  10                  15

Thr

<210> SEQ ID NO 14
<211> LENGTH: 5
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 5
<223> OTHER INFORMATION: Xaa= Lys or Thr

<400> SEQUENCE: 14

Leu Ala Lys Gly Xaa
 1               5

<210> SEQ ID NO 15
<211> LENGTH: 4
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 2
<223> OTHER INFORMATION: Xaa= Arg or His
<220> FEATURE:
<221> NAME/KEY: VARIANT
<222> LOCATION: 4
<223> OTHER INFORMATION: Xaa= Ser or Thr

<400> SEQUENCE: 15

Ser Xaa Leu Xaa
 1

<210> SEQ ID NO 16
<211> LENGTH: 8
<212> TYPE: PRT
<213> ORGANISM: Artificial Sequence
<220> FEATURE:
<223> OTHER INFORMATION: Conserved Domains

<400> SEQUENCE: 16

Gly Ala Leu Lys Ser Asp Asp Thr
 1               5

<210> SEQ ID NO 17
<211> LENGTH: 13
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 4
<223> OTHER INFORMATION: Xaa= Asp or Ala
<220> FEATURE:
<221> NAME/KEY: VARIANT
<222> LOCATION: 5
<223> OTHER INFORMATION: Xaa= Ser or Thr
<220> FEATURE:
<221> NAME/KEY: VARIANT
<222> LOCATION: 8
```

```
<223> OTHER INFORMATION: Xaa= Val or Ile
<220> FEATURE:
<221> NAME/KEY: VARIANT
<222> LOCATION: 10
<223> OTHER INFORMATION: Xaa= Thr, Glu or Lys
<220> FEATURE:
<221> NAME/KEY: VARIANT
<222> LOCATION: 11
<223> OTHER INFORMATION: Xaa= Ser or Gly
<220> FEATURE:
<221> NAME/KEY: VARIANT
<222> LOCATION: (12)...(0)
<223> OTHER INFORMATION: Xaa= Gln, Ser, Glu or Thr

<400> SEQUENCE: 17

Glu Pro Asp Xaa Xaa Thr Phe Xaa Val Xaa Xaa Xaa Gly
 1               5                  10

<210> SEQ ID NO 18
<211> LENGTH: 9
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 4
<223> OTHER INFORMATION: Xaa= Asp or Ala
<220> FEATURE:
<221> NAME/KEY: VARIANT
<222> LOCATION: 5
<223> OTHER INFORMATION: Xaa= Ser or Thr
<220> FEATURE:
<221> NAME/KEY: VARIANT
<222> LOCATION: 8
<223> OTHER INFORMATION: Xaa= Val or Ile

<400> SEQUENCE: 18

Glu Pro Asp Xaa Xaa Thr Phe Xaa Val
 1               5

<210> SEQ ID NO 19
<211> LENGTH: 4
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 1
<223> OTHER INFORMATION: Xaa= Thr, Glu or Lys
<220> FEATURE:
<221> NAME/KEY: VARIANT
<222> LOCATION: 2
<223> OTHER INFORMATION: Xaa= Ser or Gly
<220> FEATURE:
<221> NAME/KEY: VARIANT
<222> LOCATION: 3
<223> OTHER INFORMATION: Xaa= Gln, Ser, Glu or Thr

<400> SEQUENCE: 19

Xaa Xaa Xaa Gly
 1

<210> SEQ ID NO 20
<211> LENGTH: 6
<212> TYPE: PRT
<213> ORGANISM: Artificial Sequence
<220> FEATURE:
<223> OTHER INFORMATION: Conserved Domains

<400> SEQUENCE: 20
```

Arg Phe Leu Thr Ala Ala
1               5

<210> SEQ ID NO 21
<211> LENGTH: 6
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 5
<223> OTHER INFORMATION: Xaa= Gly, Met or Leu

<400> SEQUENCE: 21

Lys Arg Pro Ile Xaa Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 1
<223> OTHER INFORMATION: Xaa= Thr or Ser

<400> SEQUENCE: 22

Xaa Gly Cys Pro Pro Val
1               5

<210> SEQ ID NO 23
<211> LENGTH: 10
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 4
<223> OTHER INFORMATION: Xaa= Arg, Lys or Leu
<220> FEATURE:
<221> NAME/KEY: VARIANT
<222> LOCATION: 7
<223> OTHER INFORMATION: Xaa= Ile or Val

<400> SEQUENCE: 23

Ile Gly Ala Xaa Gly Tyr Xaa Asp Leu Thr
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 2
<223> OTHER INFORMATION: Xaa= Arg or Lys
<220> FEATURE:
<221> NAME/KEY: VARIANT
<222> LOCATION: 4
<223> OTHER INFORMATION: Xaa= Ala, HIs, Glu or Ser
<220> FEATURE:
<221> NAME/KEY: VARIANT
<222> LOCATION: 5
<223> OTHER INFORMATION: Xaa= Pro or Ala

<400> SEQUENCE: 24

```
Trp Xaa Val Xaa Xaa Thr Gly
 1               5
```

<210> SEQ ID NO 25
<211> LENGTH: 16
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 12
<223> OTHER INFORMATION: Xaa= Ala or Gly
<220> FEATURE:
<221> NAME/KEY: VARIANT
<222> LOCATION: 14
<223> OTHER INFORMATION: Xaa= Glu or Gln
<220> FEATURE:
<221> NAME/KEY: VARIANT
<222> LOCATION: 15
<223> OTHER INFORMATION: Xaa= Val, Leu or Ala

<400> SEQUENCE: 25

```
Glu Pro Asp Ala Ser Ala Ala Thr Tyr Leu Trp Xaa Ala Xaa Xaa Leu
 1               5                  10                  15
```

<210> SEQ ID NO 26
<211> LENGTH: 11
<212> TYPE: PRT
<213> ORGANISM: Artificial Sequence
<220> FEATURE:
<223> OTHER INFORMATION: Conserved Domains

<400> SEQUENCE: 26

```
Glu Pro Asp Ala Ser Ala Ala Thr Tyr Leu Trp
 1               5                  10
```

<210> SEQ ID NO 27
<211> LENGTH: 4
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 3
<223> OTHER INFORMATION: Xaa= Ile or Leu

<400> SEQUENCE: 27

```
Ile Asp Xaa Gly
 1
```

<210> SEQ ID NO 28
<211> LENGTH: 8
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 2
<223> OTHER INFORMATION: Xaa= Thr or Ser

<400> SEQUENCE: 28

```
Phe Xaa Gln Pro Asp Ala Lys Ala
 1               5
```

<210> SEQ ID NO 29
<211> LENGTH: 28

```
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 1
<223> OTHER INFORMATION: Xaa= Glu, Lys or Ser
<220> FEATURE:
<221> NAME/KEY: VARIANT
<222> LOCATION: 4
<223> OTHER INFORMATION: Xaa= Asp or His
<220> FEATURE:
<221> NAME/KEY: VARIANT
<222> LOCATION: 5
<223> OTHER INFORMATION: Xaa= Met or Leu
<220> FEATURE:
<221> NAME/KEY: VARIANT
<222> LOCATION: 6
<223> OTHER INFORMATION: Xaa= Pro or Gln
<220> FEATURE:
<221> NAME/KEY: VARIANT
<222> LOCATION: 8
<223> OTHER INFORMATION: Xaa= Thr, Glu or Val
<220> FEATURE:
<221> NAME/KEY: VARIANT
<222> LOCATION: (9)...(0)
<223> OTHER INFORMATION: Xaa= Val or Ile
<220> FEATURE:
<221> NAME/KEY: VARIANT
<222> LOCATION: (10)...(0)
<223> OTHER INFORMATION: Xaa= Asp or Val
<220> FEATURE:
<221> NAME/KEY: VARIANT
<222> LOCATION: (21)...(0)
<223> OTHER INFORMATION: Xaa= Leu or Ile
<220> FEATURE:
<221> NAME/KEY: VARIANT
<222> LOCATION: (24)...(0)
<223> OTHER INFORMATION: Xaa= Leu or Ile

<400> SEQUENCE: 29

Xaa Phe Pro Xaa Xaa Xaa Ala Xaa Xaa Xaa Gly Ser Gln Met Gln Asp
 1               5                  10                  15

Ala Ile Pro Thr Xaa Ala Val Xaa Ala Ala Phe Asn
             20                  25

<210> SEQ ID NO 30
<211> LENGTH: 7
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 1
<223> OTHER INFORMATION: Xaa= Gln, Lys or Ser
<220> FEATURE:
<221> NAME/KEY: VARIANT
<222> LOCATION: 4
<223> OTHER INFORMATION: Xaa= Asp or His
<220> FEATURE:
<221> NAME/KEY: VARIANT
<222> LOCATION: 5
<223> OTHER INFORMATION: Xaa= Met or Leu
<220> FEATURE:
<221> NAME/KEY: VARIANT
<222> LOCATION: 6
<223> OTHER INFORMATION: Xaa= Pro or Gln

<400> SEQUENCE: 30

Xaa Phe Pro Xaa Xaa Xaa Ala
 1               5
```

```
<210> SEQ ID NO 31
<211> LENGTH: 21
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 1
<223> OTHER INFORMATION: Xaa= Thr, Glu, or Val
<220> FEATURE:
<221> NAME/KEY: VARIANT
<222> LOCATION: 2
<223> OTHER INFORMATION: Xaa= Val or Ile
<220> FEATURE:
<221> NAME/KEY: VARIANT
<222> LOCATION: 3
<223> OTHER INFORMATION: Xaa= Asp or Val
<220> FEATURE:
<221> NAME/KEY: VARIANT
<222> LOCATION: 14
<223> OTHER INFORMATION: Xaa= Leu or Ile
<220> FEATURE:
<221> NAME/KEY: VARIANT
<222> LOCATION: 17
<223> OTHER INFORMATION: Xaa= Leu or Ile

<400> SEQUENCE: 31

Xaa Xaa Xaa Gly Ser Gln Met Gln Asp Ala Ile Pro Thr Xaa Ala Val
 1               5                  10                  15

Xaa Ala Ala Phe Asn
            20

<210> SEQ ID NO 32
<211> LENGTH: 10
<212> TYPE: PRT
<213> ORGANISM: Artificial Sequence
<220> FEATURE:
<223> OTHER INFORMATION: Conserved Domains

<400> SEQUENCE: 32

Gly Ser Gln Met Gln Asp Ala Ile Pro Thr
 1               5                  10

<210> SEQ ID NO 33
<211> LENGTH: 18
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 5
<223> OTHER INFORMATION: Xaa= Val or Thr
<220> FEATURE:
<221> NAME/KEY: VARIANT
<222> LOCATION: 6
<223> OTHER INFORMATION: Xaa= Glu or Gly
<220> FEATURE:
<221> NAME/KEY: VARIANT
<222> LOCATION: 7
<223> OTHER INFORMATION: Xaa= Leu or Ile
<220> FEATURE:
<221> NAME/KEY: VARIANT
<222> LOCATION: 8
<223> OTHER INFORMATION: Xaa= Ala or Glu
<220> FEATURE:
<221> NAME/KEY: VARIANT
<222> LOCATION: 17
<223> OTHER INFORMATION: Xaa= Ile or Val

<400> SEQUENCE: 33

Pro Val Arg Phe Xaa Xaa Xaa Xaa Asn Leu Arg Val Lys Glu Cys Asp
```

```
                1               5                  10                  15

Arg Xaa

<210> SEQ ID NO 34
<211> LENGTH: 4
<212> TYPE: PRT
<213> ORGANISM: Artificial Sequence
<220> FEATURE:
<223> OTHER INFORMATION: Conserved Domains

<400> SEQUENCE: 34

Pro Val Arg Phe
 1

<210> SEQ ID NO 35
<211> LENGTH: 14
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 1
<223> OTHER INFORMATION: Xaa= Val or Thr
<220> FEATURE:
<221> NAME/KEY: VARIANT
<222> LOCATION: 2
<223> OTHER INFORMATION: Xaa= Glu or Gly
<220> FEATURE:
<221> NAME/KEY: VARIANT
<222> LOCATION: 3
<223> OTHER INFORMATION: Xaa= Leu or Ile
<220> FEATURE:
<221> NAME/KEY: VARIANT
<222> LOCATION: 4
<223> OTHER INFORMATION: Xaa= ala or Glu
<220> FEATURE:
<221> NAME/KEY: VARIANT
<222> LOCATION: 14
<223> OTHER INFORMATION: Xaa= Ile or Val

<400> SEQUENCE: 35

Xaa Xaa Xaa Xaa Asn Leu Arg Val Lys Glu Cys Asp Arg Xaa
 1               5                  10

<210> SEQ ID NO 36
<211> LENGTH: 9
<212> TYPE: PRT
<213> ORGANISM: Artificial Sequence
<220> FEATURE:
<223> OTHER INFORMATION: Conserved Domains

<400> SEQUENCE: 36

Asn Leu Arg Val Lys Glu Cys Asp Arg
 1               5

<210> SEQ ID NO 37
<211> LENGTH: 7
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 6
<223> OTHER INFORMATION: Xaa= Leu or Ile
<220> FEATURE:
<221> NAME/KEY: VARIANT
<222> LOCATION: 7
<223> OTHER INFORMATION: Xaa= Val or Ile
```

```
<400> SEQUENCE: 37

Glu Gly Asp Asp Leu Xaa Xaa
 1               5

<210> SEQ ID NO 38
<211> LENGTH: 6
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 1
<223> OTHER INFORMATION: Xaa= Asp or Asn
<220> FEATURE:
<221> NAME/KEY: VARIANT
<222> LOCATION: 3
<223> OTHER INFORMATION: Xaa= Ala, Ser or Thr

<400> SEQUENCE: 38

Xaa Pro Xaa Leu Ala Gly
 1               5

<210> SEQ ID NO 39
<211> LENGTH: 10
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 2
<223> OTHER INFORMATION: Xaa= Leu, Ser or Glu
<220> FEATURE:
<221> NAME/KEY: VARIANT
<222> LOCATION: 5
<223> OTHER INFORMATION: Xaa= Thr or Ser
<220> FEATURE:
<221> NAME/KEY: VARIANT
<222> LOCATION: 6
<223> OTHER INFORMATION: Xaa= His or Phe
<220> FEATURE:
<221> NAME/KEY: VARIANT
<222> LOCATION: 7
<223> OTHER INFORMATION: Xaa= ala or Ser

<400> SEQUENCE: 39

Ala Xaa Ile Asp Xaa Xaa Xaa Asp His Arg
 1               5                   10

<210> SEQ ID NO 40
<211> LENGTH: 11
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 5
<223> OTHER INFORMATION: Xaa= Gly or Ala
<220> FEATURE:
<221> NAME/KEY: VARIANT
<222> LOCATION: 8
<223> OTHER INFORMATION: Xaa= Ile or Val
<220> FEATURE:
<221> NAME/KEY: VARIANT
<222> LOCATION: 9
<223> OTHER INFORMATION: Xaa= Ser, Gly, Ala or Lys

<400> SEQUENCE: 40

Phe Ala Leu Ala Xaa Leu Lys Xaa Xaa Gly Ile
 1               5                   10
```

```
<210> SEQ ID NO 41
<211> LENGTH: 7
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 5
<223> OTHER INFORMATION: Xaa= Gly or Ala

<400> SEQUENCE: 41

Phe Ala Leu Ala Xaa Leu Lys
 1               5

<210> SEQ ID NO 42
<211> LENGTH: 6
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 3
<223> OTHER INFORMATION: Xaa= Ile or Val
<220> FEATURE:
<221> NAME/KEY: VARIANT
<222> LOCATION: 4
<223> OTHER INFORMATION: Xaa= Ser, Gly, Ala or Lys

<400> SEQUENCE: 42

Leu Lys Xaa Xaa Gly Ile
 1               5

<210> SEQ ID NO 43
<211> LENGTH: 7
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 1
<223> OTHER INFORMATION: Xaa= Asn or Asp
<220> FEATURE:
<221> NAME/KEY: VARIANT
<222> LOCATION: 3
<223> OTHER INFORMATION: Xaa= Ala or Asp
<220> FEATURE:
<221> NAME/KEY: VARIANT
<222> LOCATION: 6
<223> OTHER INFORMATION: Xaa= Ala or Gly

<400> SEQUENCE: 43

Xaa Pro Xaa Cys Val Xaa Lys
 1               5

<210> SEQ ID NO 44
<211> LENGTH: 5
<212> TYPE: PRT
<213> ORGANISM: Artificial Sequence
<220> FEATURE:
<223> OTHER INFORMATION: Conserved Domains
<220> FEATURE:
<221> NAME/KEY: VARIANT
<222> LOCATION: 1
<223> OTHER INFORMATION: Xaa= Ala, Ser or Pro

<400> SEQUENCE: 44

Xaa Ser Leu Gly Val
```

<210> SEQ ID NO 45
<211> LENGTH: 1500
<212> TYPE: DNA
<213> ORGANISM: Pseudomonas syringae
<220> FEATURE:
<221> NAME/KEY: CDS
<222> LOCATION: (102)...(1358)
<220> FEATURE:
<221> NAME/KEY: misc_feature
<222> LOCATION: (0)...(0)
<223> OTHER INFORMATION: pv syringae strain B728a

<400> SEQUENCE: 45

```
gctgacccgc gcccgggctt ggcgatgaat gaaaccggca ctgcgggctt gatcccgctc        60
gtgctaggat cgcgattttt ccgctgacgc tcagggacat c atg cga cct caa gcc       116
                                             Met Arg Pro Gln Ala
                                               1               5 acc ctc act gtt ttg cct gtc gag cgc ccg ttg gtc ggg cgt gtc agc        164
Thr Leu Thr Val Leu Pro Val Glu Arg Pro Leu Val Gly Arg Val Ser
             10                  15                  20 ccg ccg ggc tcc aag tcg atc acc aac cgt gca ttg ttg ctg gcc ggg        212
Pro Pro Gly Ser Lys Ser Ile Thr Asn Arg Ala Leu Leu Leu Ala Gly
         25                  30                  35 ctg gcc aaa ggc acc agc cgc ctg acc ggc gcg ctg aag agt gat gac        260
Leu Ala Lys Gly Thr Ser Arg Leu Thr Gly Ala Leu Lys Ser Asp Asp
     40                  45                  50 acg cgc gtg atg tcc gaa gcc ttg cgt ctg atg ggc gtg cag gtc gac        308
Thr Arg Val Met Ser Glu Ala Leu Arg Leu Met Gly Val Gln Val Asp
 55                  60                  65 gag ccg gat gac agc acc ttc gtg gtc acc agc agc ggg cac tgg cag        356
Glu Pro Asp Asp Ser Thr Phe Val Val Thr Ser Ser Gly His Trp Gln
             70                  75                  80                  85 gcg ccg caa cag gcg ctg ttc ctc ggc aat gcc ggg act gcg aca cgc        404
Ala Pro Gln Gln Ala Leu Phe Leu Gly Asn Ala Gly Thr Ala Thr Arg
         90                  95                 100 ttt ctg acc gcg gca ctg gcc aac ttc gaa ggc gac ttc gtg gtg gat        452
Phe Leu Thr Ala Ala Leu Ala Asn Phe Glu Gly Asp Phe Val Val Asp
    105                 110                 115 ggc gac gaa tac atg cgc aag cgc ccg atc ggc ccg ttg gtc gat gcc        500
Gly Asp Glu Tyr Met Arg Lys Arg Pro Ile Gly Pro Leu Val Asp Ala
120                 125                 130 ttg cag cgc atg ggc gtg gag gtc agc gca ccc agt ggt tgc ccg ccg        548
Leu Gln Arg Met Gly Val Glu Val Ser Ala Pro Ser Gly Cys Pro Pro
            135                 140                 145 gtg gcc atc aag ggc aag ggc ggt ctt gag gcc ggt cgt atc gaa atc        596
Val Ala Ile Lys Gly Lys Gly Gly Leu Glu Ala Gly Arg Ile Glu Ile
150                 155                 160                 165 gac ggc aat ctg tcc agc cag tat gtg tcg gca ctg ctg atg gcc ggt        644
Asp Gly Asn Leu Ser Ser Gln Tyr Val Ser Ala Leu Leu Met Ala Gly
                170                 175                 180 gcc tgt ggc aag ggg cct gtg gaa gtt gcc ctg aca ggc agc gag atc        692
Ala Cys Gly Lys Gly Pro Val Glu Val Ala Leu Thr Gly Ser Glu Ile
            185                 190                 195 ggc gcg cgt ggt tac ctc gac ctc acg ctg gcg gcc atg cgg gcg ttc        740
Gly Ala Arg Gly Tyr Leu Asp Leu Thr Leu Ala Ala Met Arg Ala Phe
        200                 205                 210 ggt gcc gag gtt cag gcc atc ggc gac gcc gcc tgg aaa gtc tcg gct        788
Gly Ala Glu Val Gln Ala Ile Gly Asp Ala Ala Trp Lys Val Ser Ala
    215                 220                 225
```

```
acc ggt tat cgc gct acg gat ttc cac atc gaa ccg gat gcc tcg gcg      836
Thr Gly Tyr Arg Ala Thr Asp Phe His Ile Glu Pro Asp Ala Ser Ala
230                 235                 240                 245 gcc acc tac ctt tgg gct gcg cag gcc ctg acc gag ggc gct atc gac      884
Ala Thr Tyr Leu Trp Ala Ala Gln Ala Leu Thr Glu Gly Ala Ile Asp
                250                 255                 260 ctg ggc gtg gcc agc aac gcg ttc act cag cct gat gca ctg gcc agt      932
Leu Gly Val Ala Ser Asn Ala Phe Thr Gln Pro Asp Ala Leu Ala Ser
            265                 270                 275 cag atc atc gcc agc ttc ccg aac atg ccg gcc gtg atc gac ggc tcg      980
Gln Ile Ile Ala Ser Phe Pro Asn Met Pro Ala Val Ile Asp Gly Ser
        280                 285                 290 cag atg cag gac gcg att ccc acg ctg gcc gta ctg gcc gcg ttc aat     1028
Gln Met Gln Asp Ala Ile Pro Thr Leu Ala Val Leu Ala Ala Phe Asn
    295                 300                 305 cgt caa ccg gtg cgc ttt gtc ggc atc gcc aac ctg cgg gtc aag gag     1076
Arg Gln Pro Val Arg Phe Val Gly Ile Ala Asn Leu Arg Val Lys Glu
310                 315                 320                 325 tgc gac cgc atc tcg gca ctg tcc aac ggc ctg tgc gcc atc gca ccc     1124
Cys Asp Arg Ile Ser Ala Leu Ser Asn Gly Leu Cys Ala Ile Ala Pro
                330                 335                 340 ggc ctg gcg gtc gaa gag ggt gac gat ctg atc gtt acc gcc aac ccg     1172
Gly Leu Ala Val Glu Glu Gly Asp Asp Leu Ile Val Thr Ala Asn Pro
                345                 350                 355 acg ctg gca ggc act acg gtc gat gcc ttg atc gat acc cac tcc gac     1220
Thr Leu Ala Gly Thr Thr Val Asp Ala Leu Ile Asp Thr His Ser Asp
            360                 365                 370 cat cgg atc gcc atg tgc ttt gca ctg gcg ggc ctg aag att gcc ggc     1268
His Arg Ile Ala Met Cys Phe Ala Leu Ala Gly Leu Lys Ile Ala Gly
        375                 380                 385 atc cgc att ctc gac cct gat tgc gtc gcc aag acc tac ccg ggg tac     1316
Ile Arg Ile Leu Asp Pro Asp Cys Val Ala Lys Thr Tyr Pro Gly Tyr
390                 395                 400                 405 tgg gat gcg ctg gct tct ctg ggt gtg agt gtt cag cgc tga             1358
Trp Asp Ala Leu Ala Ser Leu Gly Val Ser Val Gln Arg *
                410                 415 tagatcaggt ttatcggctc gggaagcctg taggatttcg agacatcttt agctggcagt   1418
ctacggttgt agatactatg tttatacgtt ggggttgcat gcctcgtgtg aggtatctac   1478
agtattgcta cgttatgagg tg                                            1500

<210> SEQ ID NO 46
<211> LENGTH: 418
<212> TYPE: PRT
<213> ORGANISM: Pseudomonas syringae
<220> FEATURE:
<221> NAME/KEY: VARIANT
<222> LOCATION: (0)...(0)
<223> OTHER INFORMATION: pv syringae strain B728a

<400> SEQUENCE: 46

Met Arg Pro Gln Ala Thr Leu Thr Val Leu Pro Val Glu Arg Pro Leu
 1               5                  10                  15

Val Gly Arg Val Ser Pro Pro Gly Ser Lys Ser Ile Thr Asn Arg Ala
                20                  25                  30

Leu Leu Leu Ala Gly Leu Ala Lys Gly Thr Ser Arg Leu Thr Gly Ala
            35                  40                  45

Leu Lys Ser Asp Asp Thr Arg Val Met Ser Glu Ala Leu Arg Leu Met
        50                  55                  60

Gly Val Gln Val Asp Glu Pro Asp Asp Ser Thr Phe Val Val Thr Ser
```

```
                65                  70                  75                  80
Ser Gly His Trp Gln Ala Pro Gln Gln Ala Leu Phe Leu Gly Asn Ala
                    85                  90                  95
Gly Thr Ala Thr Arg Phe Leu Thr Ala Ala Leu Ala Asn Phe Glu Gly
                100                 105                 110
Asp Phe Val Val Asp Gly Asp Glu Tyr Met Arg Lys Arg Pro Ile Gly
                115                 120                 125
Pro Leu Val Asp Ala Leu Gln Arg Met Gly Val Glu Val Ser Ala Pro
            130                 135                 140
Ser Gly Cys Pro Pro Val Ala Ile Lys Gly Lys Gly Gly Leu Glu Ala
145                 150                 155                 160
Gly Arg Ile Glu Ile Asp Gly Asn Leu Ser Ser Gln Tyr Val Ser Ala
                165                 170                 175
Leu Leu Met Ala Gly Ala Cys Gly Lys Gly Pro Val Glu Val Ala Leu
            180                 185                 190
Thr Gly Ser Glu Ile Gly Ala Arg Gly Tyr Leu Asp Leu Thr Leu Ala
                195                 200                 205
Ala Met Arg Ala Phe Gly Ala Glu Val Gln Ala Ile Gly Asp Ala Ala
            210                 215                 220
Trp Lys Val Ser Ala Thr Gly Tyr Arg Ala Thr Asp Phe His Ile Glu
225                 230                 235                 240
Pro Asp Ala Ser Ala Ala Thr Tyr Leu Trp Ala Ala Gln Ala Leu Thr
                245                 250                 255
Glu Gly Ala Ile Asp Leu Gly Val Ala Ser Asn Ala Phe Thr Gln Pro
            260                 265                 270
Asp Ala Leu Ala Ser Gln Ile Ile Ala Ser Phe Pro Asn Met Pro Ala
            275                 280                 285
Val Ile Asp Gly Ser Gln Met Gln Asp Ala Ile Pro Thr Leu Ala Val
        290                 295                 300
Leu Ala Ala Phe Asn Arg Gln Pro Val Arg Phe Val Gly Ile Ala Asn
305                 310                 315                 320
Leu Arg Val Lys Glu Cys Asp Arg Ile Ser Ala Leu Ser Asn Gly Leu
                325                 330                 335
Cys Ala Ile Ala Pro Gly Leu Ala Val Glu Glu Gly Asp Asp Leu Ile
            340                 345                 350
Val Thr Ala Asn Pro Thr Leu Ala Gly Thr Thr Val Asp Ala Leu Ile
            355                 360                 365
Asp Thr His Ser Asp His Arg Ile Ala Met Cys Phe Ala Leu Ala Gly
        370                 375                 380
Leu Lys Ile Ala Gly Ile Arg Ile Leu Asp Pro Asp Cys Val Ala Lys
385                 390                 395                 400
Thr Tyr Pro Gly Tyr Trp Asp Ala Leu Ala Ser Leu Gly Val Ser Val
                405                 410                 415
Gln Arg

<210> SEQ ID NO 47
<211> LENGTH: 1466
<212> TYPE: DNA
<213> ORGANISM: Pseudomonas syringae
<220> FEATURE:
<221> NAME/KEY: CDS
<222> LOCATION: (101)...(1357)
<220> FEATURE:
<221> NAME/KEY: misc_feature
<222> LOCATION: (0)...(0)
<223> OTHER INFORMATION: pv phaseolicola strain 1448a
```

<400> SEQUENCE: 47

```
gtaaacggct gtctggcccg ttggggcagc aaaaccgcac tgcgggcttg atcccgctcg      60
tgctaggatc gcgattttc cgctgacgct cagggacatc atg cga cct caa gcc       115
                                            Met Arg Pro Gln Ala
                                            1               5 acc ctc act gtt ttg cct gtc gag cgc ccg ctg gtc ggg cgc gtc agc       163
Thr Leu Thr Val Leu Pro Val Glu Arg Pro Leu Val Gly Arg Val Ser
             10                  15                  20 ccg ccg ggc tcc aag tcg atc acc aac cgc gca ttg ttg ctg gcc ggg       211
Pro Pro Gly Ser Lys Ser Ile Thr Asn Arg Ala Leu Leu Leu Ala Gly
         25                  30                  35 ctg gcc aaa ggc acc agc cgc ctg acc ggc gcg ctg aag agt gac gac       259
Leu Ala Lys Gly Thr Ser Arg Leu Thr Gly Ala Leu Lys Ser Asp Asp
     40                  45                  50 acc cgc gtg atg tcc gaa gca ctg cgt ctg atg ggc gtg cag gtc gac       307
Thr Arg Val Met Ser Glu Ala Leu Arg Leu Met Gly Val Gln Val Asp
 55                  60                  65 gag ccg gat gac agc acc ttc gtg gtc acc agc agc ggc cac tgg cag       355
Glu Pro Asp Asp Ser Thr Phe Val Val Thr Ser Ser Gly His Trp Gln
 70                  75                  80                  85 gca ccg cag cag gca ctg ttt ctc ggt aac gcc gga acc gca acg cgc       403
Ala Pro Gln Gln Ala Leu Phe Leu Gly Asn Ala Gly Thr Ala Thr Arg
                 90                  95                 100 ttt ctg acc gct gca ctg gcc aac ttc gaa ggc gac ttt gtg gtc gac       451
Phe Leu Thr Ala Ala Leu Ala Asn Phe Glu Gly Asp Phe Val Val Asp
             105                 110                 115 ggc gac gag tac atg cgc aag cgc ccg atc ggc ccg ctg gtc gat gcc       499
Gly Asp Glu Tyr Met Arg Lys Arg Pro Ile Gly Pro Leu Val Asp Ala
         120                 125                 130 ttg cag cgc atg ggt gtg gag gtc agt gcg ccc agt ggc tgc ccg ccg       547
Leu Gln Arg Met Gly Val Glu Val Ser Ala Pro Ser Gly Cys Pro Pro
     135                 140                 145 gtg gcg atc aag ggc aaa ggc ggt ctg gaa gcc gga cgt att gaa atc       595
Val Ala Ile Lys Gly Lys Gly Gly Leu Glu Ala Gly Arg Ile Glu Ile
150                 155                 160                 165 gat ggc aac ctg tcc agc cag tac gtg tca gcg ttg ctg atg gcc gga       643
Asp Gly Asn Leu Ser Ser Gln Tyr Val Ser Ala Leu Leu Met Ala Gly
                 170                 175                 180 gcc tgc ggc aag ggc ccg gtc gaa gtc gcc ttg acc ggc agc gag att       691
Ala Cys Gly Lys Gly Pro Val Glu Val Ala Leu Thr Gly Ser Glu Ile
             185                 190                 195 ggc gca cgt ggt tac gtc gac ctt acc ctg gcg gcc atg cag gcc ttc       739
Gly Ala Arg Gly Tyr Val Asp Leu Thr Leu Ala Ala Met Gln Ala Phe
         200                 205                 210 ggc gcc gag gtt cag gcc atc ggc gaa acc gcc tgg aaa gtc tcg gcc       787
Gly Ala Glu Val Gln Ala Ile Gly Glu Thr Ala Trp Lys Val Ser Ala
     215                 220                 225 act ggt tat cgc gct acg gac ttc cat atc gaa ccg gat gca tcg gcg       835
Thr Gly Tyr Arg Ala Thr Asp Phe His Ile Glu Pro Asp Ala Ser Ala
230                 235                 240                 245 gcc acc tac ctg tgg gcc gcc caa gca ctg acc gag ggc gat atc gac       883
Ala Thr Tyr Leu Trp Ala Ala Gln Ala Leu Thr Glu Gly Asp Ile Asp
                 250                 255                 260 ctc ggc gtg gcc agc gac gca ttc act cag cct gat gcc ctg gcc agt       931
Leu Gly Val Ala Ser Asp Ala Phe Thr Gln Pro Asp Ala Leu Ala Ser
             265                 270                 275 cag atc atc gca agc ttc ccg aac atg cct gcc gtg atc gac ggt tcg       979
Gln Ile Ile Ala Ser Phe Pro Asn Met Pro Ala Val Ile Asp Gly Ser
```

```
                280                 285                 290
caa atg cag gac gcg att ccg acg ctg gcg gta ctc gcc gcc ttc aac     1027
Gln Met Gln Asp Ala Ile Pro Thr Leu Ala Val Leu Ala Ala Phe Asn
    295                 300                 305 cgt cag cca gtg cgc ttt gtc ggc atc gcc aac ctg cgg gtc aag gaa     1075
Arg Gln Pro Val Arg Phe Val Gly Ile Ala Asn Leu Arg Val Lys Glu
310                 315                 320                 325 tgt gac cgt att tca gca ctg tcc cac ggc ctg tgt gcc atc gcg ccg     1123
Cys Asp Arg Ile Ser Ala Leu Ser His Gly Leu Cys Ala Ile Ala Pro
                330                 335                 340 ggc ctt gct gta gag gag ggc gac gac ctg ctg gtg cac gcc aac ccg     1171
Gly Leu Ala Val Glu Glu Gly Asp Asp Leu Leu Val His Ala Asn Pro
            345                 350                 355 gcg ctg gca ggc acc acg gta gac gca ttg att gac acc cac tcc gac     1219
Ala Leu Ala Gly Thr Thr Val Asp Ala Leu Ile Asp Thr His Ser Asp
        360                 365                 370 cat cgc atc gcc atg tgt ttt gcg ctg gca ggc ttg aag att gcc ggt     1267
His Arg Ile Ala Met Cys Phe Ala Leu Ala Gly Leu Lys Ile Ala Gly
    375                 380                 385 att cgc att ctc gac cca gat tgc gtc ggc aag acc tac ccg ggt tac     1315
Ile Arg Ile Leu Asp Pro Asp Cys Val Gly Lys Thr Tyr Pro Gly Tyr
390                 395                 400                 405 tgg gat gca ctg gct tcg ctg ggg gtg cgt gtt cag cgc tga             1357
Trp Asp Ala Leu Ala Ser Leu Gly Val Arg Val Gln Arg *
                410                 415 gagcagctat ggagccgttt ttcagatccc gaagaacggc tgcatcatcc gcgccagcag   1417
cccgtgaaag cgcagccttg attctgtcgc cagtacgcag atgcattcc               1466

<210> SEQ ID NO 48
<211> LENGTH: 418
<212> TYPE: PRT
<213> ORGANISM: Pseudomonas syringae
<220> FEATURE:
<221> NAME/KEY: VARIANT
<222> LOCATION: (0)...(0)
<223> OTHER INFORMATION: pv phaseolicola strain 1448a

<400> SEQUENCE: 48

Met Arg Pro Gln Ala Thr Leu Thr Val Leu Pro Val Glu Arg Pro Leu
1               5                   10                  15

Val Gly Arg Val Ser Pro Pro Gly Ser Lys Ser Ile Thr Asn Arg Ala
            20                  25                  30

Leu Leu Leu Ala Gly Leu Ala Lys Gly Thr Ser Arg Leu Thr Gly Ala
        35                  40                  45

Leu Lys Ser Asp Asp Thr Arg Val Met Ser Glu Ala Leu Arg Leu Met
    50                  55                  60

Gly Val Gln Val Asp Glu Pro Asp Ser Thr Phe Val Val Thr Ser
65                  70                  75                  80

Ser Gly His Trp Gln Ala Pro Gln Gln Ala Leu Phe Leu Gly Asn Ala
                85                  90                  95

Gly Thr Ala Thr Arg Phe Leu Thr Ala Ala Leu Ala Asn Phe Glu Gly
            100                 105                 110

Asp Phe Val Val Asp Gly Asp Glu Tyr Met Arg Lys Arg Pro Ile Gly
        115                 120                 125

Pro Leu Val Asp Ala Leu Gln Arg Met Gly Val Glu Val Ser Ala Pro
    130                 135                 140

Ser Gly Cys Pro Pro Val Ala Ile Lys Gly Lys Gly Gly Leu Glu Ala
145                 150                 155                 160
```

Gly Arg Ile Glu Ile Asp Gly Asn Leu Ser Ser Gln Tyr Val Ser Ala
            165                 170                 175

Leu Leu Met Ala Gly Ala Cys Gly Lys Gly Pro Val Glu Val Ala Leu
            180                 185                 190

Thr Gly Ser Glu Ile Gly Ala Arg Gly Tyr Val Asp Leu Thr Leu Ala
            195                 200                 205

Ala Met Gln Ala Phe Gly Ala Glu Val Gln Ala Ile Gly Glu Thr Ala
        210                 215                 220

Trp Lys Val Ser Ala Thr Gly Tyr Arg Ala Thr Asp Phe His Ile Glu
225                 230                 235                 240

Pro Asp Ala Ser Ala Ala Thr Tyr Leu Trp Ala Ala Gln Ala Leu Thr
                245                 250                 255

Glu Gly Asp Ile Asp Leu Gly Val Ala Ser Asp Ala Phe Thr Gln Pro
            260                 265                 270

Asp Ala Leu Ala Ser Gln Ile Ile Ala Ser Phe Pro Asn Met Pro Ala
        275                 280                 285

Val Ile Asp Gly Ser Gln Met Gln Asp Ala Ile Pro Thr Leu Ala Val
    290                 295                 300

Leu Ala Ala Phe Asn Arg Gln Pro Val Arg Phe Val Gly Ile Ala Asn
305                 310                 315                 320

Leu Arg Val Lys Glu Cys Asp Arg Ile Ser Ala Leu Ser His Gly Leu
                325                 330                 335

Cys Ala Ile Ala Pro Gly Leu Ala Val Glu Glu Gly Asp Asp Leu Leu
            340                 345                 350

Val His Ala Asn Pro Ala Leu Ala Gly Thr Thr Val Asp Ala Leu Ile
        355                 360                 365

Asp Thr His Ser Asp His Arg Ile Ala Met Cys Phe Ala Leu Ala Gly
    370                 375                 380

Leu Lys Ile Ala Gly Ile Arg Ile Leu Asp Pro Asp Cys Val Gly Lys
385                 390                 395                 400

Thr Tyr Pro Gly Tyr Trp Asp Ala Leu Ala Ser Leu Gly Val Arg Val
                405                 410                 415

Gln Arg

<210> SEQ ID NO 49
<211> LENGTH: 427
<212> TYPE: PRT
<213> ORGANISM: Escherichia coli

<400> SEQUENCE: 49

Met Glu Ser Leu Thr Leu Gln Pro Ile Ala Arg Val Asp Gly Thr Ile
1               5                   10                  15

Asn Leu Pro Gly Ser Lys Thr Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Ala Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
115                 120                 125

Leu Val Asp Ala Leu Arg Leu Gly Ala Lys Ile Thr Tyr Leu Glu
130                 135                 140

Gln Glu Asn Tyr Pro Pro Leu Arg Leu Gln Gly Phe Thr Gly Gly
145                 150                 155                 160

Asn Val Asp Val Asp Gly Ser Val Ser Gln Phe Leu Thr Ala Leu
                165                 170                 175

Leu Met Thr Ala Pro Leu Ala Pro Glu Asp Thr Val Ile Arg Ile Lys
                180                 185                 190

Gly Asp Leu Val Ser Lys Pro Tyr Ile Asp Ile Thr Leu Asn Leu Met
                195                 200                 205

Lys Thr Phe Gly Val Glu Ile Glu Asn Gln His Tyr Gln Gln Phe Val
                210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ile Lys
                245                 250                 255

Gly Gly Thr Val Lys Val Thr Gly Ile Gly Arg Asn Ser Met Gln Gly
                260                 265                 270

Asp Ile Arg Phe Ala Asp Val Leu Glu Lys Met Gly Ala Thr Ile Cys
                275                 280                 285

Trp Gly Asp Asp Tyr Ile Ser Cys Thr Arg Gly Glu Leu Asn Ala Ile
                290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Arg Leu Arg Asn Ile Tyr Asn
                325                 330                 335

Trp Arg Val Lys Glu Thr Asp Arg Leu Phe Ala Met Ala Thr Glu Leu
                340                 345                 350

Arg Lys Val Gly Ala Glu Val Glu Glu Gly His Asp Tyr Ile Arg Ile
                355                 360                 365

Thr Pro Pro Glu Lys Leu Asn Phe Ala Glu Ile Ala Thr Tyr Asn Asp
                370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
                420                 425

<210> SEQ ID NO 50
<211> LENGTH: 444
<212> TYPE: PRT
<213> ORGANISM: Zea mays

<400> SEQUENCE: 50

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
                20                  25                  30

Leu Ala Ala Leu Ser Glu Gly Thr Thr Val Val Asp Asn Leu Leu Asn
                35                  40                  45

Ser Glu Asp Val His Tyr Met Leu Gly Ala Leu Arg Thr Leu Gly Leu

```
                50                   55                  60
Ser Val Glu Ala Asp Lys Ala Lys Arg Ala Val Val Gly Cys
 65                  70                  75                  80
Gly Gly Lys Phe Pro Val Glu Asp Ala Lys Glu Glu Val Gln Leu Phe
                     85                  90                  95
Leu Gly Asn Ala Gly Thr Ala Met Arg Pro Leu Thr Ala Ala Val Thr
                100                 105                 110
Ala Ala Gly Gly Asn Ala Thr Tyr Val Leu Asp Gly Val Pro Arg Met
                115                 120                 125
Arg Glu Arg Pro Ile Gly Asp Leu Val Val Gly Leu Lys Gln Leu Gly
130                 135                 140
Ala Asp Val Asp Cys Phe Leu Gly Thr Asp Cys Pro Pro Val Arg Val
145                 150                 155                 160
Asn Gly Ile Gly Gly Leu Pro Gly Gly Lys Val Lys Leu Ser Gly Ser
                165                 170                 175
Ile Ser Ser Gln Tyr Leu Ser Ala Leu Leu Met Ala Ala Pro Leu Ala
                180                 185                 190
Leu Gly Asp Val Glu Ile Glu Ile Asp Lys Leu Ile Ser Ile Pro
                195                 200                 205
Tyr Val Glu Met Thr Leu Arg Leu Met Glu Arg Phe Gly Val Lys Ala
210                 215                 220
Glu His Ser Asp Ser Trp Asp Arg Phe Tyr Ile Lys Gly Gly Gln Lys
225                 230                 235                 240
Tyr Lys Ser Pro Lys Asn Ala Tyr Val Glu Gly Asp Ala Ser Ser Ala
                245                 250                 255
Ser Tyr Phe Leu Ala Gly Ala Ala Ile Thr Gly Gly Thr Val Thr Val
                260                 265                 270
Glu Gly Cys Gly Thr Thr Ser Leu Gln Gly Asp Val Lys Phe Ala Glu
                275                 280                 285
Val Leu Glu Met Met Gly Ala Lys Val Thr Trp Thr Glu Thr Ser Val
                290                 295                 300
Thr Val Thr Gly Pro Pro Arg Glu Pro Phe Gly Arg Lys His Leu Lys
305                 310                 315                 320
Ala Ile Asp Val Asn Met Asn Lys Met Pro Asp Val Ala Met Thr Leu
                325                 330                 335
Ala Val Val Ala Leu Phe Ala Asp Gly Pro Thr Ala Ile Arg Asp Val
                340                 345                 350
Ala Ser Trp Arg Val Lys Glu Thr Glu Arg Met Val Ala Ile Arg Thr
                355                 360                 365
Glu Leu Thr Lys Leu Gly Ala Ser Val Glu Glu Gly Pro Asp Tyr Cys
                370                 375                 380
Ile Ile Thr Pro Pro Glu Lys Leu Asn Val Thr Ala Ile Asp Thr Tyr
385                 390                 395                 400
Asp Asp His Arg Met Ala Met Ala Phe Ser Leu Ala Ala Cys Ala Glu
                405                 410                 415
Val Pro Val Thr Ile Arg Asp Pro Gly Cys Thr Arg Lys Thr Phe Pro
                420                 425                 430
Asp Tyr Phe Asp Val Leu Ser Thr Phe Val Lys Asn
                435                 440

<210> SEQ ID NO 51
<211> LENGTH: 455
<212> TYPE: PRT
<213> ORGANISM: Agrobacterium sp.
```

```
<220> FEATURE:
<221> NAME/KEY: VARIANT
<222> LOCATION: (0)...(0)
<223> OTHER INFORMATION: strain CP4

<400> SEQUENCE: 51
```

Met Ser His Gly Ala Ser Ser Arg Pro Ala Thr Ala Arg Lys Ser Ser
1               5                   10                  15

Gly Leu Ser Gly Thr Val Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Lys Ala Met Gln
    50                  55                  60

Ala Met Gly Ala Arg Ile Arg Lys Glu Gly Asp Thr Trp Ile Ile Asp
65                  70                  75                  80

Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
    130                 135                 140

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285

Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
            340                 345                 350

Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400

His Leu Asp His Arg Ile Ala Met Ser Phe Leu Val Met Gly Leu Val
                405                 410                 415

Ser Glu Asn Pro Val Thr Val Asp Ala Thr Met Ile Ala Thr Ser
            420                 425                 430

Phe Pro Glu Phe Met Asp Leu Met Ala Gly Leu Gly Ala Lys Ile Glu
        435                 440                 445

Leu Ser Asp Thr Lys Ala Ala
    450                 455

<210> SEQ ID NO 52
<211> LENGTH: 428
<212> TYPE: PRT
<213> ORGANISM: Bacillus subtilis
<220> FEATURE:
<221> NAME/KEY: VARIANT
<222> LOCATION: (0)...(0)
<223> OTHER INFORMATION: EPSPS-protein

<400> SEQUENCE: 52

Met Lys Arg Asp Lys Val Gln Thr Leu His Gly Glu Ile His Ile Pro
1               5                   10                  15

Gly Asp Lys Ser Ile Ser His Arg Ser Val Met Phe Gly Ala Leu Ala
            20                  25                  30

Ala Gly Thr Thr Thr Val Lys Asn Phe Leu Pro Gly Ala Asp Cys Leu
        35                  40                  45

Ser Thr Ile Asp Cys Phe Arg Lys Met Gly Val His Ile Glu Gln Ser
    50                  55                  60

Ser Ser Asp Val Val Ile His Gly Lys Gly Ile Asp Ala Leu Lys Glu
65                  70                  75                  80

Pro Glu Ser Leu Leu Asp Val Gly Asn Ser Gly Thr Thr Ile Arg Leu
                85                  90                  95

Met Leu Gly Ile Leu Ala Gly Arg Pro Phe Tyr Ser Ala Val Ala Gly
            100                 105                 110

Asp Glu Ser Ile Ala Lys Arg Pro Met Lys Arg Val Thr Glu Pro Leu
        115                 120                 125

Lys Lys Met Gly Ala Lys Ile Asp Gly Arg Ala Gly Gly Glu Phe Thr
130                 135                 140

Pro Leu Ser Val Ser Gly Ala Ser Leu Lys Gly Ile Asp Tyr Val Ser
145                 150                 155                 160

Pro Val Ala Ser Ala Gln Ile Lys Ser Ala Val Leu Leu Ala Gly Leu
                165                 170                 175

Gln Ala Glu Gly Thr Thr Thr Val Thr Glu Pro His Lys Ser Arg Asp
            180                 185                 190

His Thr Glu Arg Met Leu Ser Ala Phe Gly Val Lys Leu Ser Glu Asp
        195                 200                 205

Gln Thr Ser Val Ser Ile Ala Gly Gly Gln Lys Leu Thr Ala Ala Asp
    210                 215                 220

Ile Phe Val Pro Gly Asp Ile Ser Ser Ala Ala Phe Phe Leu Ala Ala
225                 230                 235                 240

Gly Ala Met Val Pro Asn Ser Arg Ile Val Leu Lys Asn Val Gly Leu
                245                 250                 255

Asn Pro Thr Arg Thr Gly Ile Ile Asp Val Leu Gln Asn Met Gly Ala
            260                 265                 270

Lys Leu Glu Ile Lys Pro Ser Ala Asp Ser Gly Ala Glu Pro Tyr Gly

```
                    275                 280                 285
Asp Leu Ile Ile Glu Thr Ser Ser Leu Lys Ala Val Glu Ile Gly Gly
    290                 295                 300

Asp Ile Ile Pro Arg Leu Ile Asp Glu Ile Pro Ile Ile Ala Leu Leu
305                 310                 315                 320

Ala Thr Gln Ala Glu Gly Thr Thr Val Ile Lys Asp Ala Ala Glu Leu
                325                 330                 335

Lys Val Lys Glu Thr Asn Arg Ile Asp Thr Val Val Ser Glu Leu Arg
            340                 345                 350

Lys Leu Gly Ala Glu Ile Glu Pro Thr Ala Asp Gly Met Lys Val Tyr
        355                 360                 365

Gly Lys Gln Thr Leu Lys Gly Gly Ala Ala Val Ser Ser His Gly Asp
    370                 375                 380

His Arg Ile Gly Met Met Leu Gly Ile Ala Ser Cys Ile Thr Glu Glu
385                 390                 395                 400

Pro Ile Glu Ile Glu His Thr Asp Ala Ile His Val Ser Tyr Pro Thr
                405                 410                 415

Phe Phe Glu His Leu Asn Lys Leu Ser Lys Lys Ser
            420                 425

<210> SEQ ID NO 53
<211> LENGTH: 1500
<212> TYPE: DNA
<213> ORGANISM: Unknown
<220> FEATURE:
<223> OTHER INFORMATION: Unknown bacterium
<220> FEATURE:
<221> NAME/KEY: CDS
<222> LOCATION: (40)...(1371)

<400> SEQUENCE: 53
ctcctacagt tagggcaagt cccccaccac tcgacaagc atg gcg tgt ttg cct          54
                                          Met Ala Cys Leu Pro
                                            1               5 gat gat tcg ggt ccg cat gtc ggc cac tcc acg cca cct cgc ctt gac        102
Asp Asp Ser Gly Pro His Val Gly His Ser Thr Pro Pro Arg Leu Asp
        10                  15                  20 cag gag cct tgt acc ttg agt tcg cag aaa acc gtg acc gtt aca ccg        150
Gln Glu Pro Cys Thr Leu Ser Ser Gln Lys Thr Val Thr Val Thr Pro
    25                  30                  35 ccc aac ttc ccc ctc act ggc aag gtc gcg ccc ccc ggc tcc aaa tcc        198
Pro Asn Phe Pro Leu Thr Gly Lys Val Ala Pro Pro Gly Ser Lys Ser
40                  45                  50 att acc aac cgt gcg ctg ttg ctg gcg gca ttg gcc aag ggc acc agc        246
Ile Thr Asn Arg Ala Leu Leu Leu Ala Ala Leu Ala Lys Gly Thr Ser
                55                  60                  65 cgt ttg agc ggt gcg ctc aaa agc gat gac acg cgc cac atg tcg gtc        294
Arg Leu Ser Gly Ala Leu Lys Ser Asp Asp Thr Arg His Met Ser Val
70                  75                  80                  85 gcc ctg cgg cag atg ggc gtc acc atc gac gag ccg gac gac acc acc        342
Ala Leu Arg Gln Met Gly Val Thr Ile Asp Glu Pro Asp Asp Thr Thr
                90                  95                 100 ttt gtg gtc acc agc caa ggc tcg ctg caa ttg ccg gcc cag ccg ttg        390
Phe Val Val Thr Ser Gln Gly Ser Leu Gln Leu Pro Ala Gln Pro Leu
            105                 110                 115 ttc ctc ggc aac gct ggc acc gcc atg cgc ttt ctc acg gct gcc gtg        438
Phe Leu Gly Asn Ala Gly Thr Ala Met Arg Phe Leu Thr Ala Ala Val
        120                 125                 130 gcc acc gtg caa ggc acc gtg gta ctg gac ggc gac gag tac atg caa        486
```

```
                Ala Thr Val Gln Gly Thr Val Val Leu Asp Gly Asp Glu Tyr Met Gln
                    135                 140                 145 aaa cgc ccg att ggc ccg ctg ctg gct acc ctg ggc cag aac ggc atc          534
Lys Arg Pro Ile Gly Pro Leu Leu Ala Thr Leu Gly Gln Asn Gly Ile
150                 155                 160                 165 cag gtc gac agc ccc acc ggt tgc cca ccg gtc acc gtg cac ggc atg          582
Gln Val Asp Ser Pro Thr Gly Cys Pro Pro Val Thr Val His Gly Met
                170                 175                 180 ggc aag gtc cag gcc aag cgt ttc gag att gat ggt ggt ttg tcc agc          630
Gly Lys Val Gln Ala Lys Arg Phe Glu Ile Asp Gly Gly Leu Ser Ser
            185                 190                 195 cag tac gta tcg gcc ctg ctg atg ctc gcg gcg tgc ggc gaa gcg ccg          678
Gln Tyr Val Ser Ala Leu Leu Met Leu Ala Ala Cys Gly Glu Ala Pro
        200                 205                 210 att gaa gtg gcg ctg acc ggc aag gat atc ggt gcc cgt ggc tac gtg          726
Ile Glu Val Ala Leu Thr Gly Lys Asp Ile Gly Ala Arg Gly Tyr Val
    215                 220                 225 gac ctg acc ctc gac tgc atg cgt gcc ttc ggg gcc cag gtg gac gcc          774
Asp Leu Thr Leu Asp Cys Met Arg Ala Phe Gly Ala Gln Val Asp Ala
230                 235                 240                 245 gtg gac gac acc acc tgg cgc gtc gcc ccc acc ggc tat acc gcc cat          822
Val Asp Asp Thr Thr Trp Arg Val Ala Pro Thr Gly Tyr Thr Ala His
                250                 255                 260 gat tac ctg atc gaa ccc gat gcg tcc gcc gcc acg tat ttg tgg gcc          870
Asp Tyr Leu Ile Glu Pro Asp Ala Ser Ala Ala Thr Tyr Leu Trp Ala
            265                 270                 275 gca gaa gtg ctg acc ggt ggg cgt atc gac atc ggc gta gcc gcg cag          918
Ala Glu Val Leu Thr Gly Gly Arg Ile Asp Ile Gly Val Ala Ala Gln
        280                 285                 290 gac ttc acc cag ccc gac gcc aag gcc cag gcc gtg att gcg cag ttc          966
Asp Phe Thr Gln Pro Asp Ala Lys Ala Gln Ala Val Ile Ala Gln Phe
    295                 300                 305 ccg aac atg caa gcc acg gtg gta ggc tcg caa atg cag gat gcg atc         1014
Pro Asn Met Gln Ala Thr Val Val Gly Ser Gln Met Gln Asp Ala Ile
310                 315                 320                 325 ccg acc ctg gcg gtg ctc gcc gcg ttc aac aac acc ccg gtg cgt ttc         1062
Pro Thr Leu Ala Val Leu Ala Ala Phe Asn Asn Thr Pro Val Arg Phe
                330                 335                 340 act gaa ctg gcg aac ctg cgc gtc aag gaa tgt gac cgc gtg cag gcg         1110
Thr Glu Leu Ala Asn Leu Arg Val Lys Glu Cys Asp Arg Val Gln Ala
            345                 350                 355 ctg cac gat ggc ctc aac gaa att cgc ccg ggc ctg gcg acc atc gag         1158
Leu His Asp Gly Leu Asn Glu Ile Arg Pro Gly Leu Ala Thr Ile Glu
        360                 365                 370 ggc gat gac ctg ctg gtc gcc agc gac ccg gcc ctg gca ggc acc gcc         1206
Gly Asp Asp Leu Leu Val Ala Ser Asp Pro Ala Leu Ala Gly Thr Ala
    375                 380                 385 tgc acc gca ctg atc gac acc cac gcc gac cat cgc atc gcc atg tgc         1254
Cys Thr Ala Leu Ile Asp Thr His Ala Asp His Arg Ile Ala Met Cys
390                 395                 400                 405 ttt gcc ctg gcc ggg ctt aaa gtc tcg ggc att cgc att caa gac ccg         1302
Phe Ala Leu Ala Gly Leu Lys Val Ser Gly Ile Arg Ile Gln Asp Pro
                410                 415                 420 gac tgc gtg gcc aag acc tac cct gac tac tgg aaa gcc tgg ccc agc         1350
Asp Cys Val Ala Lys Thr Tyr Pro Asp Tyr Trp Lys Ala Trp Pro Ser
            425                 430                 435 ctg ggc gtt cac cta aac gac tgacacacaa aacctgtagc agagcttgct            1401
Leu Gly Val His Leu Asn Asp
        440
```

```
cgcgaaaaac gcacacgtgc cgcgtttgtt caggaaacac gcgttatcgt tgacgtttat    1461
cgagctaagc tcgctcctac attttgcagc gagatcttg                            1500
```

<210> SEQ ID NO 54
<211> LENGTH: 444
<212> TYPE: PRT
<213> ORGANISM: Unknown
<220> FEATURE:
<223> OTHER INFORMATION: Unknown bacterium

<400> SEQUENCE: 54

Met Ala Cys Leu Pro Asp Asp Ser Gly Pro His Val Gly His Ser Thr
1               5                   10                  15

Pro Pro Arg Leu Asp Gln Glu Pro Cys Thr Leu Ser Ser Gln Lys Thr
            20                  25                  30

Val Thr Val Thr Pro Pro Asn Phe Pro Leu Thr Gly Lys Val Ala Pro
        35                  40                  45

Pro Gly Ser Lys Ser Ile Thr Asn Arg Ala Leu Leu Leu Ala Ala Leu
    50                  55                  60

Ala Lys Gly Thr Ser Arg Leu Ser Gly Ala Leu Lys Ser Asp Asp Thr
65                  70                  75                  80

Arg His Met Ser Val Ala Leu Arg Gln Met Gly Val Thr Ile Asp Glu
                85                  90                  95

Pro Asp Asp Thr Thr Phe Val Val Thr Ser Gln Gly Ser Leu Gln Leu
            100                 105                 110

Pro Ala Gln Pro Leu Phe Leu Gly Asn Ala Gly Thr Ala Met Arg Phe
        115                 120                 125

Leu Thr Ala Ala Val Ala Thr Val Gln Gly Thr Val Val Leu Asp Gly
130                 135                 140

Asp Glu Tyr Met Gln Lys Arg Pro Ile Gly Pro Leu Leu Ala Thr Leu
145                 150                 155                 160

Gly Gln Asn Gly Ile Gln Val Asp Ser Pro Thr Gly Cys Pro Pro Val
                165                 170                 175

Thr Val His Gly Met Gly Lys Val Gln Ala Lys Arg Phe Glu Ile Asp
            180                 185                 190

Gly Gly Leu Ser Ser Gln Tyr Val Ser Ala Leu Leu Met Leu Ala Ala
        195                 200                 205

Cys Gly Glu Ala Pro Ile Glu Val Ala Leu Thr Gly Lys Asp Ile Gly
210                 215                 220

Ala Arg Gly Tyr Val Asp Leu Thr Leu Asp Cys Met Arg Ala Phe Gly
225                 230                 235                 240

Ala Gln Val Asp Ala Val Asp Asp Thr Thr Trp Arg Val Ala Pro Thr
                245                 250                 255

Gly Tyr Thr Ala His Asp Tyr Leu Ile Glu Pro Asp Ala Ser Ala Ala
            260                 265                 270

Thr Tyr Leu Trp Ala Ala Glu Val Leu Thr Gly Gly Arg Ile Asp Ile
        275                 280                 285

Gly Val Ala Ala Gln Asp Phe Thr Gln Pro Asp Ala Lys Ala Gln Ala
290                 295                 300

Val Ile Ala Gln Phe Gln Asn Met Gln Ala Thr Val Val Gly Ser Gln
305                 310                 315                 320

Met Gln Asp Ala Ile Pro Thr Leu Ala Val Leu Ala Ala Phe Asn Asn
                325                 330                 335

Thr Pro Val Arg Phe Thr Glu Leu Ala Asn Leu Arg Val Lys Glu Cys
            340                 345                 350

```
Asp Arg Val Gln Ala Leu His Asp Gly Leu Asn Glu Ile Arg Pro Gly
        355                 360                 365

Leu Ala Thr Ile Glu Gly Asp Leu Leu Val Ala Ser Asp Pro Ala
        370                 375                 380

Leu Ala Gly Thr Ala Cys Thr Ala Leu Ile Asp Thr His Ala Asp His
385                 390                 395                 400

Arg Ile Ala Met Cys Phe Ala Leu Ala Gly Leu Lys Val Ser Gly Ile
                405                 410                 415

Arg Ile Gln Asp Pro Asp Cys Val Ala Lys Thr Tyr Pro Asp Tyr Trp
            420                 425                 430

Lys Ala Trp Pro Ser Leu Gly Val His Leu Asn Asp
        435                 440
```

<210> SEQ ID NO 55
<211> LENGTH: 1257
<212> TYPE: DNA
<213> ORGANISM: Pseudomonas syringae
<220> FEATURE:
<221> NAME/KEY: misc_feature
<222> LOCATION: (0)...(0)
<223> OTHER INFORMATION: pv syringae strain B728a
<220> FEATURE:
<221> NAME/KEY: CDS
<222> LOCATION: (1)...(1257)

<400> SEQUENCE: 55

| | |
|---|---:|
| atg cga cct caa gcc acc ctc act gtt ttg cct gtc gag cgc ccg ttg<br>Met Arg Pro Gln Ala Thr Leu Thr Val Leu Pro Val Glu Arg Pro Leu<br>1               5                   10                  15 | 48 |
| gtc ggg cgt gtc agc ccg ccg ggc tcc aag tcg atc acc aac cgt gca<br>Val Gly Arg Val Ser Pro Pro Gly Ser Lys Ser Ile Thr Asn Arg Ala<br>            20                  25                  30 | 96 |
| ttg ttg ctg gcc ggg ctg gcc aaa ggc acc agc cgc ctg acc ggc gcg<br>Leu Leu Leu Ala Gly Leu Ala Lys Gly Thr Ser Arg Leu Thr Gly Ala<br>        35                  40                  45 | 144 |
| ctg aag agt gat gac acg cgc gtg atg tcc gaa gcc ttg cgt ctg atg<br>Leu Lys Ser Asp Asp Thr Arg Val Met Ser Glu Ala Leu Arg Leu Met<br>    50                  55                  60 | 192 |
| ggc gtg cag gtc gac gag ccg gat gac agc acc ttc gtg gtc acc agc<br>Gly Val Gln Val Asp Glu Pro Asp Asp Ser Thr Phe Val Val Thr Ser<br>65                  70                  75                  80 | 240 |
| agc ggg cac tgg cag gcg ccg caa cag gcg ctg ttc ctc ggc aat gcc<br>Ser Gly His Trp Gln Ala Pro Gln Gln Ala Leu Phe Leu Gly Asn Ala<br>                85                  90                  95 | 288 |
| ggg act gcg aca cgc ttt ctg acc gcg gca ctg gcc aac ttc gaa ggc<br>Gly Thr Ala Thr Arg Phe Leu Thr Ala Ala Leu Ala Asn Phe Glu Gly<br>            100                 105                 110 | 336 |
| gac ttc gtg gtg gat ggc gac gaa tac atg cgc aag cgc ccg atc ggc<br>Asp Phe Val Val Asp Gly Asp Glu Tyr Met Arg Lys Arg Pro Ile Gly<br>        115                 120                 125 | 384 |
| ccg ttg gtc gat gcc ttg cag cgc atg ggc gtg gag gtc agc gca ccc<br>Pro Leu Val Asp Ala Leu Gln Arg Met Gly Val Glu Val Ser Ala Pro<br>    130                 135                 140 | 432 |
| agt ggt tgc ccg ccg gtg gcc atc aag ggc aag ggc ggt ctt gag gcc<br>Ser Gly Cys Pro Pro Val Ala Ile Lys Gly Lys Gly Gly Leu Glu Ala<br>145                 150                 155                 160 | 480 |
| ggt cgt atc gaa atc gat ggc aat ctg tcc agc cag tat gtg tcg gca<br>Gly Arg Ile Glu Ile Asp Gly Asn Leu Ser Ser Gln Tyr Val Ser Ala<br>                165                 170                 175 | 528 |
| ctg ctg atg gcc ggt gcc tgt ggc aag ggg cct gtg gaa gtt gcc ctg | 576 |

```
Leu Leu Met Ala Gly Ala Cys Gly Lys Gly Pro Val Glu Val Ala Leu
            180                 185                 190 aca ggc agc gag atc ggc gcg cgt ggt tac ctc gac ctc acg ctg gcg       624
Thr Gly Ser Glu Ile Gly Ala Arg Gly Tyr Leu Asp Leu Thr Leu Ala
        195                 200                 205 gcc atg cgg gcg ttc ggt gcc gag gtt cag gcc atc ggc gac gcc gcc       672
Ala Met Arg Ala Phe Gly Ala Glu Val Gln Ala Ile Gly Asp Ala Ala
    210                 215                 220 tgg aaa gtc tcg gct acc ggt tat cgc gct acg gat ttc cac atc gaa       720
Trp Lys Val Ser Ala Thr Gly Tyr Arg Ala Thr Asp Phe His Ile Glu
225                 230                 235                 240 ccg gat gcc tcg gcg gcc acc tac ctt tgg gct gcg cag gcc ctg acc       768
Pro Asp Ala Ser Ala Ala Thr Tyr Leu Trp Ala Ala Gln Ala Leu Thr
                245                 250                 255 gag ggc gct atc gac ctg ggc gtg gcc agc aac gcg ttc act cag cct       816
Glu Gly Ala Ile Asp Leu Gly Val Ala Ser Asn Ala Phe Thr Gln Pro
            260                 265                 270 gat gca ctg gcc agt cag atc atc gcc agc ttc ccg aac atg ccg gcc       864
Asp Ala Leu Ala Ser Gln Ile Ile Ala Ser Phe Pro Asn Met Pro Ala
        275                 280                 285 gtg atc gac ggc tcg cag atg cag gac gcg att ccc acg ctg gcc gta       912
Val Ile Asp Gly Ser Gln Met Gln Asp Ala Ile Pro Thr Leu Ala Val
    290                 295                 300 ctg gcc gcg ttc aat cgt caa ccg gtg cgc ttt gtc ggc atc gcc aac       960
Leu Ala Ala Phe Asn Arg Gln Pro Val Arg Phe Val Gly Ile Ala Asn
305                 310                 315                 320 ctg cgg gtc aag gag tgc gac cgc atc tcg gca ctg tcc aac ggc ctg      1008
Leu Arg Val Lys Glu Cys Asp Arg Ile Ser Ala Leu Ser Asn Gly Leu
                325                 330                 335 tgc gcc atc gca ccc ggc ctg gcg gtc gaa gag ggt gac gat ctg atc      1056
Cys Ala Ile Ala Pro Gly Leu Ala Val Glu Glu Gly Asp Asp Leu Ile
            340                 345                 350 gtt acc gcc aac ccg acg ctg gca ggc act acg gtc gat gcc ttg atc      1104
Val Thr Ala Asn Pro Thr Leu Ala Gly Thr Thr Val Asp Ala Leu Ile
        355                 360                 365 gat acc cac tcc gac cat cgg atc gcc atg tgc ttt gca ctg gcg ggc      1152
Asp Thr His Ser Asp His Arg Ile Ala Met Cys Phe Ala Leu Ala Gly
    370                 375                 380 ctg aag att gcc ggc atc cgc att ctc gac cct gac tgc gtc gcc aag      1200
Leu Lys Ile Ala Gly Ile Arg Ile Leu Asp Pro Asp Cys Val Ala Lys
385                 390                 395                 400 acc tac ccg ggg tac tgg gat gcg ctg gtt tct ctg ggt gtg agt gtt      1248
Thr Tyr Pro Gly Tyr Trp Asp Ala Leu Val Ser Leu Gly Val Ser Val
                405                 410                 415 cag cgc tga                                                          1257
Gln Arg *

<210> SEQ ID NO 56
<211> LENGTH: 418
<212> TYPE: PRT
<213> ORGANISM: Pseudomonas syringae
<220> FEATURE:
<221> NAME/KEY: VARIANT
<222> LOCATION: (0)...(0)
<223> OTHER INFORMATION: pv syringae strain B728a

<400> SEQUENCE: 56

Met Arg Pro Gln Ala Thr Leu Thr Val Leu Pro Val Glu Arg Pro Leu
1               5                   10                  15

Val Gly Arg Val Ser Pro Pro Gly Ser Lys Ser Ile Thr Asn Arg Ala
            20                  25                  30
```

-continued

Leu Leu Leu Ala Gly Leu Ala Lys Gly Thr Ser Arg Leu Thr Gly Ala
              35                  40                  45

Leu Lys Ser Asp Asp Thr Arg Val Met Ser Glu Ala Leu Arg Leu Met
 50                  55                  60

Gly Val Gln Val Asp Glu Pro Asp Asp Ser Thr Phe Val Val Thr Ser
65                   70                  75                  80

Ser Gly His Trp Gln Ala Pro Gln Gln Ala Leu Phe Leu Gly Asn Ala
              85                  90                  95

Gly Thr Ala Thr Arg Phe Leu Thr Ala Ala Leu Ala Asn Phe Glu Gly
             100                 105                 110

Asp Phe Val Asp Gly Asp Glu Tyr Met Arg Lys Arg Pro Ile Gly
             115                 120                 125

Pro Leu Val Asp Ala Leu Gln Arg Met Gly Val Glu Val Ser Ala Pro
         130                 135                 140

Ser Gly Cys Pro Pro Val Ala Ile Lys Gly Lys Gly Gly Leu Glu Ala
145                 150                 155                 160

Gly Arg Ile Glu Ile Asp Gly Asn Leu Ser Ser Gln Tyr Val Ser Ala
                 165                 170                 175

Leu Leu Met Ala Gly Ala Cys Gly Lys Gly Pro Val Glu Val Ala Leu
             180                 185                 190

Thr Gly Ser Glu Ile Gly Ala Arg Gly Tyr Leu Asp Leu Thr Leu Ala
         195                 200                 205

Ala Met Arg Ala Phe Gly Ala Glu Val Gln Ala Ile Gly Asp Ala Ala
     210                 215                 220

Trp Lys Val Ser Ala Thr Gly Tyr Arg Ala Thr Asp Phe His Ile Glu
225                 230                 235                 240

Pro Asp Ala Ser Ala Ala Thr Tyr Leu Trp Ala Ala Gln Ala Leu Thr
                 245                 250                 255

Glu Gly Ala Ile Asp Leu Gly Val Ala Ser Asn Ala Phe Thr Gln Pro
             260                 265                 270

Asp Ala Leu Ala Ser Gln Ile Ile Ala Ser Phe Pro Asn Met Pro Ala
         275                 280                 285

Val Ile Asp Gly Ser Gln Met Gln Asp Ala Ile Pro Thr Leu Ala Val
     290                 295                 300

Leu Ala Ala Phe Asn Arg Gln Pro Val Arg Phe Val Gly Ile Ala Asn
305                 310                 315                 320

Leu Arg Val Lys Glu Cys Asp Arg Ile Ser Ala Leu Ser Asn Gly Leu
                 325                 330                 335

Cys Ala Ile Ala Pro Gly Leu Ala Val Glu Glu Gly Asp Asp Leu Ile
             340                 345                 350

Val Thr Ala Asn Pro Thr Leu Ala Gly Thr Thr Val Asp Ala Leu Ile
         355                 360                 365

Asp Thr His Ser Asp His Arg Ile Ala Met Cys Phe Ala Leu Ala Gly
     370                 375                 380

Leu Lys Ile Ala Gly Ile Arg Ile Leu Asp Pro Asp Cys Val Ala Lys
385                 390                 395                 400

Thr Tyr Pro Gly Tyr Trp Asp Ala Leu Val Ser Leu Gly Val Ser Val
                 405                 410                 415

Gln Arg

<210> SEQ ID NO 57
<211> LENGTH: 1332
<212> TYPE: DNA

<213> ORGANISM: Ochrobactrum/Brucella
<220> FEATURE:
<221> NAME/KEY: CDS
<222> LOCATION: (1)...(1332)

<400> SEQUENCE: 57

| atg | gcg | tgt | ttg | cct | gat | gat | tcg | ggt | ccg | cac | gtc | ggc | cac | tcc | acg | 48 |
| Met | Ala | Cys | Leu | Pro | Asp | Asp | Ser | Gly | Pro | His | Val | Gly | His | Ser | Thr | |
| 1 | | | | 5 | | | | | 10 | | | | | 15 | | |

| cca | cct | tgc | ctt | gac | cag | gag | cct | tgt | acc | ttg | agt | tcg | cag | aaa | acc | 96 |
| Pro | Pro | Cys | Leu | Asp | Gln | Glu | Pro | Cys | Thr | Leu | Ser | Ser | Gln | Lys | Thr | |
| | | | 20 | | | | | 25 | | | | | 30 | | | |

| gtg | acc | gtt | aca | ccg | ccc | aac | ttc | ccc | ctc | act | ggc | aag | gtc | gcg | ccc | 144 |
| Val | Thr | Val | Thr | Pro | Pro | Asn | Phe | Pro | Leu | Thr | Gly | Lys | Val | Ala | Pro | |
| | | 35 | | | | | 40 | | | | | 45 | | | | |

| ccc | ggc | tcc | aaa | tcc | att | acc | aac | cgt | gcg | ctg | ttg | ctc | gcg | gca | ctg | 192 |
| Pro | Gly | Ser | Lys | Ser | Ile | Thr | Asn | Arg | Ala | Leu | Leu | Leu | Ala | Ala | Leu | |
| 50 | | | | | 55 | | | | | 60 | | | | | | |

| gcc | aag | ggc | acc | agc | cgt | ttg | agc | ggt | gcg | ctc | aaa | agc | gat | gac | acg | 240 |
| Ala | Lys | Gly | Thr | Ser | Arg | Leu | Ser | Gly | Ala | Leu | Lys | Ser | Asp | Asp | Thr | |
| 65 | | | | | 70 | | | | | 75 | | | | | 80 | |

| cgc | cac | atg | tcg | gtc | gcc | ctg | cgg | cag | atg | ggc | gtc | acc | atc | gac | gag | 288 |
| Arg | His | Met | Ser | Val | Ala | Leu | Arg | Gln | Met | Gly | Val | Thr | Ile | Asp | Glu | |
| | | | | 85 | | | | | 90 | | | | | 95 | | |

| ccg | gac | gac | acc | acc | ttt | gtc | gtc | acc | agc | caa | ggc | tcg | ctg | caa | ttg | 336 |
| Pro | Asp | Asp | Thr | Thr | Phe | Val | Val | Thr | Ser | Gln | Gly | Ser | Leu | Gln | Leu | |
| | | | 100 | | | | | 105 | | | | | 110 | | | |

| ccg | gcc | cag | ccg | ttg | ttc | ctc | ggc | aac | gcc | ggc | acc | gcc | atg | cgc | ttt | 384 |
| Pro | Ala | Gln | Pro | Leu | Phe | Leu | Gly | Asn | Ala | Gly | Thr | Ala | Met | Arg | Phe | |
| | | 115 | | | | | 120 | | | | | 125 | | | | |

| ctc | acg | gct | gcc | gtc | gcc | acc | gtg | caa | ggc | acc | gtg | gta | ctg | gac | ggt | 432 |
| Leu | Thr | Ala | Ala | Val | Ala | Thr | Val | Gln | Gly | Thr | Val | Val | Leu | Asp | Gly | |
| | 130 | | | | | 135 | | | | | 140 | | | | | |

| gac | gag | tac | atg | caa | aaa | cgc | ccg | atc | ggc | ccg | ctg | ctg | gcc | acc | ctg | 480 |
| Asp | Glu | Tyr | Met | Gln | Lys | Arg | Pro | Ile | Gly | Pro | Leu | Leu | Ala | Thr | Leu | |
| 145 | | | | | 150 | | | | | 155 | | | | | 160 | |

| ggc | cag | aac | ggc | atc | cag | gtc | gac | agc | ccc | acc | ggt | tgc | cca | ccg | gta | 528 |
| Gly | Gln | Asn | Gly | Ile | Gln | Val | Asp | Ser | Pro | Thr | Gly | Cys | Pro | Pro | Val | |
| | | | | 165 | | | | | 170 | | | | | 175 | | |

| acg | gtg | cat | ggc | gcg | ggc | aag | gtc | cag | gcc | agg | cgt | ttt | gag | att | gac | 576 |
| Thr | Val | His | Gly | Ala | Gly | Lys | Val | Gln | Ala | Arg | Arg | Phe | Glu | Ile | Asp | |
| | | | 180 | | | | | 185 | | | | | 190 | | | |

| gga | ggc | ttg | tcc | agc | cag | tac | gta | tcg | gcc | ctg | ctg | atg | ctg | gcg | gcg | 624 |
| Gly | Gly | Leu | Ser | Ser | Gln | Tyr | Val | Ser | Ala | Leu | Leu | Met | Leu | Ala | Ala | |
| | | 195 | | | | | 200 | | | | | 205 | | | | |

| tgc | ggc | gaa | gca | ccg | att | gaa | gtg | gcg | ctg | acc | ggc | aag | gac | atc | ggc | 672 |
| Cys | Gly | Glu | Ala | Pro | Ile | Glu | Val | Ala | Leu | Thr | Gly | Lys | Asp | Ile | Gly | |
| | 210 | | | | | 215 | | | | | 220 | | | | | |

| gcc | cgt | ggc | tat | gtg | gac | ctg | acc | ctc | gat | tgc | atg | cgt | gcg | ttc | ggg | 720 |
| Ala | Arg | Gly | Tyr | Val | Asp | Leu | Thr | Leu | Asp | Cys | Met | Arg | Ala | Phe | Gly | |
| 225 | | | | | 230 | | | | | 235 | | | | | 240 | |

| gcc | cag | gta | gac | atc | gtg | gac | gac | acc | acc | tgg | cgc | gtg | gcc | ccc | acg | 768 |
| Ala | Gln | Val | Asp | Ile | Val | Asp | Asp | Thr | Thr | Trp | Arg | Val | Ala | Pro | Thr | |
| | | | | 245 | | | | | 250 | | | | | 255 | | |

| ggc | tat | acc | gcc | cat | gat | tac | ctg | atc | gaa | ccc | gac | gct | tcc | gcc | gcc | 816 |
| Gly | Tyr | Thr | Ala | His | Asp | Tyr | Leu | Ile | Glu | Pro | Asp | Ala | Ser | Ala | Ala | |
| | | | 260 | | | | | 265 | | | | | 270 | | | |

| act | tac | ctg | tgg | gcc | gca | gaa | gta | ctg | acc | ggt | ggc | cgt | atc | gat | att | 864 |
| Thr | Tyr | Leu | Trp | Ala | Ala | Glu | Val | Leu | Thr | Gly | Gly | Arg | Ile | Asp | Ile | |
| | | 275 | | | | | 280 | | | | | 285 | | | | |

-continued

| | |
|---|---|
| ggt gta gcc gcg cag gac ttc acc cag ccc gac gcc aag gca cag gcc<br>Gly Val Ala Ala Gln Asp Phe Thr Gln Pro Asp Ala Lys Ala Gln Ala<br>290                           295                       300 | 912 |
| gtg atc gcg caa ttc ccg aac atg cag gcc acg gtg gtg ggt tca caa<br>Val Ile Ala Gln Phe Pro Asn Met Gln Ala Thr Val Val Gly Ser Gln<br>305                       310                          315                   320 | 960 |
| atg cag gat gcg atc ccg acc ctg gcg gtg ctc gcc gca ttc aac aat<br>Met Gln Asp Ala Ile Pro Thr Leu Ala Val Leu Ala Ala Phe Asn Asn<br>                         325                          330                       335 | 1008 |
| acc ccg gtg cgc ttc act gaa ctg gcg aac ctg cgc gtc aag gaa tgt<br>Thr Pro Val Arg Phe Thr Glu Leu Ala Asn Leu Arg Val Lys Glu Cys<br>                    340                         345                       350 | 1056 |
| gac cgc gtg cag gcg ctg cac gat ggc ctc aac gaa att cgc ccg ggc<br>Asp Arg Val Gln Ala Leu His Asp Gly Leu Asn Glu Ile Arg Pro Gly<br>                355                         360                       365 | 1104 |
| ctg gcg acc atc gaa ggt gat gac ctg ctg gtt gcc agc gac ccc gct<br>Leu Ala Thr Ile Glu Gly Asp Asp Leu Leu Val Ala Ser Asp Pro Ala<br>370                           375                       380 | 1152 |
| ttg gct ggc acc gcc tgc acc gca ctg atc gat acc cac gcc gac cat<br>Leu Ala Gly Thr Ala Cys Thr Ala Leu Ile Asp Thr His Ala Asp His<br>385                         390                          395                   400 | 1200 |
| cgc atc gcc atg tgc ttt gcc ctg gcc ggg ctg aaa gtc tcg ggc att<br>Arg Ile Ala Met Cys Phe Ala Leu Ala Gly Leu Lys Val Ser Gly Ile<br>                         405                          410                       415 | 1248 |
| cgc atc caa gac cct gat tgc gta gcc aag acc tac cct gac tac tgg<br>Arg Ile Gln Asp Pro Asp Cys Val Ala Lys Thr Tyr Pro Asp Tyr Trp<br>                    420                         425                       430 | 1296 |
| aaa gcg ctg gcc agc ctg ggc gtt cac tta agc tac<br>Lys Ala Leu Ala Ser Leu Gly Val His Leu Ser Tyr<br>               435                         440 | 1332 |

<210> SEQ ID NO 58
<211> LENGTH: 1236
<212> TYPE: DNA
<213> ORGANISM: Ochrobactrum/Brucella
<220> FEATURE:
<221> NAME/KEY: CDS
<222> LOCATION: (1)...(1236)

<400> SEQUENCE: 58

| | |
|---|---|
| gtg acc gtt aca ccg ccc aac ttc ccc ctc act ggc aag gtc gcg ccc<br>Met Thr Val Thr Pro Pro Asn Phe Pro Leu Thr Gly Lys Val Ala Pro<br>1                     5                          10                       15 | 48 |
| ccc ggc tcc aaa tcc att acc aac cgt gcg ctg ttg ctc gcg gca ctg<br>Pro Gly Ser Lys Ser Ile Thr Asn Arg Ala Leu Leu Leu Ala Ala Leu<br>                 20                          25                       30 | 96 |
| gcc aag ggc acc agc cgt ttg agc ggt gcg ctc aaa agc gat gac acg<br>Ala Lys Gly Thr Ser Arg Leu Ser Gly Ala Leu Lys Ser Asp Asp Thr<br>        35                          40                       45 | 144 |
| cgc cac atg tcg gtc gcc ctg cgg cag atg ggc gtc acc atc gac gag<br>Arg His Met Ser Val Ala Leu Arg Gln Met Gly Val Thr Ile Asp Glu<br>    50                          55                          60 | 192 |
| ccg gac gac acc acc ttt gtc gtc acc agc caa ggc tcg ctc caa ttg<br>Pro Asp Asp Thr Thr Phe Val Val Thr Ser Gln Gly Ser Leu Gln Leu<br>65                           70                       75                   80 | 240 |
| ccg gcc cag ccg ttg ttc ctc ggc aac gcc ggc acc gcc atg cgc ttt<br>Pro Ala Gln Pro Leu Phe Leu Gly Asn Ala Gly Thr Ala Met Arg Phe<br>                         85                          90                       95 | 288 |
| ctc acg gct gcc gtc gcc acc gtg caa ggc acc gtg gta ctg gac ggt<br>Leu Thr Ala Ala Val Ala Thr Val Gln Gly Thr Val Val Leu Asp Gly<br>                100                         105                       110 | 336 |

| | |
|---|---|
| gac gag tac atg caa aaa cgc ccg atc ggc ccg ctg ctg gcc acc ctg<br>Asp Glu Tyr Met Gln Lys Arg Pro Ile Gly Pro Leu Leu Ala Thr Leu<br>115                         120                     125 | 384 |
| ggc cag aac ggc atc cag gtc gac agc ccc acc ggt tgc cca ccg gta<br>Gly Gln Asn Gly Ile Gln Val Asp Ser Pro Thr Gly Cys Pro Pro Val<br>    130                   135                   140 | 432 |
| acg gtg cat ggc gcg ggc aag gtc cag gcc agg cgt ttt gag att gac<br>Thr Val His Gly Ala Gly Lys Val Gln Ala Arg Arg Phe Glu Ile Asp<br>145                         150                     155                   160 | 480 |
| gga ggc ttg tcc agc cag tac gta tcg gcc ctg ctg atg ctg gcg gcg<br>Gly Gly Leu Ser Ser Gln Tyr Val Ser Ala Leu Leu Met Leu Ala Ala<br>                   165                   170                   175 | 528 |
| tgc ggc gaa gca ccg att gaa gtg gcg ctg acc ggc aag gac atc ggc<br>Cys Gly Glu Ala Pro Ile Glu Val Ala Leu Thr Gly Lys Asp Ile Gly<br>180                         185                     190 | 576 |
| gcc cgt ggc tat gtg gac ctg acc ctc gat tgc atg cgt gcg ttc ggg<br>Ala Arg Gly Tyr Val Asp Leu Thr Leu Asp Cys Met Arg Ala Phe Gly<br>                   195                   200                   205 | 624 |
| gcc cag gta gac atc gtg gac gac acc acc tgg cgc gtg gcc ccc acg<br>Ala Gln Val Asp Ile Val Asp Asp Thr Thr Trp Arg Val Ala Pro Thr<br>210                         215                     220 | 672 |
| ggc tat acc gcc cat gat tac ctg atc gaa ccc gac gct tcc gcc gcc<br>Gly Tyr Thr Ala His Asp Tyr Leu Ile Glu Pro Asp Ala Ser Ala Ala<br>225                       230                   235                   240 | 720 |
| act tac ctg tgg gcc gca gaa gta ctg acc ggt ggc cgt atc gat att<br>Thr Tyr Leu Trp Ala Ala Glu Val Leu Thr Gly Gly Arg Ile Asp Ile<br>                   245                   250                   255 | 768 |
| ggt gta gcc gcg cag gac ttc acc cag ccc gac gcc aag gca cag gcc<br>Gly Val Ala Ala Gln Asp Phe Thr Gln Pro Asp Ala Lys Ala Gln Ala<br>260                         265                     270 | 816 |
| gtg atc gcg caa ttc ccg aac atg cag gcc acg gtg gtg ggt tca caa<br>Val Ile Ala Gln Phe Pro Asn Met Gln Ala Thr Val Val Gly Ser Gln<br>                   275                   280                   285 | 864 |
| atg cag gat gcg atc ccg acc ctg gcg gtg ctc gcc gca ttc aac aat<br>Met Gln Asp Ala Ile Pro Thr Leu Ala Val Leu Ala Ala Phe Asn Asn<br>290                         295                     300 | 912 |
| acc ccg gtg cgc ttc act gaa ctg gcg aac ctg cgc gtc aag gaa tgt<br>Thr Pro Val Arg Phe Thr Glu Leu Ala Asn Leu Arg Val Lys Glu Cys<br>305                         310                     315                   320 | 960 |
| gac cgc gtg cag gcg ctg cac gat ggc ctc aac gaa att cgc ccg ggc<br>Asp Arg Val Gln Ala Leu His Asp Gly Leu Asn Glu Ile Arg Pro Gly<br>                   325                   330                   335 | 1008 |
| ctg gcg acc atc gaa ggt gat gac ctg ctg gtt gcc agc gac ccc gct<br>Leu Ala Thr Ile Glu Gly Asp Asp Leu Leu Val Ala Ser Asp Pro Ala<br>                   340                   345                   350 | 1056 |
| ttg gct ggc acc gcc tgc acc gca ctg atc gat acc cac gcc gac cat<br>Leu Ala Gly Thr Ala Cys Thr Ala Leu Ile Asp Thr His Ala Asp His<br>                   355                   360                   365 | 1104 |
| cgc atc gcc atg tgc ttt gcc ctg gcc ggg ctg aaa gtc tcg ggc att<br>Arg Ile Ala Met Cys Phe Ala Leu Ala Gly Leu Lys Val Ser Gly Ile<br>370                         375                     380 | 1152 |
| cgc atc caa gac cct gat tgc gta gcc aag acc tac cct gac tac tgg<br>Arg Ile Gln Asp Pro Asp Cys Val Ala Lys Thr Tyr Pro Asp Tyr Trp<br>385                         390                     395                   400 | 1200 |
| aaa gcg ctg gcc agc ctg ggc gtt cac tta agc tac<br>Lys Ala Leu Ala Ser Leu Gly Val His Leu Ser Tyr<br>                   405                   410 | 1236 |

<210> SEQ ID NO 59
<211> LENGTH: 412

<212> TYPE: PRT
<213> ORGANISM: Ochrobactrum/Brucella

<400> SEQUENCE: 59

```
Met Thr Val

```
Lys Ala Leu Ala Ser Leu Gly Val His Leu Ser Tyr
            405                 410
```

<210> SEQ ID NO 60
<211> LENGTH: 1496
<212> TYPE: DNA
<213> ORGANISM: Unknown
<220> FEATURE:
<223> OTHER INFORMATION: Isolated from soil sample

<400> SEQUENCE: 60

| | | | | | |
|---|---|---|---|---|---|
| aagcaccggc | tcacaaattc | ccgccgatat | tccgatagcc | cggctttgcg | ccgcattctt | 60 |
| tgacaagacg | acgatcatga | tcgaactgac | catcaccccg | cccggccacc | cgctttccgg | 120 |
| caaggtggag | ccgcccggtt | ccaaatccat | taccaaccgt | gcacttctgc | tggccgggct | 180 |
| cgccaagggc | aaaagccgtc | tcacgggcgc | gctgaaaagc | gacgatacgc | tttacatggc | 240 |
| agaagcgctg | cgtgagatgg | gtgtcaaggt | aaccgagcct | gacgcgacca | ccttcgtggt | 300 |
| ggagagttca | ggtgggttgc | atcagccgga | aaagccgctt | ttcctcggca | atgccggcac | 360 |
| agctacccgc | tttctcaccg | ccgctgccgc | ccttgtggat | ggcgccgtca | tcatcgatgg | 420 |
| cgacgagcat | atgcgcaaac | gcccgatcat | gccgctggtg | aagccctgc | gctccctcgg | 480 |
| cgttgaggcg | gaggcgccga | ccggctgccc | gccgtcacc | gtctgcggta | agggtactgg | 540 |
| cttcccgaag | ggcagcgtca | cgatcgacgc | caacctttcc | agccagtatg | tgtccgcact | 600 |
| tctgatggcc | gccgcctgcg | cgacaagcc | tgtcgatatc | atcctcaaag | gtgaggaaat | 660 |
| cggcgcgaag | ggctatatcg | atctcaccac | atcggccatg | gaagccttcg | gcgcaaaggt | 720 |
| ggagcgggtc | agcaacgcca | tctggcgcgt | gcatccgacc | ggctacacgg | cgaccgattt | 780 |
| ccatatcgag | ccggatgcct | cggccgccac | ctatctctgg | ggcgctgagc | ttttgaccgg | 840 |
| cggcgccatc | gatatcggta | cgccggccga | caagttcacc | cagccggatg | ccaaggccca | 900 |
| tgaggtcatg | gcgcaatttc | cgcatctgcc | cgccgaaatc | gacggttcgc | agatgcagga | 960 |
| tgccattccc | accattgccg | ttctcgccgc | ctttaacgaa | acgccggtgc | gtttcgtcgg | 1020 |
| catcgccaat | ctgcgcgtca | aggagtgcga | ccgaatccgc | gccgtctcac | tcggcctcaa | 1080 |
| cgaaatccgc | gatggtctgg | cgcatgagga | aggcgacgac | ttgatcgtgc | attccgatcc | 1140 |
| ttcgcttgcg | ggccagacgg | tgaatgcctc | catcgacact | ttcgccgacc | accgtatcgc | 1200 |
| catgagcttt | gcgctggcgg | cgctgaagat | cggcggcatt | gccatccaga | tccggcctg | 1260 |
| cgtgggcaag | acctatcccg | gttactggaa | ggcgctcgcc | tcgctgggag | tcgaatactc | 1320 |
| ggaaaaggaa | accgctgccg | agccgcagca | ttagaagaac | ggtattggtt | ttccgtcatt | 1380 |
| ccggccctga | gccggaatcc | agtgcgatca | agtccttgat | cgcgaaagac | tcttcaagcc | 1440 |
| gcgcagacgc | gcggctgctg | gataccgggt | ctagcccggt | atgacggcaa | tgactg | 1496 |

<210> SEQ ID NO 61
<211> LENGTH: 33
<212> TYPE: DNA
<213> ORGANISM: Artificial Sequence
<220> FEATURE:
<223> OTHER INFORMATION: oligonucleotide

<400> SEQUENCE: 61
cagagatctg gcatgcgacc tcaagccact ctc                33

<210> SEQ ID NO 62
<211> LENGTH: 31

```
<212> TYPE: DNA
<213> ORGANISM: Artificial Sequence
<220> FEATURE:
<223> OTHER INFORMATION: oligonucleotide

<400> SEQUENCE: 62
cagggcgcgc ctcagcgctg aacactcacc c                          31

<210> SEQ ID NO 63
<211> LENGTH: 34
<212> TYPE: DNA
<213> ORGANISM: Artificial Sequence
<220> FEATURE:
<223> OTHER INFORMATION: oligonucleotide

<400> SEQUENCE: 63
cagggatccg gcatgatcga actgaccatc accc                       34

<210> SEQ ID NO 64
<211> LENGTH: 33
<212> TYPE: DNA
<213> ORGANISM: Artificial Sequence
<220> FEATURE:
<223> OTHER INFORMATION: oligonucleotide

<400> SEQUENCE: 64
cagggcgcgc ctcagtgctg cggctcggca gcg                        33

<210> SEQ ID NO 65
<211> LENGTH: 33
<212> TYPE: DNA
<213> ORGANISM: Artificial Sequence
<220> FEATURE:
<223> OTHER INFORMATION: oligonucleotide

<400> SEQUENCE: 65
cagggatccg gcatgcgacc tcaagccacc ctc                        33

<210> SEQ ID NO 66
<211> LENGTH: 31
<212> TYPE: DNA
<213> ORGANISM: Artificial Sequence
<220> FEATURE:
<223> OTHER INFORMATION: oligonucleotide

<400> SEQUENCE: 66
cagggcgcgc ctcagcgctg aacactcaca c                          31

<210> SEQ ID NO 67
<211> LENGTH: 33
<212> TYPE: DNA
<213> ORGANISM: Artificial Sequence
<220> FEATURE:
<223> OTHER INFORMATION: oligonucleotide

<400> SEQUENCE: 67
cagggatccg gcatgcgacc tcaagccacc ctc                        33

<210> SEQ ID NO 68
<211> LENGTH: 30
<212> TYPE: DNA
<213> ORGANISM: Artificial Sequence
<220> FEATURE:
```

-continued

```
<223> OTHER INFORMATION: oligonucleotide

<400> SEQUENCE: 68
agaggcgcgc ctcagcgctg aacacgcacc                                    30
```